(12) United States Patent
Priceman et al.

(10) Patent No.: US 11,466,097 B2
(45) Date of Patent: Oct. 11, 2022

(54) CHIMERIC ANTIGEN RECEPTORS TARGETED TO PSCA

(71) Applicant: City of Hope, Duarte, CA (US)

(72) Inventors: Saul J. Priceman, Duarte, CA (US); Christine E. Brown, Duarte, CA (US); Stephen J. Forman, Duarte, CA (US)

(73) Assignee: City of Hope, Duarte, CA (US)

( * ) Notice: Subject to any disclaimer, the term of this patent is extended or adjusted under 35 U.S.C. 154(b) by 791 days.

(21) Appl. No.: 15/766,674

(22) PCT Filed: Oct. 6, 2016

(86) PCT No.: PCT/US2016/055761
§ 371 (c)(1),
(2) Date: Apr. 6, 2018

(87) PCT Pub. No.: WO2017/062628
PCT Pub. Date: Apr. 13, 2017

(65) Prior Publication Data
US 2020/0308300 A1    Oct. 1, 2020

Related U.S. Application Data

(60) Provisional application No. 62/238,062, filed on Oct. 6, 2015.

(51) Int. Cl.
| | | |
|---|---|---|
| A61P 35/00 | (2006.01) |
| C07K 16/30 | (2006.01) |
| A61P 35/04 | (2006.01) |
| A61K 35/17 | (2015.01) |
| C07K 14/725 | (2006.01) |
| C07K 14/73 | (2006.01) |
| C07K 14/705 | (2006.01) |
| C12N 5/0783 | (2010.01) |
| C07H 21/00 | (2006.01) |
| C07H 21/04 | (2006.01) |
| C12N 15/63 | (2006.01) |
| C12N 15/11 | (2006.01) |
| C12N 15/00 | (2006.01) |
| C12N 15/10 | (2006.01) |
| C12N 5/00 | (2006.01) |
| C12N 15/09 | (2006.01) |
| C12N 15/79 | (2006.01) |
| C12N 15/70 | (2006.01) |
| C12N 15/62 | (2006.01) |
| C12N 15/85 | (2006.01) |
| C12N 15/74 | (2006.01) |
| C12N 5/078 | (2010.01) |
| C12N 5/071 | (2010.01) |
| A61P 19/08 | (2006.01) |
| A61K 48/00 | (2006.01) |
| A61P 1/18 | (2006.01) |
| C12N 5/07 | (2010.01) |
| C12N 5/10 | (2006.01) |
| C07H 19/06 | (2006.01) |
| C07H 19/00 | (2006.01) |
| C07H 19/16 | (2006.01) |

(52) U.S. Cl.
CPC .......... *C07K 16/3069* (2013.01); *A61K 35/17* (2013.01); *A61K 48/00* (2013.01); *A61P 1/18* (2018.01); *A61P 19/08* (2018.01); *A61P 35/00* (2018.01); *A61P 35/04* (2018.01); *C07H 21/00* (2013.01); *C07H 21/04* (2013.01); *C07K 14/7051* (2013.01); *C07K 14/70514* (2013.01); *C07K 14/70517* (2013.01); *C07K 14/70521* (2013.01); *C12N 5/00* (2013.01); *C12N 5/06* (2013.01); *C12N 5/0602* (2013.01); *C12N 5/0634* (2013.01); *C12N 5/0636* (2013.01); *C12N 5/10* (2013.01); *C12N 15/00* (2013.01); *C12N 15/09* (2013.01); *C12N 15/10* (2013.01); *C12N 15/11* (2013.01); *C12N 15/62* (2013.01); *C12N 15/63* (2013.01); *C12N 15/70* (2013.01); *C12N 15/74* (2013.01); *C12N 15/79* (2013.01); *C12N 15/85* (2013.01); *C07H 19/00* (2013.01); *C07H 19/06* (2013.01); *C07H 19/16* (2013.01); *C07K 2317/24* (2013.01); *C07K 2317/53* (2013.01); *C07K 2317/622* (2013.01); *C07K 2317/73* (2013.01); *C07K 2317/76* (2013.01); *C07K 2319/02* (2013.01); *C07K 2319/03* (2013.01); *C07K 2319/33* (2013.01); *C12N 15/8509* (2013.01); *C12N 2015/8518* (2013.01); *C12N 2015/8572* (2013.01)

(58) Field of Classification Search
None
See application file for complete search history.

(56) References Cited

U.S. PATENT DOCUMENTS

2015/0139943 A1    5/2015  Campana et al.

FOREIGN PATENT DOCUMENTS

| RU | 2381234 | 2/2010 |
| WO | WO 2005/000898 | 1/2005 |
| WO | WO 2009/032949 | 3/2009 |
| WO | WO 2012/079000 | 6/2012 |

(Continued)

OTHER PUBLICATIONS

Katari et al. (HPB 2011, 13, 643-650). (Year: 2011).*
Shi et al. (Molecular Cancer 2014, 13:219). (Year: 2014).*
Jonnalagadda et al. (Journal for ImmunoTherapy of Cancer 2013 1(Suppl 1):P18). (Year: 2013).*

(Continued)

*Primary Examiner* — Zachary S Skelding
(74) *Attorney, Agent, or Firm* — Fish & Richardson P.C.

(57) ABSTRACT

Chimeric transmembrane immunoreceptors (CAR) targeted to PSCA are described.

13 Claims, 23 Drawing Sheets
Specification includes a Sequence Listing.

(56) References Cited

FOREIGN PATENT DOCUMENTS

| WO | WO 2014/031687 | 2/2014 | | |
|---|---|---|---|---|
| WO | WO 2014/144622 | 9/2014 | | |
| WO | WO-2015066551 A2 | * | 5/2015 | ............... A61P 7/00 |
| WO | WO 2015/105522 | 7/2015 | | |
| WO | WO 2015/123527 | 8/2015 | | |
| WO | WO 2015/157399 | 10/2015 | | |
| WO | WO-2017027325 A1 | * | 2/2017 | ......... C07K 16/3069 |

OTHER PUBLICATIONS

Vajdos et al. (J Mol Biol. Jul. 5, 2002;320(2):415-28). (Year: 2002).*

Bedouelle et al. (FEBS J. Jan. 2006;273(1):34-46). (Year: 2006).*

Brown et al. (J Immunol. May 1, 1996; 156(9):3285-91). (Year: 1996).*

Colman (Research in Immunology, 145:33-36, 1994). (Year: 1994).*

Tang et al., "The Foxp3+ regulatory T cell: a jack of all trades, master of regulation," Nat Immunol., 2008, 9(3):239-244.

Zhong et al., "Chimeric Antigen Receptors Combining 4-1BB and CD28 Signaling Domains Augment P13kinase/AKT/Bcl-XL Activation and CD8+ T cell-mediated Tumor Eradication," Mol Ther., 2010, 18(2):413-420.

Diamond et al., "Somatic mutation of the T15 heavy chain gives rise to an antibody with autoantibody specificity," Proc Natl Acad Sci USA., 1984, 81:5841-5844.

Feldmann et al., "Novel Humanized and Highly Efficient Bispecific Antibodies Mediate Killing of Prostate Stem Cell Antigen-Expressing Tumor Cells by CD8+ and CD4+ T Cells," J Immunol., 2012, 189:3249-3259.

Lepin et al., "An affinity matured minibody for PET imaging of prostate stem cell antigen (PSCA)-expressing tumors," Eur J Nucl Med Mol Imaging., 2010, 37:1529-1538.

Ohno et al., "Antigen-binding specificities of antibodies are primarily determined by seven residues of VH," Proc Natl Acad Sci USA., May 1985, 82:2945-2949.

Priceman et al., "Co-stimulatory signaling determines tumor antigen sensitivity and persistence of CAR T cells targeting PSCA+ metastatic prostate cancer," Oncoimmunology, 2018, 7(2):e1380764.

Rudikoff et al., "Single amino acid substitution altering antigen-binding specificity," Proc Nat Acad Sci USA Immunology., 1982, 79:1979-1983.

Abate-Daga et al., "A novel chimeric antigen receptor against prostate stem cell antigen mediates tumor destruction in a humanized mouse model of pancreatic cancer," Hum Gene Ther., Dec. 2014.

Abate-Daga et al., "Pancreatic cancer: Hurdles in the engineering of CAR-based immunotherapies," Oncoimmunology, Jun. 18, 2014, 3:e29194-1-e29194-3.

Ahmed et al. "HER2-specific T cells target primary glioblastoma stem cells and induce regression of autologous experimental tumors," Clin Cancer Res, Jan. 15, 2010, 16(2):474-485.

Brown et al. "Stem-like tumor-initiating cells isolated from IL13Rα2 expressing gliomas are targeted and killed by IL13-zetakine-redirected T Cells," Clin Cancer Res., Apr. 15, 2012, 18(8):2199-209.

Brown et al. "Tumor-derived chemokine MCP-1/CCL2 is sufficient for mediating tumor tropism of adoptively transferred T cells," J Immunol., 2007, 179(5):3332-3341.

Cartellieri et al. "Chimeric antigen receptor-engineered T cells for immunotherapy of cancer," J Biomed Biotechnol, May 5, 2010, 2010:956304.

Cartellieri et al., "A Novel Ex Vivo Isolation and Expansion Procedure for Chimeric Antigen Receptor Engrafted Human T Cells," PLOS ONE, Apr. 2014, 9(4):e93745.

Chow et al., "T Cells Redirected to EphA2 for the Immunotherapy of Glioblastoma," Mol Ther., 2013, 21(3):629-637.

Doth et al., "Design and development of therapies using chimeric antigen receptor-expressing T cells," Immunological Reviews, Jan. 2014, 257(1):107-126.

Edelman et al. "The covalent structure of an entire gammaG immunoglobulin molecule," Proc Natl Acad Sci USA, May 1969, 63(1):78-85.

Grada et al., "TanCAR: A Novel Bispecific Chimeric Antigen Receptor for Cancer Immunotherapy," Molecular Therapy-Nucleic Acids, Jan. 1, 2013, 2:e105.

Hong et al., "Successful treatment of melanoma brain metastases with adoptive cell therapy," Clin Cancer Res, 2010, 16(19):4892-4898.

Hillerdal et al., "Systemic Treatment with CAR-engineered T cells against PSCA delays subcutaneous tumor growth and prolongs survival of mice," BMC Cancer, Jan. 2014, 14:30.

Hudecek et al., "The nonsignaling extracellular spacer domain of chimeric antigen receptors is decisive for in vivo atitumor activity," Cancer Immunology Research, Feb. 2015, 3(2):125-135.

Jonnalagadda et al., "Chimeric Antigen Receptors with Mutated IgG4 Fc Spacer Avoid Fc Receptor Binding and Improve T Cell Persistence and Antitumor Efficacy," Mol Ther,. Apr. 2015, 23(4):757-68.

Long et al., "4-1BB costimulation amerliorates T cell exhhaustion induced by tonic signalling of chimeric antigen receptors," Nature Medicine, May 4, 2015, 21(6):581-590.

Pule et al., "A Chimeric T cell antigen receptor that augments cytokine release and supports clonal expansion of primary human T cells," Molecular Therapy: The Journal of the American Society of Gene Therapy, Nov. 2005, 12(5):933-941.

Sampson et al. "EGFRvIII mCAR-modified T-cell therapy cures mice with established intracerebral glioma and generates host immunity against tumor-antigen loss," Clin Cancer Res., Feb. 15, 2014, 20(4):972-94.

Yaghoubi ,"Noninvasive detection of therapeutic cytolytic T cells with 18F-FHBG PET in a patient with glioma," Nat Clin Pract Oncol, Jan. 2009, 6(1):53-58.

International Preliminary Report on Patentability in International Application No. PCT/US2016/055761, dated Apr. 10, 2018, 12 pages.

International Search Report and Written Opinion in International Application No. PCT/US2016/055761, dated Feb. 14, 2017.

European Search Report in European Application No. 20170726.2, dated Oct. 5, 2020, 20 pages.

Klingemann, "Are natural killer cells superior CAR drivers?" Oncoimmunology, Jan. 1, 2014, 3(1):e28147.

Kunkele et al., "Functional Tuning of CARs Reveals Signaling Threshold above which CD8+ Antitumor Potency Is Attenuated due to Cell Fas-FasL-Dependent AICD," Cancer Immunology Research, Apr. 1, 2015, 3(4):368-379.

Porter et al., "Chimeric Antigen Receptor-Modified T Cells in Chronic Lymphoid Leukemia" New England Journal of Medicine, Aug. 25, 2011, 365(8):725-733.

* cited by examiner

PSCAscFv-IgG4(HL-CH3)-CD4tm-41BB-Zeta

MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT
<u>GMCSFRa signal peptide</u>   <u>PSCAscFv</u>

YYCQQWGSSPPFTFGQGTKVEIKGSTSGGGSGGGGSGGGGSSEVQLVEYGGGLVQPGGSLRLSCAASGFNIKDYYIHWVRQAPGKGLEWVAWIDPENGD

TEFVPKFQGRATMSADTSKNTAYLQMNSLRAEDTAVYYCKTGGFWGQGTLVTVSSESKYGPPCPPCPGGGSSGGGGSGGQPREPQVYTLPPSQEEMTK
                                                                    <u>IgG4(SmP)-H</u>      <u>IgG4 CH3</u>

NQVSLTCLVKGFYPSDIAVEWESNGQPENNYKTTPPVLDSDGSFFLYSRLTVDKSRWQEGNVFSCSVMHEALHNHYTQKSLSLSLGKMALIVLGGVAGLL
                                                                                                <u>CD4 tm</u>

LFIGLGIFFKRGRKKLLYIFKQPFMRPVQTTQEEDGCSCRFPEEEEGGCELGGGRVKFSRSADAPAYQQGQNQLYNELNLGRREEYDVLDKRRGRDPEMG
                                                                        <u>Zeta</u>
<u>4-1BB cyto</u>
GKPRRKNPQEGLYNELQKDKMAEAYSEIGMKGERRRGKGHDGLYQGLSTATKDTYDALHMQALPPR

FIG. 18

PSCAscFv-IgG4(S228P,L235E,N297Q)-CD28tm-CD28gg-Zeta-T2A-CD19t

MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT
GMCSFRa signal peptide  PSCAscFv YYCQQWGSSPFTFGQGTKVEIKGSTSGGGSGGGSGGGSSEVQLVEYGGGLVQPGGSLRLSCAASGFNIKDYYIHWVRQAPGKGLEWVAWIDPENGD TEFVPKFQGRATMSADTSKNTAYLQMNSLRAEDTAVYYCKTGGFWGQGTLVTVSSESKYGPPCPPCPAPEFEGGPSVFLFPPKPKDTLMISRTPEVTCVV
                                                                        IgG4(S228P,L235E,N297Q)

VDVSQEDPEVQFNWYVDGVEVHNAKTKPREEQFQSTYRVVSVLTVLHQDWLNGKEYKCKVSNKGLPSSIEKTISKAKGQPREPQVYTLPPSQEEMTKN

QVSLTCLVKGFYPSDIAVEWESNGQPENNYKTTPPVLDSDGSFFLYSRLTVDKSRWQEGNVFSCSVMHEALHNHYTQKSLSLSLGKMFWVLVVVGGVLA
                                                                                                CD28 tm

CYSLLVTVAFIIFWVRSKRSRGGHSDYMNMTPRRPGPTRKHYQPYAPPRDFAAYRSGGGRVKFSRSADAPAYQQGQNQLYNELNLGRREEYDVLDKRR
CD28cyto                                                      Zeta

GRDPEMGGKPRRKNPQEGLYNELQKDKMAEAYSEIGMKGERRRGKGHDGLYQGLSTATKDTYDALHMQALPPR

FIG. 19

PSCAscFv-Linker-CD4tm-41BB-Zeta

MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT
<u>GMCSFRa signal peptide</u>   <u>PSCAscFv</u>

YYCQQWGSSPFTFGQGTKVEIKGSTSGGGSGGGGSGGGGSSEVQLVEYGGGLVQPGGSLRLSCAASGFNIKDYYIHWVRQAPGKGLEWVAWIDPENGD

TEFVPKFQGRATMSADTSKNTAYLQMNSLRAEDTAVYYCKTGGFWGQGTLVTVSSGGGSSGGGGSGMALIVLGGVAGLLLFIGLGIFFKRGRKKLLYIF
                                                          <u>Linker</u>        <u>CD4 tm</u>              <u>4-1BB cyto</u>

KQPFMRPVQTTQEEDGCSCRFPEEEEGGCELGGGRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR
                    <u>Zeta</u>

FIG. 20

PSCAscFv-IgG4(HL-CH3)-CD28tm-CD28gg-Zeta

MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT
<u>GMCSFRa signal peptide</u>   <u>PSCAscFv</u>

YYCQQWGSSPFTFGQGTKVEIKGSTSGGGSGGGGSGGGGSSEVQLVEYGGGLVQPGGSLRLSCAASGFNIKDYYIHWVRQAPGKGLEWVAWIDPENGD

TEFVPKFQGRATMSADTSKNTAYLQMNSLRAEDTAVYYCKTGGFWGQGTLVTVSSESKYGPPCPPCPGGGSSGGGSGGQPREPQVYTLPPSQEEMTK
                                                           <u>IgG4(SmP)-H</u>    <u>Linker</u>       <u>IgG4-CH3</u>

NQVSLTCLVKGFYPSDIAVEWESNGQPENNYKTTPPVLDSDGSFFLYSRLTVDKSRWQEGNVFSCSVMHEALHNHYTQKSLSLSLGKMFWVLVVVGGVL
                                                                                            <u>CD28 tm</u>

ACYSLLVTVAFIIFWVRSKRSRGGHSDYMNMTPRRPGPTRKHYQPYAPPRDFAAYRSGGGRVKFSRSADAPAYQQGQNQLYNELNLGRREEYDVLDKR
         <u>CD28cyto</u>                                                                 <u>Zeta</u>

RGRDPEMGGKPRRKNPQEGLYNELQKDKMAEAYSEIGMKGERRRGKGHDGLYQGLSTATKDTYDALHMQALPPR

FIG. 21

PSCAscFv-IgG4(S228P,L235E,N297Q)-CD4tm-41BB-Zeta

MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT
GMCSFRa signal peptide    PSCAscFv YYCQQWGSSPFTFGQGTKVEIKGSTSGGGSGGGSGGGSSEVQLVEYGGGLVQPGGSLRLSCAASGFNIKDYYIHWVRQAPGKGLEWVAWIDPENGD TEFVPKFQGRATMSADTSKNTAYLQMNSLRAEDTAVYYCKTGGFWGQGTLVTVSSESKYGPPCPPCPAPEFEGGPSVFLFPPKPKDTLMISRTPEVTCVV
                                                                    IgG4(S228P,L235E,N297Q)

VDVSQEDPEVQFNWYVDGVEVHNAKTKPREEQFQSTYRVVSVLTVLHQDWLNGKEYKCKVSNKGLPSSIEKTISKAKGQPREPQVYTLPPSQEEMTKN

QVSLTCLVKGFYPSDIAVEWESNGQPENNYKTTPPVLDSDGSFFLYSRLTVDKSRWQEGNVFSCSVMHEALHNHYTQKSLSLSLGKMALIVLGGVAGLLL
                                                                                              CD4 tm

FIGLGIFFKRGRKKLLYIFKQPFMRPVQTTQEEDGCSCRFPEEEEGGCELGGGGRVKFSRSADAPAYQQGQNQLYNELNLGRREEYDVLDKRRGRDPEMGG
 4-1BB cyto                                                          Zeta

KPRRKNPQEGLYNELQKDKMAEAYSEIGMKGERRRGKGHDGLYQGLSTATKDTYDALHMQALPPR

FIG. 22

PSCAscFv-Linker-CD28tm-CD28gg-Zeta

<u>MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT</u>
<u>GMCSFRa signal peptide</u>   PSCAscFv YYCQQWGSSPFTFGQGTKVEIKGSTSGGGSGGGGSGGGGSSEVQLVEYGGGLVQPGGSLRLSCAASGFNIKDYYIHWVRQAPGKGLEWVAWIDPENGD TEFVPKFQGRATMSADTSKNTAYLQMNSLRAEDTAVYYCKTGGFWGQGTLVTVSSGGGSSGGGSGMFWVLVVVGGVLACYSLLVTVAFIIFWV<u>RSKRS</u>
                                                                <u>Linker</u>         CD28 tm        <u>CD28cyto</u>

<u>RGG</u><u>HSDYMNMTPRRPGPTRKHYQPYAPPRDFAAYRSGGGRVKFSRSADAPAYQQGQNQLYNELNLGRREEYDVLDKRRGRDPEMGGKPRRKNPQE</u>
                                                        Zeta
<u>GLYNELQKDKMAEAYSEIGMKGERRRGKGHDGLYQGLSTATKDTYDALHMQALPPR</u>

FIG. 23

SEQUENCE LISTING

```
<160> NUMBER OF SEQ ID NOS: 38

<210> SEQ ID NO 1
<211> LENGTH: 236
<212> TYPE: PRT
<213> ORGANISM: Artificial Sequence
<220> FEATURE:
<223> OTHER INFORMATION: an scFv directed against PSCA

<400> SEQUENCE: 1

Asp Ile Gln Leu Thr Gln Ser Pro Ser Thr Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Gly Ser Ser Pro Phe Thr
                85                  90                  95
```

```
Phe Gly Gln Gly Thr Lys Val Glu Ile Lys Gly Ser Thr Ser Gly Gly
                100                 105                 110

Gly Ser Gly Gly Ser Gly Gly Gly Ser Ser Glu Val Gln Leu
        115                 120                 125

Val Glu Tyr Gly Gly Gly Leu Val Gln Pro Gly Gly Ser Leu Arg Leu
    130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190

Thr Met Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Lys Thr Gly Gly
    210                 215                 220

Phe Trp Gly Gln Gly Thr Leu Val Thr Val Ser Ser
225                 230                 235

<210> SEQ ID NO 2
<211> LENGTH: 10
<212> TYPE: DNA
<213> ORGANISM: Artificial Sequence
<220> FEATURE:
<223> OTHER INFORMATION: linker region - based on human

<400> SEQUENCE: 2 gggssgggsg                                                                10

<210> SEQ ID NO 3
<211> LENGTH: 12
<212> TYPE: PRT
<213> ORGANISM: Artificial Sequence
<220> FEATURE:
<223> OTHER INFORMATION: mutated sequence - based on human IgG4 hinge

<400> SEQUENCE: 3

Glu Ser Lys Tyr Gly Pro Pro Cys Pro Pro Cys Pro
1               5                   10

<210> SEQ ID NO 4
<211> LENGTH: 12
<212> TYPE: PRT
<213> ORGANISM: Homo sapiens

<400> SEQUENCE: 4

Glu Ser Lys Tyr Gly Pro Pro Cys Pro Ser Cys Pro
1               5                   10

<210> SEQ ID NO 5
<211> LENGTH: 20
<212> TYPE: PRT
<213> ORGANISM: Artificial Sequence
<220> FEATURE:
<223> OTHER INFORMATION: human IgG4 hinge and linker sequence

<400> SEQUENCE: 5

Glu Ser Lys Tyr Gly Pro Pro Cys Pro Cys Pro Gly Gly Gly Ser
1               5                   10                  15

Ser Gly Gly Gly
            20
```

<210> SEQ ID NO 6
<211> LENGTH: 39
<212> TYPE: PRT
<213> ORGANISM: Homo sapiens

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 7
<211> LENGTH: 48
<212> TYPE: PRT
<213> ORGANISM: Homo sapiens

<400> SEQUENCE: 7

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

<210> SEQ ID NO 8
<211> LENGTH: 45
<212> TYPE: PRT
<213> ORGANISM: Homo sapiens

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 9
<211> LENGTH: 129
<212> TYPE: PRT
<213> ORGANISM: Artificial Sequence
<220> FEATURE:
<223> OTHER INFORMATION: fusion of hinge-linker-CH3 /IgG4 HL-CH3

<400> SEQUENCE: 9

Glu Ser Lys Tyr Gly Pro Pro Cys Pro Pro Cys Pro Gly Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
        35                  40                  45

Cys Leu Val Lys Gly Phe Tyr Pro Ser Asp Ile Ala Val Glu Trp Glu
    50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
            115                 120                 125

Lys

<210> SEQ ID NO 10
<211> LENGTH: 229
<212> TYPE: PRT
<213> ORGANISM: Artificial Sequence
<220> FEATURE:
<223> OTHER INFORMATION: fusion with mutations

<400> SEQUENCE: 10

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Lys
225

<210> SEQ ID NO 11

<400> SEQUENCE: 11

000

<210> SEQ ID NO 12
<211> LENGTH: 107
<212> TYPE: PRT
<213> ORGANISM: Homo sapiens

```
<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 13
<211> LENGTH: 21
<212> TYPE: PRT
<213> ORGANISM: Homo sapiens

<400> SEQUENCE: 13

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 14
<211> LENGTH: 27
<212> TYPE: PRT
<213> ORGANISM: Homo sapiens

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 15
<211> LENGTH: 28
<212> TYPE: PRT
<213> ORGANISM: Homo sapiens

<400> SEQUENCE: 15

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 16
<211> LENGTH: 22
<212> TYPE: PRT
<213> ORGANISM: Homo sapiens

<400> SEQUENCE: 16

Met Ala Leu Ile Val Leu Gly Gly Val Ala Gly Leu Leu Leu Phe Ile
1               5                   10                  15

Gly Leu Gly Ile Phe Phe
            20
```

<210> SEQ ID NO 17
<211> LENGTH: 21
<212> TYPE: PRT
<213> ORGANISM: Artificial Sequence
<220> FEATURE:
<223> OTHER INFORMATION: transmembrane domain, CD8tm

<400> SEQUENCE: 17

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 18
<211> LENGTH: 23
<212> TYPE: PRT
<213> ORGANISM: Artificial Sequence
<220> FEATURE:
<223> OTHER INFORMATION: transmembrane domain, CD8tm2

<400> SEQUENCE: 18

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 19
<211> LENGTH: 24
<212> TYPE: PRT
<213> ORGANISM: Artificial Sequence
<220> FEATURE:
<223> OTHER INFORMATION: transmembrane domain, CD8tm3

<400> SEQUENCE: 19

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 20
<211> LENGTH: 27
<212> TYPE: PRT
<213> ORGANISM: Artificial Sequence
<220> FEATURE:
<223> OTHER INFORMATION: transmembrane domain, 41BB

<400> SEQUENCE: 20

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 21
<211> LENGTH: 112
<212> TYPE: PRT
<213> ORGANISM: Homo sapiens

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Gly Arg Asp Pro Glu Met Gly Gly Lys
                35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 22
<211> LENGTH: 41
<212> TYPE: PRT
<213> ORGANISM: Homo sapiens

<400> SEQUENCE: 22

Arg Ser Lys Arg Ser Arg Leu Leu His Ser Asp Tyr Met Asn Met Thr
 1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
                35                  40

<210> SEQ ID NO 23
<211> LENGTH: 41
<212> TYPE: PRT
<213> ORGANISM: Homo sapiens

<400> SEQUENCE: 23

Arg Ser Lys Arg Ser Arg Gly Gly His Ser Asp Tyr Met Asn Met Thr
 1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
                35                  40

<210> SEQ ID NO 24
<211> LENGTH: 42
<212> TYPE: PRT
<213> ORGANISM: Homo sapiens

<400> SEQUENCE: 24

Lys Arg Gly Arg Lys Lys Leu Leu Tyr Ile Phe Lys Gln Pro Phe Met
 1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
                35                  40

<210> SEQ ID NO 25
<211> LENGTH: 42
<212> TYPE: PRT
<213> ORGANISM: Homo sapiens

<400> SEQUENCE: 25

Ala Leu Tyr Leu Leu Arg Arg Asp Gln Arg Leu Pro Pro Asp Ala His
 1               5                   10                  15

Lys Pro Pro Gly Gly Gly Ser Phe Arg Thr Pro Ile Gln Glu Glu Gln
                20                  25                  30

Ala Asp Ala His Ser Thr Leu Ala Lys Ile
            35                  40

<210> SEQ ID NO 26
<211> LENGTH: 566
<212> TYPE: PRT
<213> ORGANISM: Artificial Sequence
<220> FEATURE:
<223> OTHER INFORMATION: chimeric protein sequence, Figure 18

<400> SEQUENCE: 26

Met Leu Leu Leu Val Thr Ser Leu Leu Cys Glu Leu Pro His Pro
1               5                   10                  15

Ala Phe Leu Leu Ile Pro Asp Ile Gln Leu Thr Gln Ser Pro Ser Thr
                20                  25                  30

Leu Ser Ala Ser Val Gly Asp Arg Val Thr Ile Thr Cys Ser Ala Ser
            35                  40                  45

Ser Ser Val Arg Phe Ile His Trp Tyr Gln Gln Lys Pro Gly Lys Ala
        50                  55                  60

Pro Lys Arg Leu Ile Tyr Asp Thr Ser Lys Leu Ala Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Trp
            100                 105                 110

Gly Ser Ser Pro Phe Thr Phe Gly Gln Gly Thr Lys Val Glu Ile Lys
        115                 120                 125

Gly Ser Thr Ser Gly Gly Gly Ser Gly Gly Gly Ser Gly Gly Gly Gly
130                 135                 140

Ser Ser Glu Val Gln Leu Val Glu Tyr Gly Gly Gly Leu Val Gln Pro
145                 150                 155                 160

Gly Gly Ser Leu Arg Leu Ser Cys Ala Ala Ser Gly Phe Asn Ile Lys
                165                 170                 175

Asp Tyr Tyr Ile His Trp Val Arg Gln Ala Pro Gly Lys Gly Leu Glu
            180                 185                 190

Trp Val Ala Trp Ile Asp Pro Glu Asn Gly Asp Thr Glu Phe Val Pro
        195                 200                 205

Lys Phe Gln Gly Arg Ala Thr Met Ser Ala Asp Thr Ser Lys Asn Thr
210                 215                 220

Ala Tyr Leu Gln Met Asn Ser Leu Arg Ala Glu Asp Thr Ala Val Tyr
225                 230                 235                 240

Tyr Cys Lys Thr Gly Gly Phe Trp Gly Gln Gly Thr Leu Val Thr Val
                245                 250                 255

Ser Ser Glu Ser Lys Tyr Gly Pro Pro Cys Pro Pro Cys Pro Gly Gly
            260                 265                 270

Gly Ser Ser Gly Gly Gly Ser Gly Gly Gln Pro Arg Glu Pro Gln Val
        275                 280                 285

Tyr Thr Leu Pro Pro Ser Gln Glu Glu Met Thr Lys Asn Gln Val Ser
290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
                325                 330                 335

Val Leu Asp Ser Asp Gly Ser Phe Phe Leu Tyr Ser Arg Leu Thr Val
            340                 345                 350

```
Asp Lys Ser Arg Trp Gln Glu Gly Asn Val Phe Ser Cys Ser Val Met
            355                 360                 365

His Glu Ala Leu His Asn His Tyr Thr Gln Lys Ser Leu Ser Leu Ser
            370                 375                 380

Leu Gly Lys Met Ala Leu Ile Val Leu Gly Gly Val Ala Gly Leu Leu
385                 390                 395                 400

Leu Phe Ile Gly Leu Gly Ile Phe Phe Lys Arg Gly Arg Lys Lys Leu
            405                 410                 415

Leu Tyr Ile Phe Lys Gln Pro Phe Met Arg Pro Val Gln Thr Thr Gln
            420                 425                 430

Glu Glu Asp Gly Cys Ser Cys Arg Phe Pro Glu Glu Glu Glu Gly Gly
            435                 440                 445

Cys Glu Leu Gly Gly Arg Val Lys Phe Ser Arg Ser Ala Asp Ala
450                 455                 460

Pro Ala Tyr Gln Gln Gly Gln Asn Gln Leu Tyr Asn Glu Leu Asn Leu
465                 470                 475                 480

Gly Arg Arg Glu Glu Tyr Asp Val Leu Asp Lys Arg Arg Gly Arg Asp
            485                 490                 495

Pro Glu Met Gly Gly Lys Pro Arg Arg Lys Asn Pro Gln Glu Gly Leu
            500                 505                 510

Tyr Asn Glu Leu Gln Lys Asp Lys Met Ala Glu Ala Tyr Ser Glu Ile
            515                 520                 525

Gly Met Lys Gly Glu Arg Arg Arg Gly Lys Gly His Asp Gly Leu Tyr
            530                 535                 540

Gln Gly Leu Ser Thr Ala Thr Lys Asp Thr Tyr Asp Ala Leu His Met
545                 550                 555                 560

Gln Ala Leu Pro Pro Arg
            565

<210> SEQ ID NO 27
<211> LENGTH: 671
<212> TYPE: PRT
<213> ORGANISM: Artificial Sequence
<220> FEATURE:
<223> OTHER INFORMATION: chimeric protein PSCAscFv-IgG4(EQ)-CD28tm-
      CD28gg-zeta, Figure 19

<400> SEQUENCE: 27

Met Leu Leu Leu Val Thr Ser Leu Leu Leu Cys Glu Leu Pro His Pro
1               5                   10                  15

Ala Phe Leu Leu Ile Pro Asp Ile Gln Leu Thr Gln Ser Pro Ser Thr
            20                  25                  30

Leu Ser Ala Ser Val Gly Asp Arg Val Thr Ile Thr Cys Ser Ala Ser
            35                  40                  45

Ser Ser Val Arg Phe Ile His Trp Tyr Gln Gln Lys Pro Gly Lys Ala
        50                  55                  60

Pro Lys Arg Leu Ile Tyr Asp Thr Ser Lys Leu Ala Ser Gly Val Pro
65                  70                  75                  80

Ser Arg Phe Ser Gly Ser Gly Ser Gly Thr Asp Phe Thr Leu Thr Ile
            85                  90                  95

Ser Ser Leu Gln Pro Glu Asp Phe Ala Thr Tyr Tyr Cys Gln Gln Trp
            100                 105                 110

Gly Ser Ser Pro Phe Thr Phe Gly Gln Gly Thr Lys Val Glu Ile Lys
            115                 120                 125
```

Gly Ser Thr Ser Gly Gly Gly Ser Gly Gly Gly Ser Gly Gly Gly Gly
            130                 135                 140

Ser Ser Glu Val Gln Leu Val Glu Tyr Gly Gly Leu Val Gln Pro
145                 150                 155                 160

Gly Gly Ser Leu Arg Leu Ser Cys Ala Ala Ser Gly Phe Asn Ile Lys
                165                 170                 175

Asp Tyr Tyr Ile His Trp Val Arg Gln Ala Pro Gly Lys Gly Leu Glu
            180                 185                 190

Trp Val Ala Trp Ile Asp Pro Glu Asn Gly Asp Thr Glu Phe Val Pro
        195                 200                 205

Lys Phe Gln Gly Arg Ala Thr Met Ser Ala Asp Thr Ser Lys Asn Thr
210                 215                 220

Ala Tyr Leu Gln Met Asn Ser Leu Arg Ala Glu Asp Thr Ala Val Tyr
225                 230                 235                 240

Tyr Cys Lys Thr Gly Gly Phe Trp Gly Gln Gly Thr Leu Val Thr Val
                245                 250                 255

Ser Ser Glu Ser Lys Tyr Gly Pro Pro Cys Pro Pro Cys Pro Ala Pro
            260                 265                 270

Glu Phe Glu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
290                 295                 300

Asp Val Ser Gln Glu Asp Pro Glu Val Gln Phe Asn Trp Tyr Val Asp
305                 310                 315                 320

Gly Val Glu Val His Asn Ala Lys Thr Lys Pro Arg Glu Glu Gln Phe
                325                 330                 335

Gln Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Gly Leu
        355                 360                 365

Pro Ser Ser Ile Glu Lys Thr Ile Ser Lys Ala Lys Gly Gln Pro Arg
370                 375                 380

Glu Pro Gln Val Tyr Thr Leu Pro Pro Ser Gln Glu Glu Met Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
        435                 440                 445

Arg Leu Thr Val Asp Lys Ser Arg Trp Gln Glu Gly Asn Val Phe Ser
450                 455                 460

Cys Ser Val Met His Glu Ala Leu His Asn His Tyr Thr Gln Lys Ser
465                 470                 475                 480

Leu Ser Leu Ser Leu Gly Lys Met Phe Trp Val Leu Val Val Val Gly
                485                 490                 495

Gly Val Leu Ala Cys Tyr Ser Leu Leu Val Thr Val Ala Phe Ile Ile
            500                 505                 510

Phe Trp Val Arg Ser Lys Arg Ser Arg Gly Gly His Ser Asp Tyr Met
        515                 520                 525

Asn Met Thr Pro Arg Arg Pro Gly Pro Thr Arg Lys His Tyr Gln Pro
530                 535                 540

Tyr Ala Pro Pro Arg Asp Phe Ala Ala Tyr Arg Ser Gly Gly Gly Arg
545                 550                 555                 560

Val Lys Phe Ser Arg Ser Ala Asp Ala Pro Ala Tyr Gln Gln Gly Gln
                565                 570                 575

Asn Gln Leu Tyr Asn Glu Leu Asn Leu Gly Arg Arg Glu Glu Tyr Asp
            580                 585                 590

Val Leu Asp Lys Arg Arg Gly Arg Asp Pro Glu Met Gly Gly Lys Pro
        595                 600                 605

Arg Arg Lys Asn Pro Gln Glu Gly Leu Tyr Asn Glu Leu Gln Lys Asp
610                 615                 620

Lys Met Ala Glu Ala Tyr Ser Glu Ile Gly Met Lys Gly Glu Arg Arg
625                 630                 635                 640

Arg Gly Lys Gly His Asp Gly Leu Tyr Gln Gly Leu Ser Thr Ala Thr
                645                 650                 655

Lys Asp Thr Tyr Asp Ala Leu His Met Gln Ala Leu Pro Pro Arg
            660                 665                 670

<210> SEQ ID NO 28
<211> LENGTH: 447
<212> TYPE: PRT
<213> ORGANISM: Artificial Sequence
<220> FEATURE:
<223> OTHER INFORMATION: chimeric protein sequence, Figure 20

<400> SEQUENCE: 28

Met Leu Leu Leu Val Thr Ser Leu Leu Leu Cys Glu Leu Pro His Pro
1               5                   10                  15

Ala Phe Leu Leu Ile Pro Asp Ile Gln Leu Thr Gln Ser Pro Ser Thr
            20                  25                  30

Leu Ser Ala Ser Val Gly Asp Arg Val Thr Ile Thr Cys Ser Ala Ser
        35                  40                  45

Ser Ser Val Arg Phe Ile His Trp Tyr Gln Gln Lys Pro Gly Lys Ala
    50                  55                  60

Pro Lys Arg Leu Ile Tyr Asp Thr Ser Lys Leu Ala Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Trp
            100                 105                 110

Gly Ser Ser Pro Phe Thr Phe Gly Gln Gly Thr Lys Val Glu Ile Lys
        115                 120                 125

Gly Ser Thr Ser Gly Gly Gly Ser Gly Gly Gly Ser Gly Gly Gly Gly
    130                 135                 140

Ser Ser Glu Val Gln Leu Val Glu Tyr Gly Gly Gly Leu Val Gln Pro
145                 150                 155                 160

Gly Gly Ser Leu Arg Leu Ser Cys Ala Ala Ser Gly Phe Asn Ile Lys
                165                 170                 175

Asp Tyr Tyr Ile His Trp Val Arg Gln Ala Pro Gly Lys Gly Leu Glu
            180                 185                 190

Trp Val Ala Trp Ile Asp Pro Glu Asn Gly Asp Thr Glu Phe Val Pro
        195                 200                 205

Lys Phe Gln Gly Arg Ala Thr Met Ser Ala Asp Thr Ser Lys Asn Thr
    210                 215                 220

Ala Tyr Leu Gln Met Asn Ser Leu Arg Ala Glu Asp Thr Ala Val Tyr
225                 230                 235                 240

-continued

Tyr Cys Lys Thr Gly Gly Phe Trp Gly Gln Gly Thr Leu Val Thr Val
                245                 250                 255

Ser Ser Gly Gly Gly Ser Ser Gly Gly Gly Ser Gly Met Ala Leu Ile
            260                 265                 270

Val Leu Gly Gly Val Ala Gly Leu Leu Leu Phe Ile Gly Leu Gly Ile
            275                 280                 285

Phe Phe Lys Arg Gly Arg Lys Lys Leu Leu Tyr Ile Phe Lys Gln Pro
    290                 295                 300

Phe Met Arg Pro Val Gln Thr Thr Gln Glu Glu Asp Gly Cys Ser Cys
305                 310                 315                 320

Arg Phe Pro Glu Glu Glu Glu Gly Gly Cys Glu Leu Gly Gly Gly Arg
                325                 330                 335

Val Lys Phe Ser Arg Ser Ala Asp Ala Pro Ala Tyr Gln Gln Gly Gln
            340                 345                 350

Asn Gln Leu Tyr Asn Glu Leu Asn Leu Gly Arg Arg Glu Glu Tyr Asp
            355                 360                 365

Val Leu Asp Lys Arg Arg Gly Arg Asp Pro Glu Met Gly Gly Lys Pro
    370                 375                 380

Arg Arg Lys Asn Pro Gln Glu Gly Leu Tyr Asn Glu Leu Gln Lys Asp
385                 390                 395                 400

Lys Met Ala Glu Ala Tyr Ser Glu Ile Gly Met Lys Gly Glu Arg Arg
                405                 410                 415

Arg Gly Lys Gly His Asp Gly Leu Tyr Gln Gly Leu Ser Thr Ala Thr
            420                 425                 430

Lys Asp Thr Tyr Asp Ala Leu His Met Gln Ala Leu Pro Pro Arg
            435                 440                 445

<210> SEQ ID NO 29
<211> LENGTH: 571
<212> TYPE: PRT
<213> ORGANISM: Artificial Sequence
<220> FEATURE:
<223> OTHER INFORMATION: chimeric protein sequence, Figure 21

<400> SEQUENCE: 29

Met Leu Leu Leu Val Thr Ser Leu Leu Leu Cys Glu Leu Pro His Pro
1               5                   10                  15

Ala Phe Leu Leu Ile Pro Asp Ile Gln Leu Thr Gln Ser Pro Ser Thr
            20                  25                  30

Leu Ser Ala Ser Val Gly Asp Arg Val Thr Ile Thr Cys Ser Ala Ser
        35                  40                  45

Ser Ser Val Arg Phe Ile His Trp Tyr Gln Gln Lys Pro Gly Lys Ala
    50                  55                  60

Pro Lys Arg Leu Ile Tyr Asp Thr Ser Lys Leu Ala Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Trp
            100                 105                 110

Gly Ser Ser Pro Phe Thr Phe Gly Gln Gly Thr Lys Val Glu Ile Lys
        115                 120                 125

Gly Ser Thr Ser Gly Gly Gly Ser Gly Gly Gly Ser Gly Gly Gly Gly
    130                 135                 140

Ser Ser Glu Val Gln Leu Val Glu Tyr Gly Gly Gly Leu Val Gln Pro
145                 150                 155                 160

-continued

```
Gly Gly Ser Leu Arg Leu Ser Cys Ala Ala Ser Gly Phe Asn Ile Lys
            165                 170                 175
Asp Tyr Tyr Ile His Trp Val Arg Gln Ala Pro Gly Lys Gly Leu Glu
        180                 185                 190
Trp Val Ala Trp Ile Asp Pro Glu Asn Gly Asp Thr Glu Phe Val Pro
    195                 200                 205
Lys Phe Gln Gly Arg Ala Thr Met Ser Ala Asp Thr Ser Lys Asn Thr
210                 215                 220
Ala Tyr Leu Gln Met Asn Ser Leu Arg Ala Glu Asp Thr Ala Val Tyr
225                 230                 235                 240
Tyr Cys Lys Thr Gly Gly Phe Trp Gly Gln Gly Thr Leu Val Thr Val
                245                 250                 255
Ser Ser Glu Ser Lys Tyr Gly Pro Pro Cys Pro Pro Cys Pro Gly Gly
            260                 265                 270
Gly Ser Ser Gly Gly Ser Gly Gly Gln Pro Arg Glu Pro Gln Val
        275                 280                 285
Tyr Thr Leu Pro Pro Ser Gln Glu Glu Met Thr Lys Asn Gln Val Ser
    290                 295                 300
Leu Thr Cys Leu Val Lys Gly Phe Tyr Pro Ser Asp Ile Ala Val Glu
305                 310                 315                 320
Trp Glu Ser Asn Gly Gln Pro Glu Asn Asn Tyr Lys Thr Thr Pro Pro
                325                 330                 335
Val Leu Asp Ser Asp Gly Ser Phe Phe Leu Tyr Ser Arg Leu Thr Val
            340                 345                 350
Asp Lys Ser Arg Trp Gln Glu Gly Asn Val Phe Ser Cys Ser Val Met
        355                 360                 365
His Glu Ala Leu His Asn His Tyr Thr Gln Lys Ser Leu Ser Leu Ser
    370                 375                 380
Leu Gly Lys Met Phe Trp Val Leu Val Val Gly Val Leu Ala
385                 390                 395                 400
Cys Tyr Ser Leu Leu Val Thr Val Ala Phe Ile Ile Phe Trp Val Arg
                405                 410                 415
Ser Lys Arg Ser Arg Gly Gly His Ser Asp Tyr Met Asn Met Thr Pro
            420                 425                 430
Arg Arg Pro Gly Pro Thr Arg Lys His Tyr Gln Pro Tyr Ala Pro Pro
        435                 440                 445
Arg Asp Phe Ala Ala Tyr Arg Ser Gly Gly Gly Arg Val Lys Phe Ser
    450                 455                 460
Arg Ser Ala Asp Ala Pro Ala Tyr Gln Gln Gly Gln Asn Gln Leu Tyr
465                 470                 475                 480
Asn Glu Leu Asn Leu Gly Arg Arg Glu Glu Tyr Asp Val Leu Asp Lys
                485                 490                 495
Arg Arg Gly Arg Asp Pro Glu Met Gly Gly Lys Pro Arg Arg Lys Asn
            500                 505                 510
Pro Gln Glu Gly Leu Tyr Asn Glu Leu Gln Lys Asp Lys Met Ala Glu
        515                 520                 525
Ala Tyr Ser Glu Ile Gly Met Lys Gly Glu Arg Arg Arg Gly Lys Gly
    530                 535                 540
His Asp Gly Leu Tyr Gln Gly Leu Ser Thr Ala Thr Lys Asp Thr Tyr
545                 550                 555                 560
Asp Ala Leu His Met Gln Ala Leu Pro Pro Arg
                565                 570
```

<210> SEQ ID NO 30
<211> LENGTH: 666
<212> TYPE: PRT
<213> ORGANISM: Artificial Sequence
<220> FEATURE:
<223> OTHER INFORMATION: chimeric protein PSCAscFv-IgG4(EQ)-CD4tm-4IBB-zeta, Figure 22

<400> SEQUENCE: 30

```
Met Leu Leu Leu Val Thr Ser Leu Leu Leu Cys Glu Leu Pro His Pro
1               5                   10                  15

Ala Phe Leu Leu Ile Pro Asp Ile Gln Leu Thr Gln Ser Pro Ser Thr
            20                  25                  30

Leu Ser Ala Ser Val Gly Asp Arg Val Thr Ile Thr Cys Ser Ala Ser
        35                  40                  45

Ser Ser Val Arg Phe Ile His Trp Tyr Gln Gln Lys Pro Gly Lys Ala
    50                  55                  60

Pro Lys Arg Leu Ile Tyr Asp Thr Ser Lys Leu Ala Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Trp
            100                 105                 110

Gly Ser Ser Pro Phe Thr Phe Gly Gln Gly Thr Lys Val Glu Ile Lys
        115                 120                 125

Gly Ser Thr Ser Gly Gly Gly Ser Gly Gly Ser Gly Gly Gly Gly
    130                 135                 140

Ser Ser Glu Val Gln Leu Val Glu Tyr Gly Gly Gly Leu Val Gln Pro
145                 150                 155                 160

Gly Gly Ser Leu Arg Leu Ser Cys Ala Ala Ser Gly Phe Asn Ile Lys
                165                 170                 175

Asp Tyr Tyr Ile His Trp Val Arg Gln Ala Pro Gly Lys Gly Leu Glu
            180                 185                 190

Trp Val Ala Trp Ile Asp Pro Glu Asn Gly Asp Thr Glu Phe Val Pro
        195                 200                 205

Lys Phe Gln Gly Arg Ala Thr Met Ser Ala Asp Thr Ser Lys Asn Thr
    210                 215                 220

Ala Tyr Leu Gln Met Asn Ser Leu Arg Ala Glu Asp Thr Ala Val Tyr
225                 230                 235                 240

Tyr Cys Lys Thr Gly Gly Phe Trp Gly Gln Gly Thr Leu Val Thr Val
                245                 250                 255

Ser Ser Glu Ser Lys Tyr Gly Pro Pro Cys Pro Pro Cys Pro Ala Pro
            260                 265                 270

Glu Phe Glu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser Gln Glu Asp Pro Glu Val Gln Phe Asn Trp Tyr Val Asp
305                 310                 315                 320

Gly Val Glu Val His Asn Ala Lys Thr Lys Pro Arg Glu Glu Gln Phe
                325                 330                 335

Gln Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Gly Leu
        355                 360                 365
```

-continued

```
Pro Ser Ser Ile Glu Lys Thr Ile Ser Lys Ala Lys Gly Gln Pro Arg
    370                 375                 380
Glu Pro Gln Val Tyr Thr Leu Pro Pro Ser Gln Glu Glu Met Thr Lys
385                 390                 395                 400
Asn Gln Val Ser Leu Thr Cys Leu Val Lys Gly Phe Tyr Pro Ser Asp
                405                 410                 415
Ile Ala Val Glu Trp Glu Ser Asn Gly Gln Pro Glu Asn Asn Tyr Lys
            420                 425                 430
Thr Thr Pro Pro Val Leu Asp Ser Asp Gly Ser Phe Phe Leu Tyr Ser
        435                 440                 445
Arg Leu Thr Val Asp Lys Ser Arg Trp Gln Glu Gly Asn Val Phe Ser
    450                 455                 460
Cys Ser Val Met His Glu Ala Leu His Asn His Tyr Thr Gln Lys Ser
465                 470                 475                 480
Leu Ser Leu Ser Leu Gly Lys Met Ala Leu Ile Val Leu Gly Gly Val
                485                 490                 495
Ala Gly Leu Leu Leu Phe Ile Gly Leu Gly Ile Phe Phe Lys Arg Gly
            500                 505                 510
Arg Lys Lys Leu Leu Tyr Ile Phe Lys Gln Pro Phe Met Arg Pro Val
        515                 520                 525
Gln Thr Thr Gln Glu Glu Asp Gly Cys Ser Cys Arg Phe Pro Glu Glu
    530                 535                 540
Glu Glu Gly Gly Cys Glu Leu Gly Gly Gly Arg Val Lys Phe Ser Arg
545                 550                 555                 560
Ser Ala Asp Ala Pro Ala Tyr Gln Gln Gly Gln Asn Gln Leu Tyr Asn
                565                 570                 575
Glu Leu Asn Leu Gly Arg Arg Glu Glu Tyr Asp Val Leu Asp Lys Arg
            580                 585                 590
Arg Gly Arg Asp Pro Glu Met Gly Gly Lys Pro Arg Arg Lys Asn Pro
        595                 600                 605
Gln Glu Gly Leu Tyr Asn Glu Leu Gln Lys Asp Lys Met Ala Glu Ala
    610                 615                 620
Tyr Ser Glu Ile Gly Met Lys Gly Glu Arg Arg Arg Gly Lys Gly His
625                 630                 635                 640
Asp Gly Leu Tyr Gln Gly Leu Ser Thr Ala Thr Lys Asp Thr Tyr Asp
                645                 650                 655
Ala Leu His Met Gln Ala Leu Pro Pro Arg
            660                 665

<210> SEQ ID NO 31
<211> LENGTH: 452
<212> TYPE: PRT
<213> ORGANISM: Artificial Sequence
<220> FEATURE:
<223> OTHER INFORMATION: chimeric protein PSCAscFv-L-CD28tm-4IBB-zeta,
      Figure 23

<400> SEQUENCE: 31

Met Leu Leu Leu Val Thr Ser Leu Leu Leu Cys Glu Leu Pro His Pro
1               5                   10                  15
Ala Phe Leu Leu Ile Pro Asp Ile Gln Leu Thr Gln Ser Pro Ser Thr
            20                  25                  30
Leu Ser Ala Ser Val Gly Asp Arg Val Thr Ile Thr Cys Ser Ala Ser
        35                  40                  45
Ser Ser Val Arg Phe Ile His Trp Tyr Gln Gln Lys Pro Gly Lys Ala
    50                  55                  60
```

```
Pro Lys Arg Leu Ile Tyr Asp Thr Ser Lys Leu Ala Ser Gly Val Pro
 65                  70                  75                  80

Ser Arg Phe Ser Gly Ser Gly Ser Gly Thr Asp Phe Thr Leu Thr Ile
             85                  90                  95

Ser Ser Leu Gln Pro Glu Asp Phe Ala Thr Tyr Tyr Cys Gln Gln Trp
            100                 105                 110

Gly Ser Ser Pro Phe Thr Phe Gly Gln Gly Thr Lys Val Glu Ile Lys
            115                 120                 125

Gly Ser Thr Ser Gly Gly Gly Ser Gly Gly Gly Ser Gly Gly Gly Gly
            130                 135                 140

Ser Ser Glu Val Gln Leu Val Glu Tyr Gly Gly Gly Leu Val Gln Pro
145                 150                 155                 160

Gly Gly Ser Leu Arg Leu Ser Cys Ala Ala Ser Gly Phe Asn Ile Lys
                165                 170                 175

Asp Tyr Tyr Ile His Trp Val Arg Gln Ala Pro Gly Lys Gly Leu Glu
            180                 185                 190

Trp Val Ala Trp Ile Asp Pro Glu Asn Gly Asp Thr Glu Phe Val Pro
            195                 200                 205

Lys Phe Gln Gly Arg Ala Thr Met Ser Ala Asp Thr Ser Lys Asn Thr
210                 215                 220

Ala Tyr Leu Gln Met Asn Ser Leu Arg Ala Glu Asp Thr Ala Val Tyr
225                 230                 235                 240

Tyr Cys Lys Thr Gly Gly Phe Trp Gly Gln Gly Thr Leu Val Thr Val
                245                 250                 255

Ser Ser Gly Gly Gly Ser Ser Gly Gly Ser Gly Met Phe Trp Val
                260                 265                 270

Leu Val Val Gly Gly Val Leu Ala Cys Tyr Ser Leu Leu Val Thr
            275                 280                 285

Val Ala Phe Ile Ile Phe Trp Val Arg Ser Lys Arg Ser Arg Gly Gly
290                 295                 300

His Ser Asp Tyr Met Asn Met Thr Pro Arg Arg Pro Gly Pro Thr Arg
305                 310                 315                 320

Lys His Tyr Gln Pro Tyr Ala Pro Pro Arg Asp Phe Ala Ala Tyr Arg
                325                 330                 335

Ser Gly Gly Gly Arg Val Lys Phe Ser Arg Ser Ala Asp Ala Pro Ala
            340                 345                 350

Tyr Gln Gln Gly Gln Asn Gln Leu Tyr Asn Glu Leu Asn Leu Gly Arg
            355                 360                 365

Arg Glu Glu Tyr Asp Val Leu Asp Lys Arg Arg Gly Arg Asp Pro Glu
            370                 375                 380

Met Gly Gly Lys Pro Arg Arg Lys Asn Pro Gln Glu Gly Leu Tyr Asn
385                 390                 395                 400

Glu Leu Gln Lys Asp Lys Met Ala Glu Ala Tyr Ser Glu Ile Gly Met
                405                 410                 415

Lys Gly Glu Arg Arg Arg Gly Lys Gly His Asp Gly Leu Tyr Gln Gly
            420                 425                 430

Leu Ser Thr Ala Thr Lys Asp Thr Tyr Asp Ala Leu His Met Gln Ala
            435                 440                 445

Leu Pro Pro Arg
450

<210> SEQ ID NO 32
<211> LENGTH: 544
```

```
<212> TYPE: PRT
<213> ORGANISM: Artificial Sequence
<220> FEATURE:
<223> OTHER INFORMATION: chimeric protein sequence, Figure 18 without
      signal

<400> SEQUENCE: 32
```

Asp Ile Gln Leu Thr Gln Ser Pro Ser Thr Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Gly Ser Ser Pro Phe Thr
                85                  90                  95

Phe Gly Gln Gly Thr Lys Val Glu Ile Lys Gly Ser Thr Ser Gly Gly
            100                 105                 110

Gly Ser Gly Gly Gly Ser Gly Gly Gly Ser Ser Glu Val Gln Leu
        115                 120                 125

Val Glu Tyr Gly Gly Gly Leu Val Gln Pro Gly Gly Ser Leu Arg Leu
130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190

Thr Met Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Lys Thr Gly Gly
210                 215                 220

Phe Trp Gly Gln Gly Thr Leu Val Thr Val Ser Ser Glu Ser Lys Tyr
225                 230                 235                 240

Gly Pro Pro Cys Pro Pro Cys Pro Gly Gly Ser Gly Gly Gly
                245                 250                 255

Ser Gly Gly Gln Pro Arg Glu Pro Gln Val Tyr Thr Leu Pro Pro Ser
            260                 265                 270

Gln Glu Glu Met Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
290                 295                 300

Pro Glu Asn Asn Tyr Lys Thr Thr Pro Pro Val Leu Asp Ser Asp Gly
305                 310                 315                 320

Ser Phe Phe Leu Tyr Ser Arg Leu Thr Val Asp Lys Ser Arg Trp Gln
                325                 330                 335

Glu Gly Asn Val Phe Ser Cys Ser Val Met His Glu Ala Leu His Asn
            340                 345                 350

His Tyr Thr Gln Lys Ser Leu Ser Leu Ser Leu Gly Lys Met Ala Leu
        355                 360                 365

Ile Val Leu Gly Gly Val Ala Gly Leu Leu Leu Phe Ile Gly Leu Gly
370                 375                 380

```
Ile Phe Phe Lys Arg Gly Arg Lys Lys Leu Leu Tyr Ile Phe Lys Gln
385                 390                 395                 400

Pro Phe Met Arg Pro Val Gln Thr Thr Gln Glu Glu Asp Gly Cys Ser
                405                 410                 415

Cys Arg Phe Pro Glu Glu Glu Glu Gly Gly Cys Glu Leu Gly Gly Gly
            420                 425                 430

Arg Val Lys Phe Ser Arg Ser Ala Asp Ala Pro Ala Tyr Gln Gln Gly
        435                 440                 445

Gln Asn Gln Leu Tyr Asn Glu Leu Asn Leu Gly Arg Arg Glu Glu Tyr
    450                 455                 460

Asp Val Leu Asp Lys Arg Arg Gly Arg Asp Pro Glu Met Gly Gly Lys
465                 470                 475                 480

Pro Arg Arg Lys Asn Pro Gln Glu Gly Leu Tyr Asn Glu Leu Gln Lys
                485                 490                 495

Asp Lys Met Ala Glu Ala Tyr Ser Glu Ile Gly Met Lys Gly Glu Arg
            500                 505                 510

Arg Arg Gly Lys Gly His Asp Gly Leu Tyr Gln Gly Leu Ser Thr Ala
        515                 520                 525

Thr Lys Asp Thr Tyr Asp Ala Leu His Met Gln Ala Leu Pro Pro Arg
    530                 535                 540
```

<210> SEQ ID NO 33
<211> LENGTH: 649
<212> TYPE: PRT
<213> ORGANISM: Artificial Sequence
<220> FEATURE:
<223> OTHER INFORMATION: chimeric protein PSCAscFv-IgG4(EQ)-CD28tm-
      CD28gg-zeta, Figure 19 without signal

<400> SEQUENCE: 33

```
Asp Ile Gln Leu Thr Gln Ser Pro Ser Thr Leu Ser Ala Ser Val Gly
1               5                   10                  15

Asp Arg Val Thr Ile Thr Cys Ser Ala Ser Ser Ser Val Arg Phe Ile
                20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Gly Ser Ser Pro Phe Thr
                85                  90                  95

Phe Gly Gln Gly Thr Lys Val Glu Ile Lys Gly Ser Thr Ser Gly Gly
            100                 105                 110

Gly Ser Gly Gly Gly Ser Gly Gly Gly Ser Ser Glu Val Gln Leu
        115                 120                 125

Val Glu Tyr Gly Gly Gly Leu Val Gln Pro Gly Gly Ser Leu Arg Leu
    130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190
```

-continued

Thr Met Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Lys Thr Gly Gly
    210                 215                 220

Phe Trp Gly Gln Gly Thr Leu Val Thr Val Ser Ser Glu Ser Lys Tyr
225                 230                 235                 240

Gly Pro Pro Cys Pro Pro Cys Pro Ala Pro Glu Phe Glu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Gln Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys Met Phe Trp Val Leu Val Val Val Gly Gly Val Leu Ala Cys Tyr
465                 470                 475                 480

Ser Leu Leu Val Thr Val Ala Phe Ile Ile Phe Trp Val Arg Ser Lys
                485                 490                 495

Arg Ser Arg Gly Gly His Ser Asp Tyr Met Asn Met Thr Pro Arg Arg
            500                 505                 510

Pro Gly Pro Thr Arg Lys His Tyr Gln Pro Tyr Ala Pro Pro Arg Asp
        515                 520                 525

Phe Ala Ala Tyr Arg Ser Gly Gly Gly Arg Val Lys Phe Ser Arg Ser
    530                 535                 540

Ala Asp Ala Pro Ala Tyr Gln Gln Gly Gln Asn Gln Leu Tyr Asn Glu
545                 550                 555                 560

Leu Asn Leu Gly Arg Arg Glu Glu Tyr Asp Val Leu Asp Lys Arg Arg
                565                 570                 575

Gly Arg Asp Pro Glu Met Gly Gly Lys Pro Arg Arg Lys Asn Pro Gln
            580                 585                 590

Glu Gly Leu Tyr Asn Glu Leu Gln Lys Asp Lys Met Ala Glu Ala Tyr
        595                 600                 605

```
Ser Glu Ile Gly Met Lys Gly Glu Arg Arg Gly Lys Gly His Asp
    610             615             620

Gly Leu Tyr Gln Gly Leu Ser Thr Ala Thr Lys Asp Thr Tyr Asp Ala
625             630             635             640

Leu His Met Gln Ala Leu Pro Pro Arg
                645

<210> SEQ ID NO 34
<211> LENGTH: 447
<212> TYPE: PRT
<213> ORGANISM: Artificial Sequence
<220> FEATURE:
<223> OTHER INFORMATION: chimeric protein sequence, Figure 20 without
      signal

<400> SEQUENCE: 34

Met Leu Leu Leu Val Thr Ser Leu Leu Cys Glu Leu Pro His Pro
1               5                   10                  15

Ala Phe Leu Leu Ile Pro Asp Ile Gln Leu Thr Gln Ser Pro Ser Thr
            20                  25                  30

Leu Ser Ala Ser Val Gly Asp Arg Val Thr Ile Thr Cys Ser Ala Ser
        35                  40                  45

Ser Ser Val Arg Phe Ile His Trp Tyr Gln Gln Lys Pro Gly Lys Ala
    50                  55                  60

Pro Lys Arg Leu Ile Tyr Asp Thr Ser Lys Leu Ala Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Trp
            100                 105                 110

Gly Ser Ser Pro Phe Thr Phe Gly Gln Gly Thr Lys Val Glu Ile Lys
        115                 120                 125

Gly Ser Thr Ser Gly Gly Gly Ser Gly Gly Gly Ser Gly Gly Gly Gly
    130                 135                 140

Ser Ser Glu Val Gln Leu Val Glu Tyr Gly Gly Gly Leu Val Gln Pro
145                 150                 155                 160

Gly Gly Ser Leu Arg Leu Ser Cys Ala Ala Ser Gly Phe Asn Ile Lys
                165                 170                 175

Asp Tyr Tyr Ile His Trp Val Arg Gln Ala Pro Gly Lys Gly Leu Glu
            180                 185                 190

Trp Val Ala Trp Ile Asp Pro Glu Asn Gly Asp Thr Glu Phe Val Pro
        195                 200                 205

Lys Phe Gln Gly Arg Ala Thr Met Ser Ala Asp Thr Ser Lys Asn Thr
    210                 215                 220

Ala Tyr Leu Gln Met Asn Ser Leu Arg Ala Glu Asp Thr Ala Val Tyr
225                 230                 235                 240

Tyr Cys Lys Thr Gly Gly Phe Trp Gly Gln Gly Thr Leu Val Thr Val
                245                 250                 255

Ser Ser Gly Gly Gly Ser Gly Gly Gly Ser Gly Met Ala Leu Ile
            260                 265                 270

Val Leu Gly Gly Val Ala Gly Leu Leu Leu Phe Ile Gly Leu Gly Ile
        275                 280                 285

Phe Phe Lys Arg Gly Arg Lys Lys Leu Leu Tyr Ile Phe Lys Gln Pro
    290                 295                 300

Phe Met Arg Pro Val Gln Thr Thr Gln Glu Glu Asp Gly Cys Ser Cys
305                 310                 315                 320
```

```
Arg Phe Pro Glu Glu Glu Gly Gly Cys Glu Leu Gly Gly Gly Arg
                325                 330                 335

Val Lys Phe Ser Arg Ser Ala Asp Ala Pro Ala Tyr Gln Gln Gly Gln
            340                 345                 350

Asn Gln Leu Tyr Asn Glu Leu Asn Leu Gly Arg Arg Glu Glu Tyr Asp
            355                 360                 365

Val Leu Asp Lys Arg Arg Gly Arg Asp Pro Glu Met Gly Gly Lys Pro
        370                 375                 380

Arg Arg Lys Asn Pro Gln Glu Gly Leu Tyr Asn Glu Leu Gln Lys Asp
385                 390                 395                 400

Lys Met Ala Glu Ala Tyr Ser Glu Ile Gly Met Lys Gly Glu Arg Arg
                405                 410                 415

Arg Gly Lys Gly His Asp Gly Leu Tyr Gln Gly Leu Ser Thr Ala Thr
            420                 425                 430

Lys Asp Thr Tyr Asp Ala Leu His Met Gln Ala Leu Pro Pro Arg
            435                 440                 445

<210> SEQ ID NO 35
<211> LENGTH: 549
<212> TYPE: PRT
<213> ORGANISM: Artificial Sequence
<220> FEATURE:
<223> OTHER INFORMATION: chimeric protein sequence, Figure 21 without
      signal

<400> SEQUENCE: 35

Asp Ile Gln Leu Thr Gln Ser Pro Ser Thr Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Gly Ser Ser Pro Phe Thr
                85                  90                  95

Phe Gly Gln Gly Thr Lys Val Glu Ile Lys Gly Ser Thr Ser Gly Gly
            100                 105                 110

Gly Ser Gly Gly Gly Ser Gly Gly Gly Ser Ser Glu Val Gln Leu
        115                 120                 125

Val Glu Tyr Gly Gly Gly Leu Val Gln Pro Gly Gly Ser Leu Arg Leu
    130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190

Thr Met Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Lys Thr Gly Gly
    210                 215                 220
```

Phe Trp Gly Gln Gly Thr Leu Val Thr Val Ser Ser Glu Ser Lys Tyr
225                 230                 235                 240

Gly Pro Pro Cys Pro Cys Pro Gly Gly Ser Ser Gly Gly Gly
            245                 250                 255

Ser Gly Gly Gln Pro Arg Glu Pro Gln Val Tyr Thr Leu Pro Pro Ser
            260                 265                 270

Gln Glu Glu Met Thr Lys Asn Gln Val Ser Leu Thr Cys Leu Val Lys
            275                 280                 285

Gly Phe Tyr Pro Ser Asp Ile Ala Val Glu Trp Glu Ser Asn Gly Gln
            290                 295                 300

Pro Glu Asn Asn Tyr Lys Thr Thr Pro Pro Val Leu Asp Ser Asp Gly
305                 310                 315                 320

Ser Phe Phe Leu Tyr Ser Arg Leu Thr Val Asp Lys Ser Arg Trp Gln
            325                 330                 335

Glu Gly Asn Val Phe Ser Cys Ser Val Met His Glu Ala Leu His Asn
            340                 345                 350

His Tyr Thr Gln Lys Ser Leu Ser Leu Ser Leu Gly Lys Met Phe Trp
            355                 360                 365

Val Leu Val Val Val Gly Gly Val Leu Ala Cys Tyr Ser Leu Leu Val
370                 375                 380

Thr Val Ala Phe Ile Ile Phe Trp Val Arg Ser Lys Arg Ser Arg Gly
385                 390                 395                 400

Gly His Ser Asp Tyr Met Asn Met Thr Pro Arg Arg Pro Gly Pro Thr
            405                 410                 415

Arg Lys His Tyr Gln Pro Tyr Ala Pro Pro Arg Asp Phe Ala Ala Tyr
            420                 425                 430

Arg Ser Gly Gly Gly Arg Val Lys Phe Ser Arg Ser Ala Asp Ala Pro
            435                 440                 445

Ala Tyr Gln Gln Gly Gln Asn Gln Leu Tyr Asn Glu Leu Asn Leu Gly
            450                 455                 460

Arg Arg Glu Glu Tyr Asp Val Leu Asp Lys Arg Arg Gly Arg Asp Pro
465                 470                 475                 480

Glu Met Gly Gly Lys Pro Arg Arg Lys Asn Pro Gln Glu Gly Leu Tyr
            485                 490                 495

Asn Glu Leu Gln Lys Asp Lys Met Ala Glu Ala Tyr Ser Glu Ile Gly
            500                 505                 510

Met Lys Gly Glu Arg Arg Arg Gly Lys Gly His Asp Gly Leu Tyr Gln
            515                 520                 525

Gly Leu Ser Thr Ala Thr Lys Asp Thr Tyr Asp Ala Leu His Met Gln
            530                 535                 540

Ala Leu Pro Pro Arg
545

<210> SEQ ID NO 36
<211> LENGTH: 644
<212> TYPE: PRT
<213> ORGANISM: Artificial Sequence
<220> FEATURE:
<223> OTHER INFORMATION: chimeric protein PSCAscFv-IgG4(EQ)-CD4tm-4IBB-
      zeta, Figure 22 without signal

<400> SEQUENCE: 36

Asp Ile Gln Leu Thr Gln Ser Pro Ser Thr Leu Ser Ala Ser Val Gly
1               5                   10                  15

```
Asp Arg Val Thr Ile Thr Cys Ser Ala Ser Ser Val Arg Phe Ile
             20                  25                  30

His Trp Tyr Gln Gln Lys Pro Gly Lys Ala Pro Lys Arg Leu Ile Tyr
             35                  40                  45

Asp Thr Ser Lys Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Gly Ser Ser Pro Phe Thr
                 85                  90                  95

Phe Gly Gln Gly Thr Lys Val Glu Ile Lys Gly Ser Thr Ser Gly Gly
                100                 105                 110

Gly Ser Gly Gly Gly Ser Gly Gly Gly Gly Ser Ser Glu Val Gln Leu
            115                 120                 125

Val Glu Tyr Gly Gly Gly Leu Val Gln Pro Gly Gly Ser Leu Arg Leu
130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
                180                 185                 190

Thr Met Ser Ala Asp Thr Ser Lys Asn Thr Ala Tyr Leu Gln Met Asn
            195                 200                 205

Ser Leu Arg Ala Glu Asp Thr Ala Val Tyr Tyr Cys Lys Thr Gly Gly
210                 215                 220

Phe Trp Gly Gln Gly Thr Leu Val Thr Val Ser Ser Glu Ser Lys Tyr
225                 230                 235                 240

Gly Pro Pro Cys Pro Pro Cys Pro Ala Pro Glu Phe Glu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
            275                 280                 285

Pro Glu Val Gln Phe Asn Trp Tyr Val Asp Gly Val Glu Val His Asn
290                 295                 300

Ala Lys Thr Lys Pro Arg Glu Glu Gln Phe Gln Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
                420                 425                 430
```

```
Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
    450                 455                 460

Lys Met Ala Leu Ile Val Leu Gly Gly Val Ala Gly Leu Leu Leu Phe
465                 470                 475                 480

Ile Gly Leu Gly Ile Phe Phe Lys Arg Gly Lys Lys Leu Leu Tyr
                485                 490                 495

Ile Phe Lys Gln Pro Phe Met Arg Pro Val Gln Thr Thr Gln Glu Glu
                500                 505                 510

Asp Gly Cys Ser Cys Arg Phe Pro Glu Glu Glu Glu Gly Cys Glu
                515                 520                 525

Leu Gly Gly Gly Arg Val Lys Phe Ser Arg Ser Ala Asp Ala Pro Ala
    530                 535                 540

Tyr Gln Gln Gly Gln Asn Gln Leu Tyr Asn Glu Leu Asn Leu Gly Arg
545                 550                 555                 560

Arg Glu Glu Tyr Asp Val Leu Asp Lys Arg Arg Gly Arg Asp Pro Glu
                565                 570                 575

Met Gly Gly Lys Pro Arg Arg Lys Asn Pro Gln Glu Gly Leu Tyr Asn
                580                 585                 590

Glu Leu Gln Lys Asp Lys Met Ala Glu Ala Tyr Ser Glu Ile Gly Met
            595                 600                 605

Lys Gly Glu Arg Arg Arg Gly Lys Gly His Asp Gly Leu Tyr Gln Gly
                610                 615                 620

Leu Ser Thr Ala Thr Lys Asp Thr Tyr Asp Ala Leu His Met Gln Ala
625                 630                 635                 640

Leu Pro Pro Arg

<210> SEQ ID NO 37
<211> LENGTH: 430
<212> TYPE: PRT
<213> ORGANISM: Artificial Sequence
<220> FEATURE:
<223> OTHER INFORMATION: chimeric protein PSCAscFv-L-CD28tm-4IBB-zeta,
      Figure 23 without signal

<400> SEQUENCE: 37

Asp Ile Gln Leu Thr Gln Ser Pro Ser Thr Leu Ser Ala Ser Val Gly
1               5                   10                  15

Asp Arg Val Thr Ile Thr Cys Ser Ala Ser Ser Ser Val Arg Phe Ile
                20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Pro Phe Thr
                85                  90                  95

Phe Gly Gln Gly Thr Lys Val Glu Ile Lys Gly Ser Thr Ser Gly Gly
            100                 105                 110

Gly Ser Gly Gly Gly Ser Gly Gly Gly Ser Ser Glu Val Gln Leu
        115                 120                 125

Val Glu Tyr Gly Gly Gly Leu Val Gln Pro Gly Gly Ser Leu Arg Leu
    130                 135                 140
```

```
Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
                180                 185                 190

Thr Met Ser Ala Asp Thr Ser Lys Asn Thr Ala Tyr Leu Gln Met Asn
            195                 200                 205

Ser Leu Arg Ala Glu Asp Thr Ala Val Tyr Tyr Cys Lys Thr Gly Gly
        210                 215                 220

Phe Trp Gly Gln Gly Thr Leu Val Thr Val Ser Ser Gly Gly Gly Ser
225                 230                 235                 240

Ser Gly Gly Gly Ser Gly Met Phe Trp Val Leu Val Val Val Gly Gly
                245                 250                 255

Val Leu Ala Cys Tyr Ser Leu Leu Val Thr Val Ala Phe Ile Ile Phe
            260                 265                 270

Trp Val Arg Ser Lys Arg Ser Arg Gly Gly His Ser Asp Tyr Met Asn
        275                 280                 285

Met Thr Pro Arg Arg Pro Gly Pro Thr Arg Lys His Tyr Gln Pro Tyr
    290                 295                 300

Ala Pro Pro Arg Asp Phe Ala Ala Tyr Arg Ser Gly Gly Gly Arg Val
305                 310                 315                 320

Lys Phe Ser Arg Ser Ala Asp Ala Pro Ala Tyr Gln Gln Gly Gln Asn
                325                 330                 335

Gln Leu Tyr Asn Glu Leu Asn Leu Gly Arg Arg Glu Glu Tyr Asp Val
            340                 345                 350

Leu Asp Lys Arg Arg Gly Arg Asp Pro Glu Met Gly Gly Lys Pro Arg
        355                 360                 365

Arg Lys Asn Pro Gln Glu Gly Leu Tyr Asn Glu Leu Gln Lys Asp Lys
    370                 375                 380

Met Ala Glu Ala Tyr Ser Glu Ile Gly Met Lys Gly Glu Arg Arg Arg
385                 390                 395                 400

Gly Lys Gly His Asp Gly Leu Tyr Gln Gly Leu Ser Thr Ala Thr Lys
                405                 410                 415

Asp Thr Tyr Asp Ala Leu His Met Gln Ala Leu Pro Pro Arg
            420                 425                 430

<210> SEQ ID NO 38
<211> LENGTH: 236
<212> TYPE: PRT
<213> ORGANISM: Artificial Sequence
<220> FEATURE:
<223> OTHER INFORMATION: an scFv directed against PSCA

<400> SEQUENCE: 38

Asp Ile Gln Leu Thr Gln Ser Pro Ser Thr Leu Ser Ala Ser Val Gly
1               5                   10                  15

Asp Arg Val Thr Ile Thr Cys Ser Ala Ser Ser Ser Val Arg Phe Ile
                20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80
```

```
Asp Phe Ala Thr Tyr Tyr Cys Gln Gln Trp Gly Ser Ser Pro Phe Thr
                85              90              95

Phe Gly Gln Gly Thr Lys Val Glu Ile Lys Gly Ser Ser Gly Gly
            100             105             110

Gly Ser Gly Gly Gly Ser Gly Gly Gly Ser Ser Glu Val Gln Leu
        115             120             125

Val Glu Tyr Gly Gly Gly Leu Val Gln Pro Gly Gly Ser Leu Arg Leu
    130             135             140

Ser Cys Ala Ala Ser Gly Phe Asn Ile Lys Asp Tyr Tyr Ile His Trp
145             150             155             160

Val Arg Gln Ala Pro Gly Lys Gly Leu Glu Trp Val Ala Trp Ile Asp
            165             170             175

Pro Glu Asn Gly Asp Thr Glu Phe Val Pro Lys Phe Gln Gly Arg Ala
            180             185             190

Thr Met Ser Ala Asp Thr Ser Lys Asn Thr Ala Tyr Leu Gln Met Asn
            195             200             205

Ser Leu Arg Ala Glu Asp Thr Ala Val Tyr Tyr Cys Lys Thr Gly Gly
        210             215             220

Phe Trp Gly Gln Gly Thr Leu Val Thr Val Ser Ser
225             230             235
```

CHIMERIC ANTIGEN RECEPTORS TARGETED TO PSCA

CROSS-REFERENCE TO RELATED APPLICATION

This application is a National Stage Application under 35 U.S.C. § 371 and claims the benefit of International Application No. PCT/US2016/055761, filed Oct. 6, 2016, which claims the benefit of U.S. Provisional Application No. 62/238,062, filed Oct. 6, 2015. The disclosure of the foregoing applications are hereby incorporated by reference in their entirety.

BACKGROUND

Prostate Cancer (PCa) is the third most common cancer type in the United States, with over 200,000 new cases projected to be diagnosed this year. In approximately 80% of PCa patients, tumor phenotype includes overexpression of prostate stem cell antigen (PSCA). Furthermore, PSCA is expressed on nearly 100% of bone metastatic prostate cancers, making it a theoretically attractive immunotherapeutic target. Recent clinical trials with CARs targeting CD19 for B-cell malignancies have demonstrated impressive results, yet replicating this success with other antigen targets remains elusive. Immunotherapy against solid tumors poses a more difficult tumor challenge due to the lack of such restricted antigen expression (i.e., CD19 for B cell malignancies) and the presence of an immunosuppressive microenvironment that can significantly hinder CAR efficacy. Importantly, there have been instances of on-target, off-tumor toxicity due to low levels of antigen expression on normal tissue.

While the basic components needed to create a CAR capable of binding to a desired target are reasonably well understood, it is challenging to design a CAR that has the qualities required for use in a safe and effective therapy. For example, it is important to avoid excessive activity against non-cancerous cells that express a low level of the target or do not express the target at all. Is also important to avoid eliciting a high level of cytokine production which can elicit undesirable off-tumor effects. Other factors that can impact therapeutic potential include, but are not limited to, the replicative capacity and life-span of the T cells expressing the CAR and the overall effector function of the T cells expressing the CAR required for a robust anti-tumor response.

SUMMARY

Described herein are chimeric transmembrane immunoreceptors (chimeric antigen receptors or "CARs") which comprise an extracellular domain, a transmembrane region and an intracellular signaling domain. The extracellular domain includes an scFv targeted against PSCA. The CAR described herein are useful for treating prostate cancer and prostate cancer bone metastasis.

In addition to an scFv target to PSCA, the extracelluar domain includes a spacer comprising, for example, a portion of the human IgG4 Fc domain. The transmembrane portion of the CAR includes, for example, a CD4 transmembrane domain, a CD8 transmembrane domain, a CD28 transmembrane domain, a CD3 transmembrane domain or a 4IBB transmembrane domain. The intracellular signaling domain includes the signaling domain from the zeta chain of the human CD3 complex (CD3ζ) and a costimulatory domain (e.g., the OX40, CD28, CD28gg or 4-1BB (CD137) costimulatory domain. The extracellular domain enables the CAR, when expressed on the surface of a T cell, to direct T cell activity to those cells expressing a PSCA. Such cells include prostate cancer cells. The inclusion of a costimulatory domain in series with (but not necessarily immediately adjacent to) CD3ζ in the intracellular region enables the T cell to receive co-stimulatory signals. T cells, for example, patient-specific, autologous T cells can be engineered to express the CARs described herein and the engineered cells can be expanded and used in ACT. Various T cell subsets can be used. In addition, the CAR can be expressed in other immune cells such as NK cells. Where a patient is treated with an immune cell expressing a CAR described herein the cell can be an autologous or allogenic T cell. In some cases, the cells used are CD4+ and CD8+ central memory T cells ($T_{CM}$), which are CD45RA-CD62L+, or $T_{CM/SCM/N}$ cells (CD45RA+CD62L+) and the use of such cells can improve long-term persistence of the cells after adoptive transfer compared to the use of other types of patient-specific T cells. Importantly, the overall design of the CAR avoids unwanted activity against non-cancerous cells, including non-cancerous cells expressing only a relatively low level of PSCA.

The PSCA scFv can include the sequence: DIQLTQSPSTLSASVGDRVTITCSASSSVRFIHWYQQ-KPGKAPKRLIYDTSKLASG VPSRFSGSGSGTDFTLTISSLQPEDFA-TYYCQQWGSSPFTFGQGTKVEIKGSTSGG GSGGGSGGGGSSEVQLVEYGGGLVQPGGSLRLS-CAASGFNIKDYYIHWVRQAPG KGLEWVAWIDPENGDTEFVPKFQGRATMSADTSKN-TAYLQMNSLRAEDTAVY YCKTGGFWGQGTLVTVSS (SEQ ID NO: 38) or a variant thereof having up to 5 amino acid substitutions (e.g., conservative substitutions).

Described herein is a nucleic acid molecule encoding a CAR comprising: an scFv directed against PSCA (e.g., SEQ ID NO:1) or a variant thereof having 1-5 (e.g., 1 or 2) amino acid modifications; a transmembrane domain selected from: a CD4 transmembrane domain or variant thereof having 1-10 (e.g., 1 or 2) amino acid modifications, a CD8 transmembrane domain or variant thereof having 1-5 (e.g., 1 or 2) amino acid modifications, a CD28 transmembrane domain or a variant thereof having 1-5 (e.g., 1 or 2) amino acid modifications, and a CD3ζ transmembrane domain or a variant thereof having 1-10 (e.g., 1 or 2) amino acid modifications; a costimulatory domain; and CD3ζ signaling domain of a variant thereof having 1-5 (e.g., 1 or 2) amino acid modifications. A spacer region is located between the scFv and the transmembrane domain. The spacer region, described in greater detail below, can include all or part of a human Fc region.

In some embodiments: nucleic acid molecule expresses a polypeptide comprising an amino acid sequence selected from SEQ ID NOs: 26-37; the chimeric antigen receptor comprises an amino acid sequence selected from SEQ ID NOs: 26-37 with 1-5 (e.g., 1 or 2) amino acid modifications (e.g., substitutions).

Also disclosed is a population of human T cells transduced by a vector comprising an expression cassette encoding a chimeric antigen receptor, wherein chimeric antigen receptor comprises an scFv directed to PSCA which includes a 4-1BB co-stimulatory domain. In various embodiments: the population of human T cells comprise a vector expressing a chimeric antigen receptor comprising an amino acid sequence selected from SEQ ID NOs: 26-37; the population of human T cells comprises of central memory T cells (T$_{CM}$) (e.g., at least 20%, 30%, 40%, 50% 60%, 70%, 80% of the cells are T$_{CM}$ cells; at least 15%, 20%, 25%, 30%, 35% of the T$_{CM}$ cells are CD4+ and at least 15%, 20%, 25%, 30%, 35% of the T$_{CM}$ cells are CD8+ cells).

Also described is a method of treating cancer in a patient comprising administering a population of autologous or allogeneic human T cells (e.g., autologous or allogenic T cells comprising T cells, e.g., at least 20%, 30%, 40%, 50% 60%, 70%, 80% of the cells are T$_{CM}$ cells; at least 15%, 20%, 25%, 30%, 35% of the T$_{CM}$ cells are CD4+ and at least 15%, 20%, 25%, 30%, 35% of the T$_{CM}$ cells are CD8+ cells) transduced by a vector comprising an expression cassette encoding a chimeric antigen receptor, wherein chimeric antigen receptor comprises an amino acid sequence selected from SEQ ID NOs: 26-37. In various embodiments: the population of human T cells comprise central memory T cells; the cancer is glioblastoma; and the transduced human T cells where prepared by a method comprising obtaining T cells from the patient, treating the T cells to isolate central memory T cells, and transducing at least a portion of the central memory cells to with a viral vector comprising an expression cassette encoding a chimeric antigen receptor, wherein chimeric antigen receptor comprises an amino acid sequence selected from SEQ ID NOs: 26-37.

Also described is: a nucleic acid molecule encoding an polypeptide comprising an amino acid sequence that is at least 95% identical to an amino acid sequence selected from SEQ ID NOs 26-37; a nucleic acid molecule encoding an polypeptide comprising an amino acid sequence that is identical to an amino acid sequence selected from SEQ ID NOs: 26-37 except for the presence of no more than 5 amino acid substitutions, deletions or insertions; a nucleic acid molecule encoding an polypeptide comprising an amino acid sequence that is identical to an amino acid sequence selected from SEQ ID NOs: 26-37 except for the presence of no more than 5 amino acid substitutions; and a nucleic acid molecule encoding an polypeptide comprising an amino acid sequence that is identical to an amino acid sequence selected from SEQ ID NOs: 26-37 except for the presence of no more than 2 amino acid substitutions.

T cells expressing a CAR targeted to PSCA can be useful in treatment of prostate cancer, including hormone refractory prostate cancer and metastases of prostate cancer, including bone liver, and lung metastases, as well as other cancers that express a PSCA, which include, but are not limited to pancreatic, bladder, colon, and glioblastoma (primary brain). Thus, this disclosure includes methods for treating cancer using T cells expressing a CAR described herein.

This disclosure also nucleic acid molecules that encode any of the CARs described herein (e.g., vectors that include a nucleic acid sequence encoding one of the CARs) and isolated T lymphocytes that express any of the CARs described herein.

The CAR described herein can include a spacer region located between the PSCA targeting domain (i.e., scFv recognizing PSCA or variant thereof) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
|---|---|---|
| a3 | 3 aa | AAA |
| linker | 10 aa | GGGSSGGGSG (SEQ ID NO: 2) |
| IgG4 hinge (S → P) (S228P) | 12 aa | ESKYGPPCP PCP (SEQ ID NO: 3) |
| IgG4 hinge | 12 aa | ESKYGPPCPSCP (SEQ ID NO: 4) |
| IgG4 hinge + linker | 22 aa | ESKYGPPCPPCPGGGSSGGGSG (SEQ ID NO: 5) |
| CD28 hinge | 39 aa | IEVMYPPPYLDNEKSNGTIIHVKGKHL CPSPLFPGPSKP (SEQ ID NO: 6) |
| CD8 hinge-48aa | 48 aa | AKPTTTPAPRPPTPAPTIASQPLSLRPE ACRPAAGGAVHTRGLDFACD (SEQ ID NO: 7) |
| CD8 hinge-45aa | 45 aa | TTTPAPRPPTPAPTIASQPLSLRPEACR PAAGGAVHTRGLDFACD (SEQ ID NO: 8) |
| IgG4 (HL-CH3) | 129 aa | ESKYGPPCPPCPGGGSSGGGSGGQPR EPQVYTLPPSQEEMTKNQVSLTCLVK GFYPSDIAVEWESNGQPENNYKTTPP VLDSDGSFFLYSRLTVDKSRWQEGNV FSCSVMHEALHNHYTQKSLSLSLGK (SEQ ID NO: 9) |
| IgG4 (S228P, L235E, N297Q) | 229 aa | ESKYGPPCPPCPAPEF EGGPSVFLFPP KPKDTLMISRTPEVTCVVVDVSQEDPE VQFNWYVDGVEVHNAKTKPREEQFQ STYRVVSVLTVLHQDWLNGKEYKCK VSNKGLPSSIEKTISKAKGQPREPQVY TLPPSQEEMTKNQVSLTCLVKGFYPS DIAVEWESNGQPENNYKTTPPVLDSD GSFFLYSRLTVDKSRWQEGNVFSCSV MHEALHNHYTQKSLSLSLGK (SEQ ID NO: 10) |
| IgG4 (CH3) | 107 aa | GQPREPQVYTLPPSQEEMTKNQVSLT CLVKGFYPSDIAVEWESNGQPENNYK TTPPVLDSDGSFFLYSRLTVDKSRWQ EGNVFSCSVMHEALHNHYTQKSLSLS LGK (SEQ ID NO: 12) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one ore more amino acid modifications, for example, 1, 2, 3, 4 or 5 substitutions, e.g., substitutions that reduce off-target binding.

An "amino acid modification" refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

In certain embodiments, the spacer is derived from an IgG1, IgG2, IgG3, or IgG4 that includes one or more amino acid residues substituted with an amino acid residue different from that present in an unmodified spacer. The one or more substituted amino acid residues are selected from, but not limited to one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof. In this numbering scheme, described in greater detail below, the first amino acid in the IgG4(L235E, N297Q) spacer in Table 1 is 219 and the first amino acid in the IgG4(HL-CH3) spacer in Table 1 is 219 as is the first amino acid in the IgG hinge sequence and the IgG4 hinge linker (HL) sequence in Table 1

In some embodiments, the modified spacer is derived from an IgG1, IgG2, IgG3, or IgG4 that includes, but is not limited to, one or more of the following amino acid residue substitutions: C220S, C226S, S228P, C229S, P230S, E233P, V234A, L234V, L234F, L234A, L235A, L235E, G236A, G237A, P238S, S239D, F243L, P247I, S267E, H268Q, S280H, K290S, K290E, K290N, R292P, N297A, N297Q, S298A, S298G, S298D, S298V, T299A, Y300L, V305I, V309L, E318A, K326A, K326W, K326E, L328F, A330L, A330S, A331S, P331S, I332E, E333A, E333S, E333S, K334A, A339D, A339Q, P396L, or a combination thereof.

In certain embodiments, the modified spacer is derived from IgG4 region that includes one or more amino acid residues substituted with an amino acid residue different from that present in an unmodified region. The one or more substituted amino acid residues are selected from, but not limited to, one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof.

In some embodiments, the modified spacer is derived from an IgG4 region that includes, but is not limited to, one or more of the following amino acid residue substitutions: 220S, 226S, 228P, 229S, 230S, 233P, 234A, 234V, 234F, 234A, 235A, 235E, 236A, 237A, 238S, 239D, 243L, 247I, 267E, 268Q, 280H, 290S, 290E, 290N, 292P, 297A, 297Q, 298A, 298G, 298D, 298V, 299A, 300L, 305I, 309L, 318A, 326A, 326W, 326E, 328F, 330L, 330S, 331S, 331S, 332E, 333A, 333S, 333S, 334A, 339D, 339Q, 396L, or a combination thereof, wherein the amino acid in the unmodified spacer is substituted with the above identified amino acids at the indicated position.

For amino acid positions in immunoglobulin discussed herein, numbering is according to the EU index or EU numbering scheme (Kabat et al. 1991 Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al. 1969 Proc Natl Acad Sci USA 63:78-85).

A variety of transmembrane domains can be used in the. Table 2 includes examples of suitable transmembrane domains. Where a spacer domain is present, the transmembrane domain is located carboxy terminal to the spacer domain.

TABLE 2

Examples of Transmembrane Domains

| Name | Accession | Length | Sequence |
|---|---|---|---|
| CD3z | J04132.1 | 21 aa | LCYLLDGILFIYGVILTALFL (SEQ ID NO: 13) |
| CD28 | NM_006139 | 27 aa | FWVLVVVGGVLACYSLLVTVAFI IFWV (SEQ ID NO: 14) |
| CD28(M) | NM_006139 | 28 aa | MFWVLVVVGGVLACYSLLVTVAF IIFWV (SEQ ID NO: 15) |
| CD4 | M35160 | 22 aa | MALIVLGGVAGLLLFIGLGIFF (SEQ ID NO: 16) |
| CD8tm | NM_001768 | 21 aa | IYIWAPLAGTCGVLLLSLVIT (SEQ ID NO: 17) |
| CD8tm2 | NM_001768 | 23 aa | IYIWAPLAGTCGVLLLSLVITLY (SEQ ID NO: 18) |
| CD8tm3 | NM_001768 | 24 aa | IYIWAPLAGTCGVLLLSLVITL YC (SEQ ID NO: 19) |
| 41BB | NM_001561 | 27 aa | IISFFLALTSTALLFLLFF LTLRFSVV (SEQ ID NO: 20) |

Many of the CAR described herein include one or more (e.g., two) costimulatory domains. The costimulatory domain(s) are located between the transmembrane domain and the CD3ζ signaling domain. Table 3 includes examples of suitable costimulatory domains together with the sequence of the CD3ζ signaling domain.

TABLE 3

CD3ζ Domain and Examples of Costimulatory Domains

| Name | Accession | Length | Sequence |
|---|---|---|---|
| CD3ζ | J04132.1 | 113 aa | RVKFSRSADAPAYQQGQNQLYNELN LGRREEYDVLDKRRGRDPEMGGKPR RKNPQEGLYNELQKDKMAEAYSEIG MKGERRRGKGHDGLYQGLSTATKDT YDALHMQALPPR (SEQ ID NO: 21) |
| CD28 | NM_006139 | 42 aa | RSKRSRLLHSDYMNMTPRRPGPTRK HYQPYAPPRDFAAYRS (SEQ ID NO: 22) |
| CD28gg* | NM_006139 | 42 aa | RSKRSRGGHSDYMNMTPRRPGPTR KHYQPYAPPRDFAAYRS (SEQ ID NO: 23) |
| 41BB | NM_001561 | 42 aa | KRGRKKLLYIFKQPFMRPVQTTQE EDGCSCRFPEEEEGGCEL (SEQ ID NO: 24) |

TABLE 3-continued

CD3ζ Domain and Examples of Costimulatory Domains

| Name | Accession | Length | Sequence |
|---|---|---|---|
| OX40 | | 42 aa | ALYLLRRDQRLPPDAHKPPGGGS FRTPIQEEQADAHSTLAKI (SEQ ID NO: 25) |

The PSCA-CAR used in the studies described herein are those summarized in Table 4 (immature, including GMCSFRa signal sequence) in which the spacer domain and costimulatory domain(s) for each CAR are indicated. All of these include the A11 PSCA scFv. The IgG4(HL-CH3) spacer is also referred to as the IgG4ΔCH2 spacer. The mature sequences (lacking GMCSFRa signal sequence) for SEQ ID NOs: 26, 27, 28, 29, 30, and 31 are SEQ ID NOs: 32, 33, 43, 35, 36, and 37.

TABLE 4

Examples of CAR Targeting PSCA

| Name | SEQ ID NO with signal/without signal | FIG. | Spacer | TM | Costimulatory Domain(s) |
|---|---|---|---|---|---|
| PSCAscFv-IgG4(HL-CH3-CD4tm-4IBB-zeta | 26/32 | 18 | IgG4(HL-CH3) (IgG4ΔCH2) | CD4 | 4-1BB |
| PSCAscFv-IgG4(EQ)-CD28tm-CD28gg-zeta | 27/33 | 19 | IgG4(EQ) | CD28 | CD28gg |
| PSCAscFv-L-CD4tm-4IBB-zeta | 28/34 | 20 | L | CD4 | 4-1BB |
| PSCAscFv-IgG4(HL-CH3)-CD28tm-CD28gg-zeta | 28/35 | 21 | IgG4(HL-CH3) (IgG4ΔCH2) | CD28 | CD28gg |
| PSCAscFv-IgG4(EQ)-CD4tm-4IBB-zeta | 30/36 | 22 | IgG4(EQ) | CD4 | 4-1BB |
| PSCAscFv-L-CD28tm-4IBB-zeta | 31/37 | 23 | L | CD28 | CD28gg |

DESCRIPTION OF DRAWINGS

FIG. 18: Amino acid sequence of PSCAscFv-IgG4(HL-CH3)-CD4tm-4IBB-zeta (SEQ ID NO:26).

FIG. 19: Amino acid sequence of PSCAscFv-IgG4(EQ)-CD28tm-CD28gg-zeta (SEQ ID NO:27).

FIG. 20: Amino acid sequence of PSCAscFv-L-CD4tm-4IBB-zeta (SEQ ID NO:28).

FIG. 21: Amino acid sequence of PSCAscFv-IgG4(HL-CH3)-CD28tm-CD28gg-zeta (SEQ ID NO:29).

FIG. 22: Amino acid sequence of PSCAscFv-IgG4(EQ)-CD4tm-4IBB-zeta (SEQ ID NO:30).

FIG. 23: Amino acid sequence of PSCAscFv-L-CD28tm-4IBB-zeta (SEQ ID NO:31).

DETAILED DESCRIPTION

Figure 1:
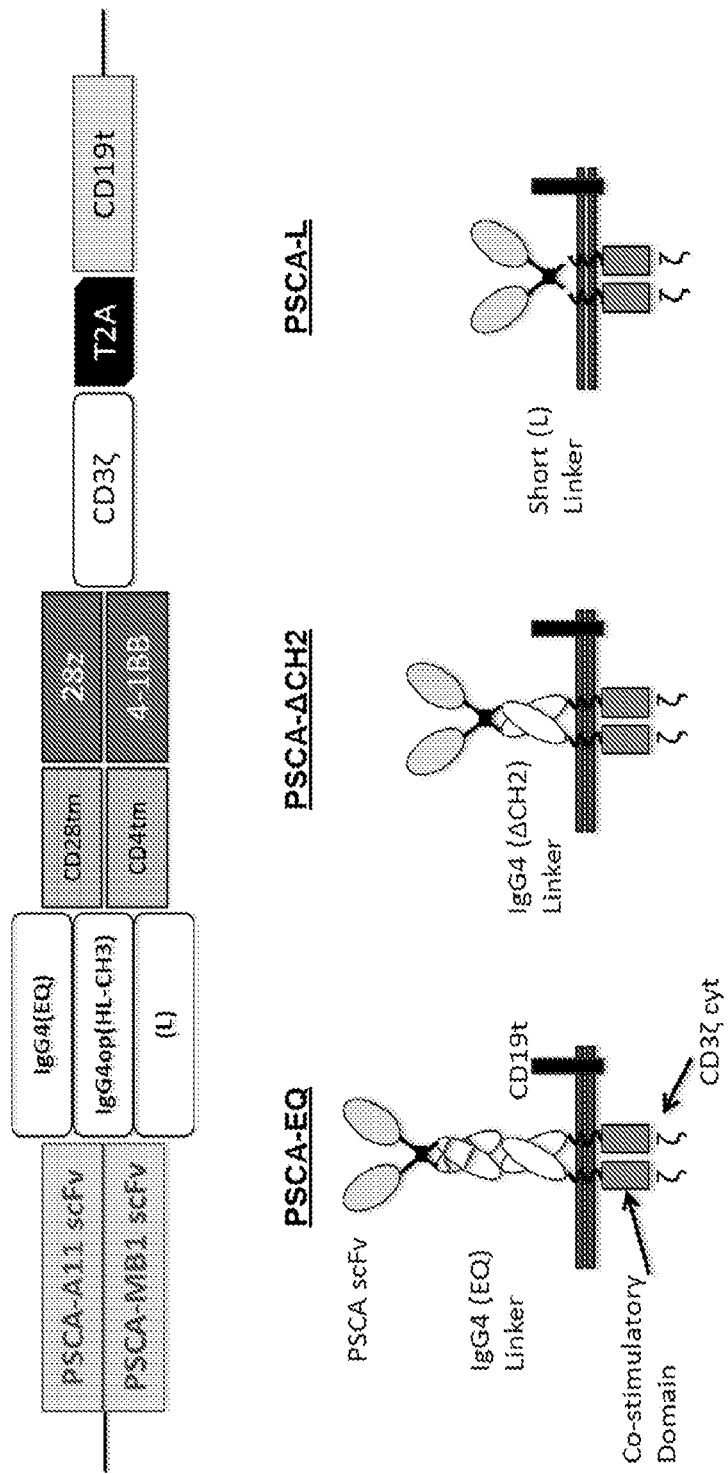
FIG. 1: Schematic diagram of CAR constructs with a variety of spacer regions (described in greater detail above) and having either: (a CD28 transmembrane domain and a CD28 co-stimulatory domain; or a CD4 transmembrane domain and a 4-1BB co-stimulatory domain. The constructs used a MB1 scFv or an A11 scFv. All constructs used a CD3ζ cytolytic domain. The T2A skip sequence separates the CAR from a truncated CD19 (CD19t) protein that is used to assess expression of the construct.

Described below is the structure, construction and characterization of various chimeric antigen receptors targeting PSCA. A chimeric antigen (CAR) is a recombinant biomolecule that contains, at a minimum, an extracellular recognition domain, a transmembrane region, and an intracellular signaling domain. The term "antigen," therefore, is not limited to molecules that bind antibodies, but to any molecule that can bind specifically to a target. For example, a CAR can include a ligand that specifically binds a cell surface receptor. The extracellular recognition domain (also referred to as the extracellular domain or simply by the recognition element which it contains) comprises a recognition element that specifically binds to a molecule present on the cell surface of a target cell. The transmembrane region anchors the CAR in the membrane. The intracellular signaling domain comprises the signaling domain from the zeta chain of the human CD3 complex and optionally comprises one or more costimulatory signaling domains. CARs can both to bind antigen and transduce T cell activation, independent of MHC restriction. Thus, CARs are "universal" immunoreceptors which can treat a population of patients with antigen-positive tumors irrespective of their HLA genotype. Adoptive immunotherapy using T lymphocytes that express a tumor-specific CAR can be a powerful therapeutic strategy for the treatment of cancer.

A wide variety of PSCA CAR we generated and tested in several assays to identify a CAR having appropriate activity and specificity while not eliciting excessive cytokine production.

In some cases, the CAR described herein can be produced using a vector in which the CAR open reading frame is followed by a T2A ribosome skip sequence and a truncated CD19 (CD19t), which lacks the cytoplasmic signaling tail (truncated at amino acid 323). In this arrangement, co-expression of CD19t provides an inert, non-immunogenic surface marker that allows for accurate measurement of gene modified cells, and enables positive selection of gene-modified cells, as well as efficient cell tracking and/or imaging of the therapeutic T cells in vivo following adoptive transfer. Co-expression of CD19t provides a marker for immunological targeting of the transduced cells in vivo using clinically available antibodies and/or immunotoxin reagents to selectively delete the therapeutic cells, and thereby functioning as a suicide switch.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various T cell subsets isolated from the patient, including unselected PBMC or enriched CD3 T cells or enriched CD3 or memory T cell subsets, can be transduced with a vector for CAR expression. Central memory T cells are one useful T cell subset. Central memory T cell can be isolated from peripheral blood mononuclear cells (PBMC) by selecting for CD45RO+/CD62L+ cells, using, for example, the Clini-MACS® device to immunomagnetically select cells expressing the desired receptors. The cells enriched for central memory T cells can be activated with anti-CD3/CD28, transduced with, for example, a SIN lentiviral vector that directs the expression of the CAR as well as a truncated human CD19 (CD19t), a non-immunogenic surface marker for both in vivo detection and potential ex vivo selection. The activated/genetically modified central memory T cells can be expanded in vitro with IL-2/IL-15 and then cryopreserved.

Example 1: Construction of CAR Targeting PSCA

FIG. 1 schematically depicts the elements in the open-reading frame of the expression vector used to express the various CAR (upper panel) and the resulting CAR (lower panel). The CAR used the MB1 scFv targeting PSCA. The A11 scFv was not used, but is a suitable alternative. Three different spacers were used: IgG4(EQ), which includes an IgG4 Fc region, including CH3, CH4 and hinge regions and has two amino acid substitutions that reduce binding to native Fc receptors; IgG4(HL-CH3), which is similar to IgG4(EQ), but lacks the CH2 domain and has a short linker sequence located between the hinge region and the CH3 region; and L, which is a short linker sequence. All three spacers are described in detail in Table 1. Two alternative transmembrane domains were used: CD4 and CD28, both described in greater detail in Table 2. Two alternative co-stimulation domains were used: CD28gg, a variant of the CD28 co-stimulatory domain and 4-IBB. Both are described in detail in Table 3. All of the CAR included the CD3ζ cytoplasmic signaling domain, also described in Table 3. The CAR coding sequences were followed by the T2A ribosomal skip sequence and a truncated CD17 sequence to permit co-expression of surface, signaling incompetent, truncated CD19 as a marker.

Figure 2:
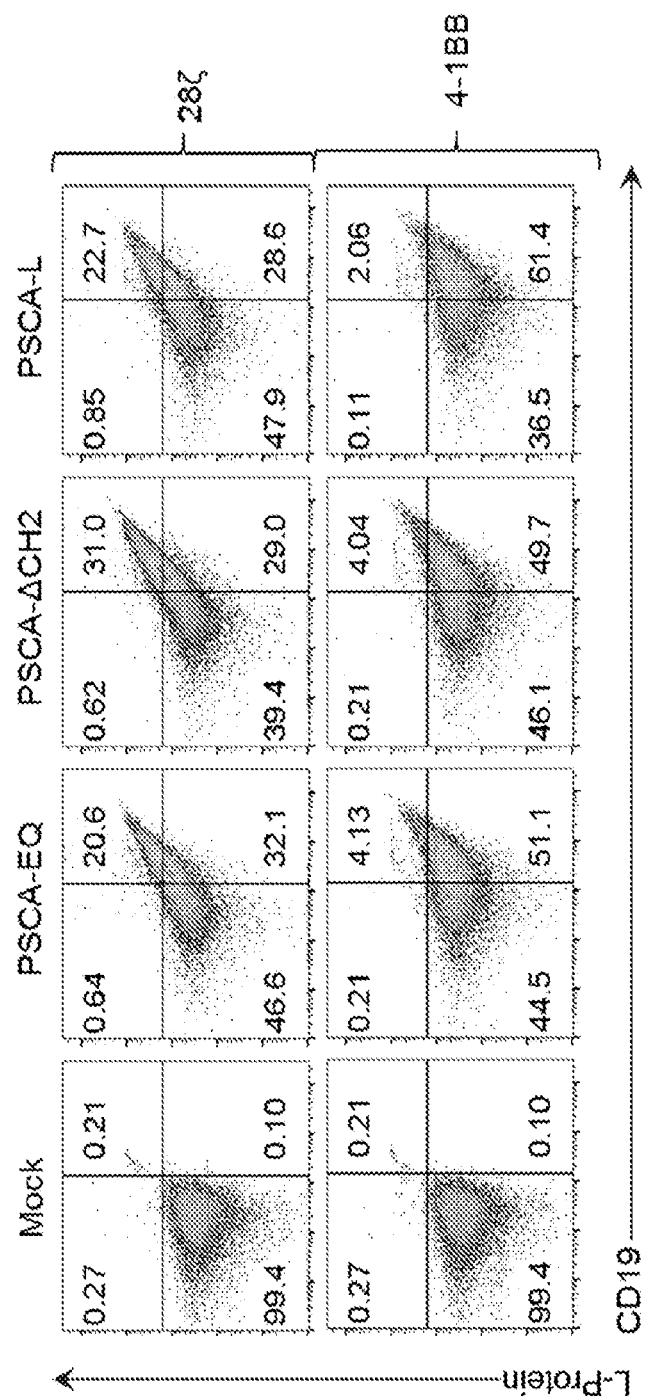
FIG. 2: Measurement of tCD19 and scFv (Protein L) expression data for the various constructs in FIG. 1.

Bulk central memory T cells that included CD4+ cells and CD8+ cells were transduced with lentivirus expressing one of six different CAR depicted in Table 4. Thus, the CAR included either a 4-IBB co-stimulatory domain (and a CD4 transmembrane domain) or a CD22gg co-stimulatory domain (and a CD28 transmembrane domain) and one of three different spacer domains: IgG4(EQ), IgG4(HL-CH3) or L (denoted as EQ, ΔCH2 or L in FIG. 2). FACS was performed to measure T cells expressing CD19 (CD19t) for detection of CAR and Protein L for detection of the scFv to determine stability. The results of this analysis are depicted in FIG. 2.

Example 2: PSCA Expressing Prostate Tumor Cells

Figure 3:
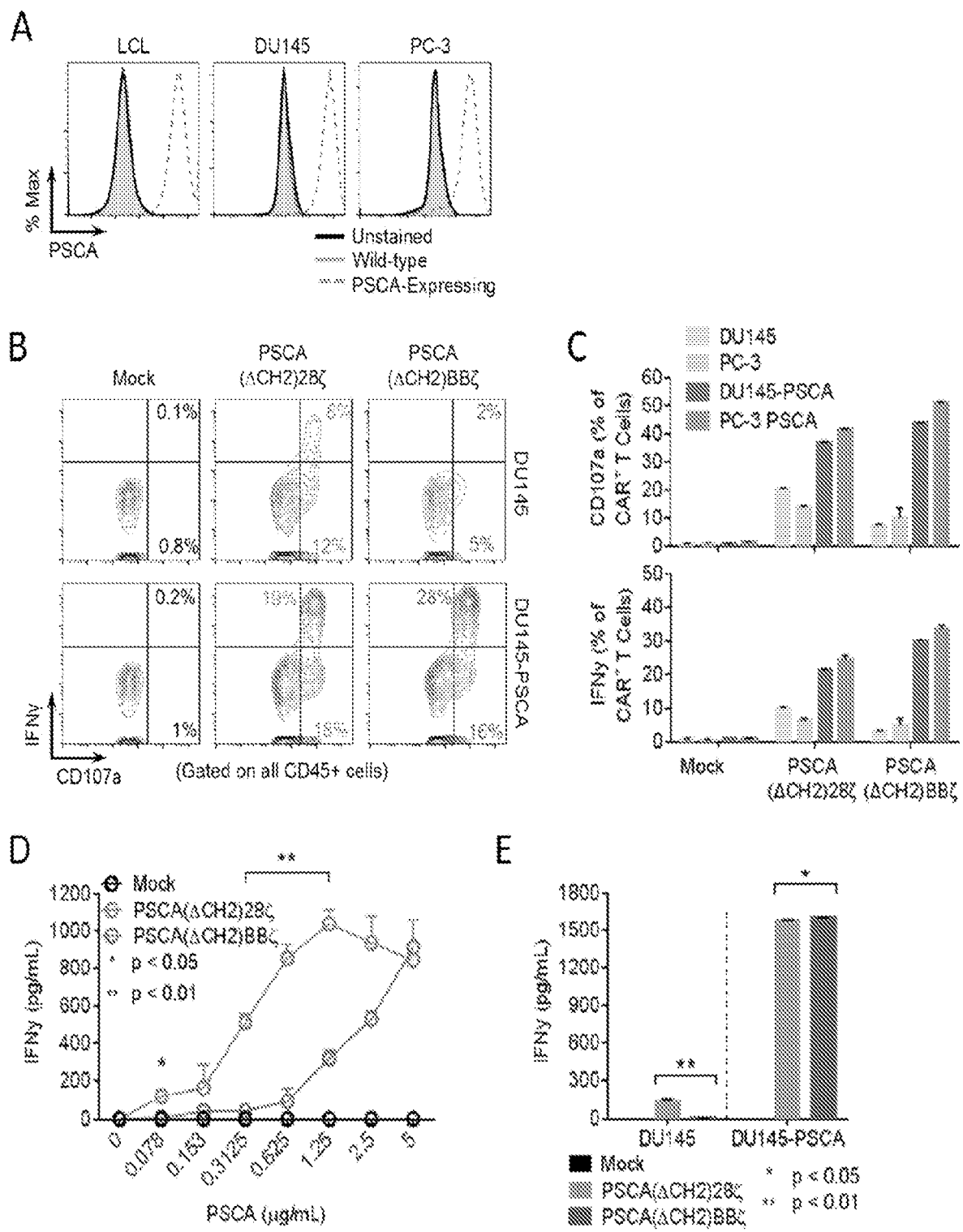
FIG. 3A-E: In vitro characterization of two different PSCA-CAR T cells against human prostate cancer cell lines. (A) Expression of PSCA in tumor cells engineered to express PSCA (LCL, PC-3, and DU145). (B-C) CD107a degranulation and IFNγ production in CAR T cells following a 5 h co-culture with tumor target, measured by flow cytometry. (D-E) IFNγ production by CAR T cells following a 24 h culture with recombinant PSCA protein or tumor targets, measured by ELISA.

Two different prostate cancer tumor cell lines, PC-3, and DU145, were engineered to express PSCA. FIG. 3A provides PSCA expression data for the parent cells and the engineer cells as well as LCL cells.

Example 3: INF-γ Production by Various PSCA-Targeted T Cells

Figure 4:
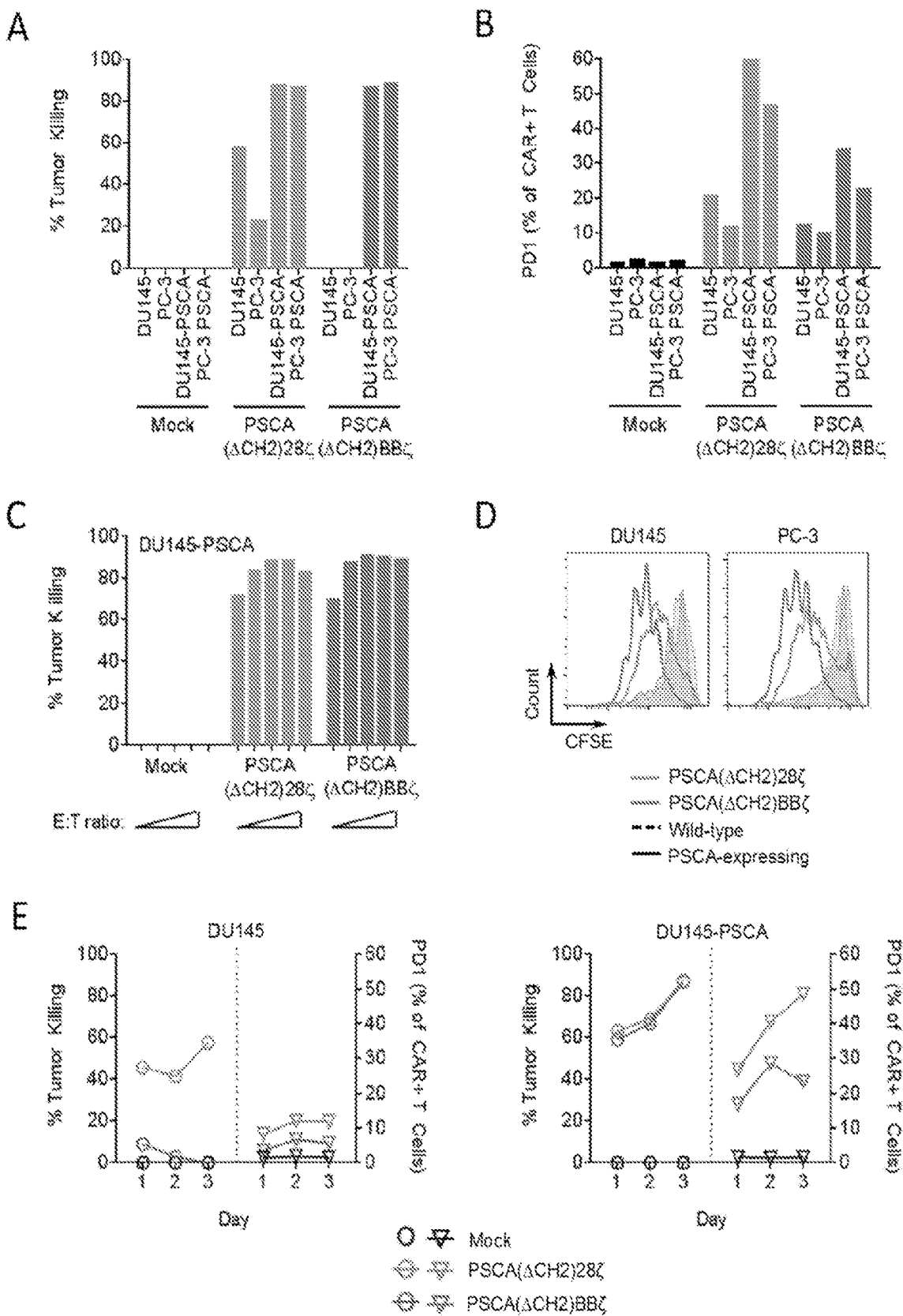
FIG. 4A-E: PSCA-CARs containing 4-1BB co-stimulatory domain demonstrate superior specificity, proliferation, and tumor cell killing capacity. Tumor killing (A) and PD-1 induction (B) in PSCA(ΔCH2)28z or PSCA(ΔCH2)BBz CAR T cells following a 72 h co-culture with tumor targets (DU145, PC-3, DU145-PSCA, and PC-3-PSCA) measured by flow cytometry. (C) Tumor killing with Effector:Tumor (E:T) ratio from 0.25:1-4:1. (D) CFSE proliferation of CAR T cells following a 72 h co-culture with tumor targets. (E) Kinetics of tumor killing and PD-1 induction in CAR T cells following a 1, 2 or 3 day co-culture with tumor targets (DU145, left; DU145-PSCA, right).

FIGS. 3B-E provide IFNγ production data and CD107a degranulation data for the two different CAR following a 5 h co-culture with tumor target (DU145 cells, PC3 cells, DU145 cells transfected with a PSCA expression vector or PC3 cells transfected with a PSCA expression vector), as measured by flow cytometry. FIGS. 4D-E provide data for IFNγ production by the CAR T cells following a 24 h culture with recombinant PSCA protein or tumor targets, measured by ELISA. Here too it can be seen that CAR with a 4-IBB co-stimulatory domain produce less IFNγ and lower levels of degranulation marker than CAR with a CD28 co-stimulatory domain.

This assessment of degranulation and intracellular IFN-γ production revealed that all CAR that include a CD22gg co-stimulatory domain exhibit non-specific activity against wild-type DU145 cells and wild-type PC3 cells, while CARs that include a 4-IBB co-stimulatory domain exhibit far less non-specific activity. In addition, CAR that include a CD22gg co-stimulatory domain produce more cytokine overall than CARs that include a 4-IBB co-stimulatory domain.

Example 4: Cell Killing by Various CAR

A comparison of a CAR having a CD28 co-stimulatory domain and a CAR having a 4-IBB co-stimulatory domain (described in FIG. 3A) demonstrated that PSCA-CARs containing 4-1BB co-stimulatory domain demonstrate superior specificity, proliferation, and tumor cell killing capacity. The results of this analysis are shown in FIG. 4A-E. Tumor killing was more specific for CAR having a 4-IBB co-stimulatory domain than a CD28 co-stimulatory domain as shown by the lower killing of cells not transfected with a PSCA expression construct (FIG. 4A). The CAR having a 4-IBB also exhibited lower levels of PD-1 induction (FIG. 4B). Killing and PD-1 induction was measured following a 72 h co-culture with tumor targets (DU145, PC-3, DU145-PSCA, and PC-3-PSCA. FIG. 4C shows the results of an analysis of tumor killing with Effector:Tumor (E:T) ratios from 0.25:1-4:1. FIG. 4D depicts the results of an analysis of proliferation of CAR T cells following a 72 h co-culture with tumor targets and FIG. 4E shows the kinetics of tumor killing and PD-1 induction in CAR T cells following a 1, 2 or 3 day co-culture with tumor targets (DU145, left; DU145-PSCA, right).

Example 5: Impact of Spacer on CAR Function

Figure 5:
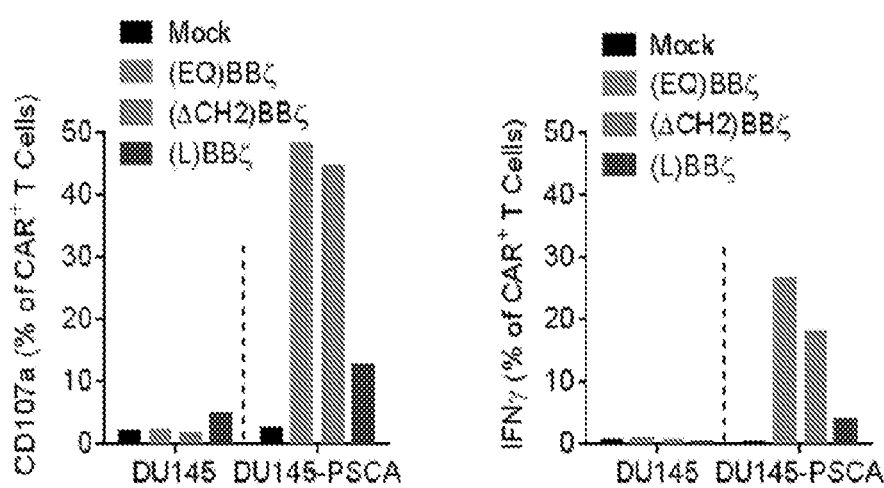
FIGS. 5A-B: Extracellular spacer dictates in vitro PSCA-CAR functionality. (A) CD107a degranulation and IFNγ production in PSCA(EQ)BBz, PSCA(ΔCH2)BBz, and PSCA(L)BBz CAR T cells following a 5 h co-culture with tumor targets (DU145 and DU145-PSCA), measured by flow cytometry. (B) IFNγ in CAR T cells following a 24 h culture with recombinant PSCA protein or tumor targets, measured by ELISA.
Figure 5:
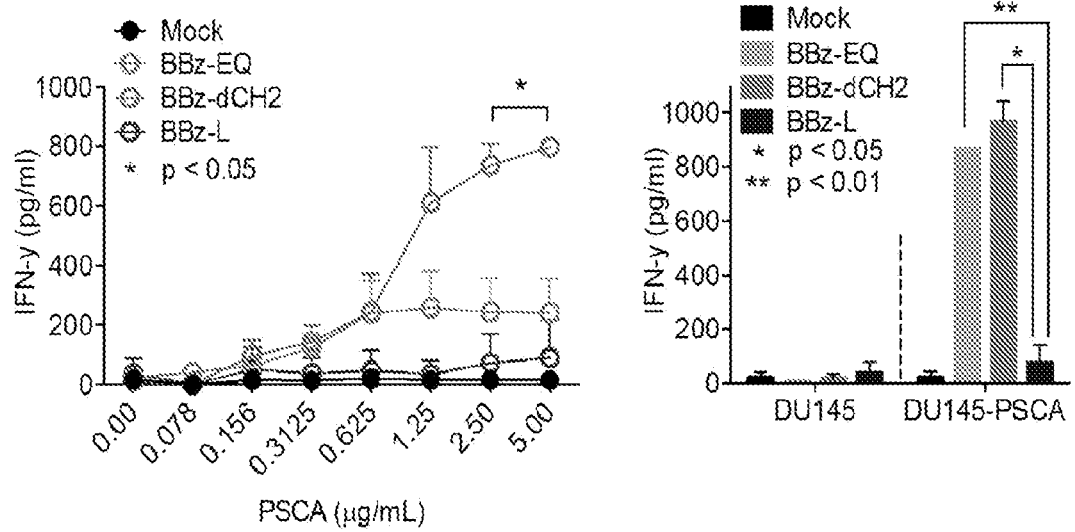

The studies depicted in FIG. 5A-B show that the spacer region can impact CD107a expression (degranulation) and IFN-γ production. The CAR here all include a CD4 transmembrane domain and a 4-IBB co-stimulatory domain.

Figure 6:
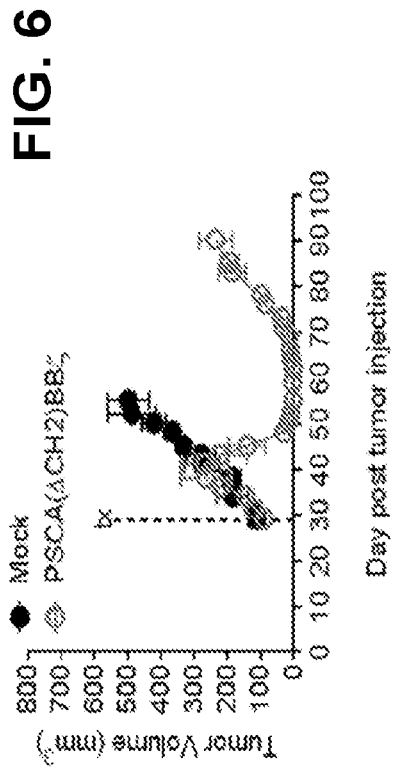
FIG. 6A-D: PSCA-CAR T cells demonstrate potent anti-tumor efficacy in prostate cancer xenograft and orthotopic models. (A) PC-3-PSCA ($2\times10^6$) cells were injected subcutaneously in NSG male mice, and when tumors reached ~30-50 mm3, CAR Tcm ($5\times10^6$) were injected intratumorally, and tumor growth was monitored by caliper measurements. (B) DU145-PSCA ($2\times10^6$) cells were injected subcutaneously in NSG males, and CAR PBMC cells ($5\times10^6$) cells were intravenously delivered. (C) PC-3-PSCA ($2\times10^5$) cells were injected intratibially in NSG males, and CAR PBMC cells ($2\times10^6$ or $5\times10^6$) were intravenously delivered. (D) CAR T cell persistence in blood at 58 days post tumor injection in each group.
Figure 6:
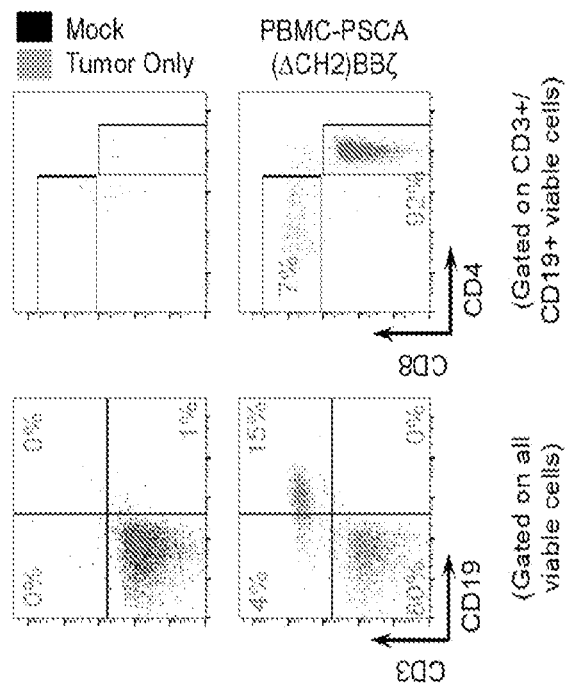
Figure 6:
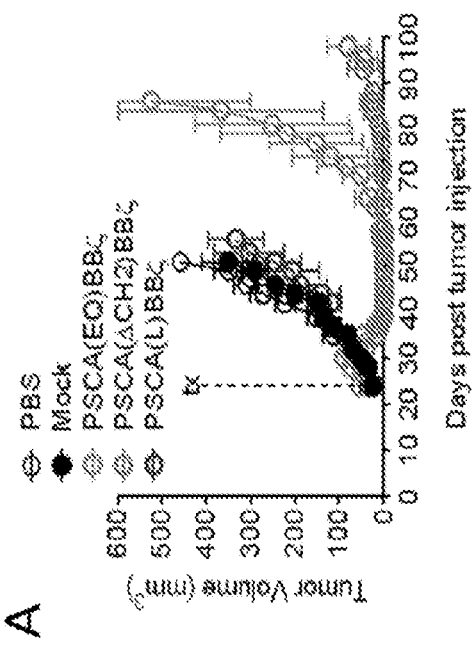
Figure 6:
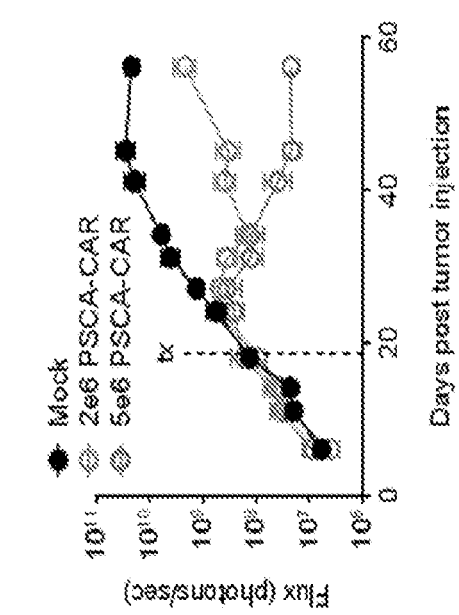

Example 6: Anti-Tumor Efficiency in Prostate Cancer Xenograft and Orthotopic Models Two PSCA-CAR T described above demonstrate potent anti-tumor efficacy in prostate cancer xenograft and orthotopic models. PC-3-PSCA ($2 \times 10^6$) cells were injected subcutaneously in NSG male mice, and when tumors reached ~30-50 mm$^3$, CAR Tcm ($5 \times 10^6$) were injected intratumorally, and tumor growth was monitored by caliper measurements (FIG. 6A). DU145-PSCA ($2 \times 10^6$) cells were injected subcutaneously in NSG males, and CAR PBMC cells ($5 \times 10^6$) cells were intravenously delivered (FIG. 6B). To create an orthotopic model, PC-3-PSCA ($2 \times 10^5$) cells were injected intratibially in NSG males, and CAR PBMC cells ($2 \times 10^6$ or $5 \times 10^6$) were intravenously delivered (FIG. 6C). CR T cell persistence in blood at 58 days post tumor injection in each group from Panel B was assessed (FIG. 6D).

Figure 7:
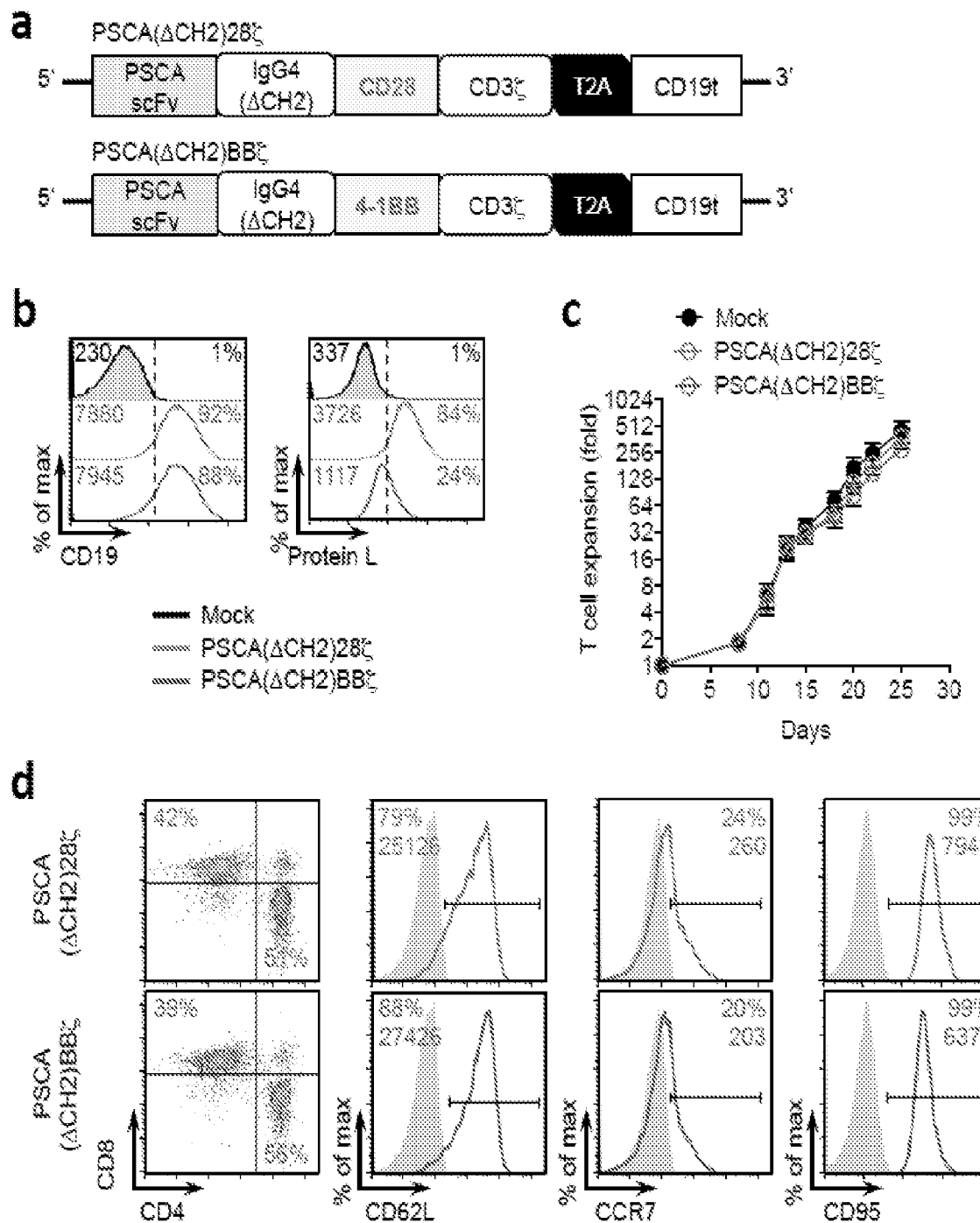
FIG. 7A-D: PSCA-CAR T cells containing CD28 or 4-1BB co-stimulatory domains. (A) Diagram of the lentiviral expression cassette with PSCA-CARs containing the humanized scFv (A11 clone) targeting PSCA, with a 129 amino acid modified human IgG4 Fc linker (void of the CH2 domain, ΔCH2), a transmembrane domain (either CD28 or CD4), a cytoplasmic CD28 or 4-1BB costimulatory domain, and a cytolytic CD3z domain. A truncated non-signaling CD19 (CD19t) is separated from the CAR with a T2A ribosomal skip sequence for tracking CAR-expressing cells. (B) Mock (untransduced), PSCA(ΔCH2)28ζ, or PSCA (ΔCH2)BBζ CAR T cells were evaluated by flow cytometry for CD19t expression to detect lentiviral transduction of CARs (top) or Protein L to detect the scFv (bottom). (C) Ex vivo expansion kinetics for Mock and PSCA-CAR T cells over 25 days in culture. (D) Cell-surface expression of indicated cell-surface markers of PSCA-CAR T cells at end of ex vivo expansion as determined by flow cytometry. All data are representative of at least two independent experiments.
Figure 12:
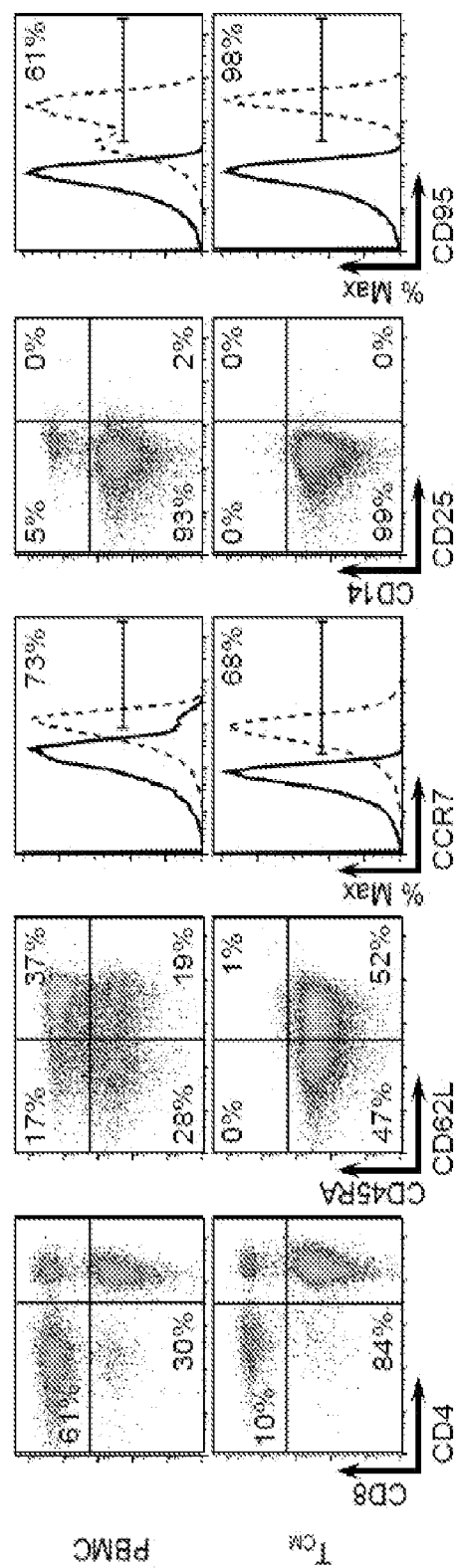
FIG. 12 Cell-surface phenotypes of PBMC and $T_{CM}$ populations. (a) Starting populations of PBMC and TCM were analyzed by flow cytometry for expression of CD4, CD8, CD45RA, CD62L, CCR7, CD14, CD25, and CD95. Representative FACS plots are shown.

Example 7: PSCA-Targeted CAR Containing 4-1BB Domain Shows Superior Selectivity and Reduce T Cell Exhaustion Compared with a CD28 Domain Two PSCA-CAR constructs that include the humanized PSCA scFv derived from 1G8 (A11 clone) [Lepin et al. 2010 *Eur J Nucl Med Mol Imaging* 37:529), the ΔCH2 extracellular spacer, the CD3ζ cytolytic domain, and the CD19t cell tracker and differ only in their co-stimulatory domain (4-1BB versus CD28 were compared (FIG. 7A). This Example and Examples 8-11 describe studies using PSCA-CARs engineered in PBMC-derived T cells, unless otherwise indicated. For example, central memory T cells ($T_{CM}$)), which have a different starting cell-surface T cell phenotype were used in some studies (FIG. 12).

Both PSCA-CARs were stably expressed (FIG. 7B) as determined by flow cytometric detection of scFv and CD19t, albeit at lower levels for PSCA(ΔCH2)BBζ compared to PSCA(ΔCH2)28ζ. These CAR T cells exhibited comparable ex vivo T cell expansion kinetics (FIG. 7C) and similar cell-surface T cell phenotypes (FIG. 7D).

Figure 8:
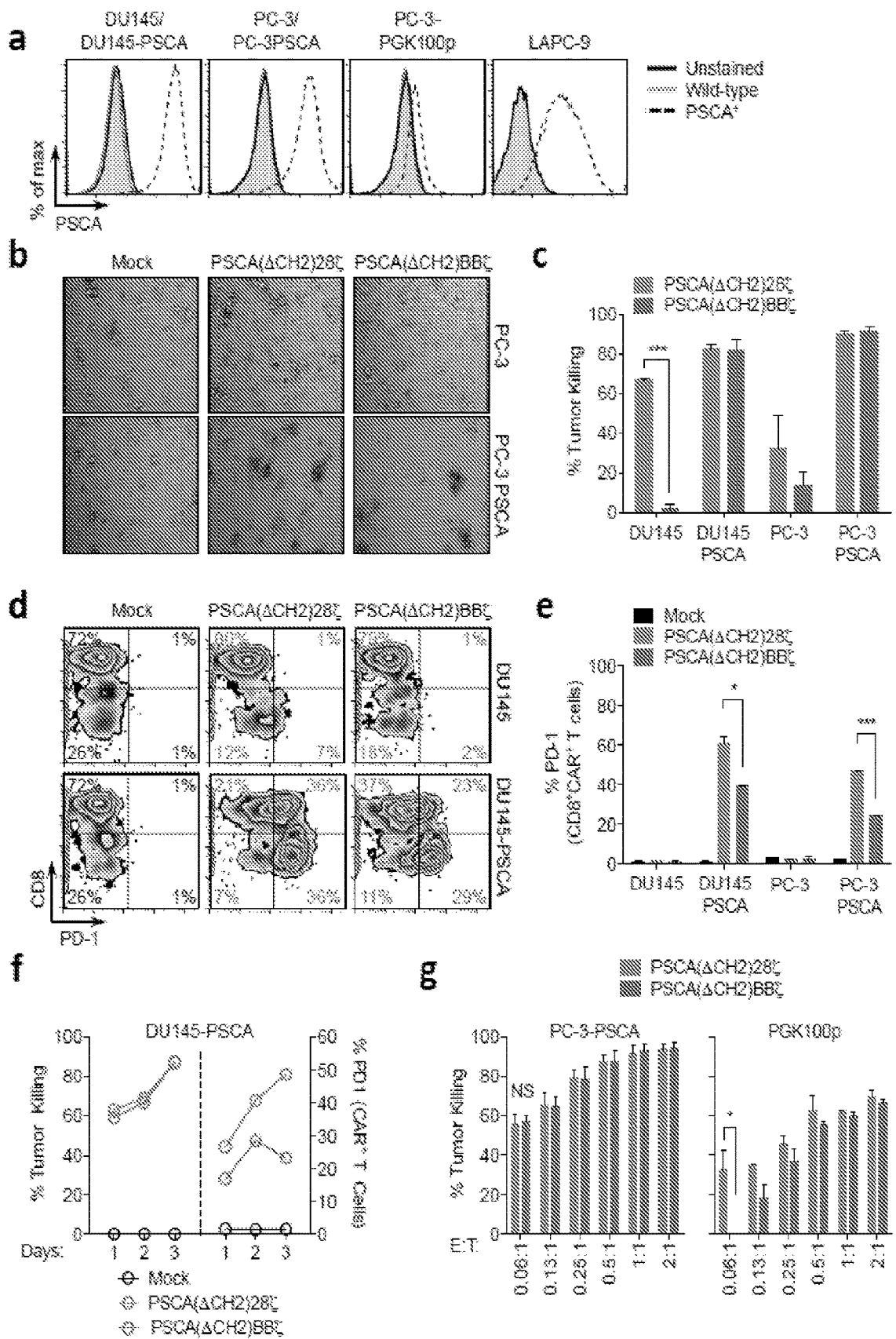
FIG. 8A-G: PSCA-CARs containing a 4-1BB co-stimulatory domain show superior tumor targeting compared with CD28 co-stimulation in PSCA-CARs in vitro. (A) Histograms of PSCA expression in human prostate cancer cell lines, determined by flow cytometry. DU145 and PC-3 cell lines were lentivirally transduced to over-express human PSCA under the control of the EF1α promoter (see materials and methods). PC-3-PGK100p cell line was generated by expressing human PSCA under the control of the indicated mutant PGK promoter. LAPC-9 cells endogenously express human PSCA. (B) Snapshot images of a tumor killing assay comparing Mock, PSCA(ΔCH2)2ζ, or PSCA(ΔCH2)BBζ CAR T cells at a 1:1 effector:target ratio, assessed by light microscopy following a 3-day co-culture with PC-3 or PC-3-PSCA tumor cells. (C) Similar tumor killing assay as in (B), assessed by flow cytometry following a 3-day co-culture with indicated tumor targets. (D) Representative zebra plots of PD-1 expression in PSCA-CAR T cells following a 3-day co-culture with indicated tumor targets. (E) Quantification of PD-1 expression in CD8+ CAR+ T cells following a 3-day co-culture with indicated tumor targets. (F) Tumor killing assay comparing PSCA-CAR T cells at 1, 2 or 3-days of co-culture with DU145. PD-1 expression in T cells compared to T cells cultured without tumor targets. (G) Tumor killing assay with different effector:target ratios, assessed by flow cytometry following a 3-day co-culture with PC-3-PSCA or PC-3-PGK100p. Data are shown as n=2 per group±SD. All data are representative of at least two independent experiments.
Figure 13:
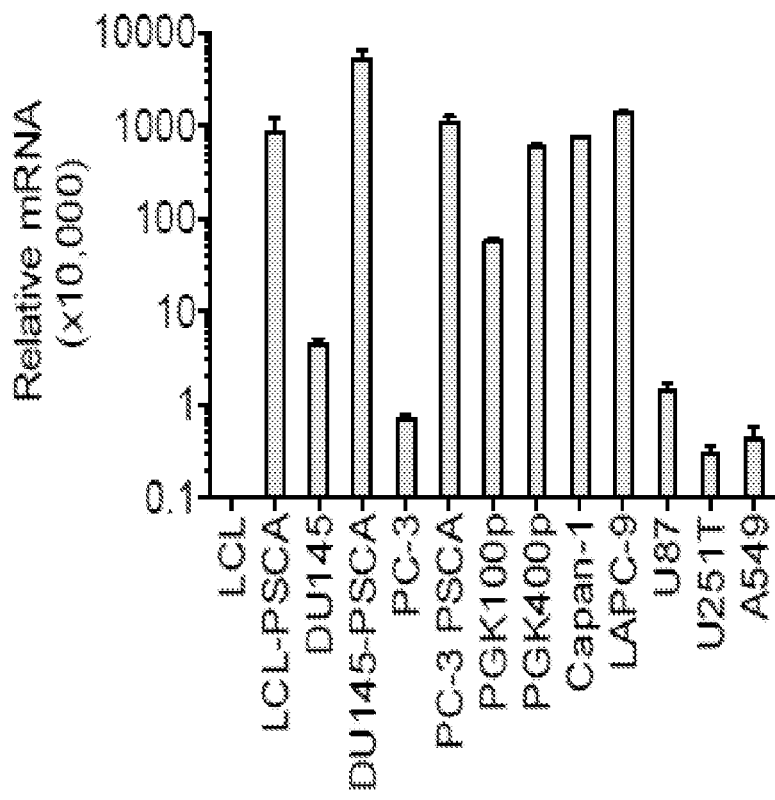
FIG. 13: mRNA expression analysis of PSCA in tumor cell lines. (a) qPCR performed on various prostate and non-prostate cancer cell lines to quantify PSCA expression. PSCA mRNA was normalized to GAPDH mRNA.

Next, several human prostate cancer cell lines that were stably engineered to express the human PSCA gene under the control of the EF1α promoter tumor killing abilities of PSCA(ΔCH2)28ζ and PSCA(ΔCH2)BBζ CAR T cells (FIG. 8A). PC-3 tumor cells were also engineered with PSCA driven by a mutant PGK promoter (Frigault et al. 2015 *Cancer Immunol Res* 3:356) to derive a low antigen-density cell line (denoted PGK100p). LAPC-9 is a primary tumor xenograft derived from a patient with bone metastatic prostate cancer (Craft et al. 1999 *Cancer Res* 59:503) that endogenously expresses PSCA. PSCA(ΔCH2)28ζ or PSCA (ΔCH2)BBζ CAR T cells were co-cultured with various tumor targets. Cell imaging demonstrated qualitatively that both CARs killed with similar kinetics (FIG. 8B). In a separate tumor killing assay, flow cytometry was used to quantify tumor killing by PSCA(ΔCH2)28ζ and PSCA(ΔCH2)BBζ CAR T cells. While both PSCA(ΔCH2)28ζ and PSCA(ΔCH2)BBζ CAR T cells killed PSCA-expressing tumor cells with similar efficacy, PSCA(ΔCH2)28ζ showed targeting of wild-type non-PSCA expressing DU145 and PC-3 tumor cells (FIG. 8C). Quantitative real-time PCR analysis of PSCA expression was performed on all tumor targets, and showed that while PSCA protein expression was undetectable by flow cytometry in wild-type DU145 and PC-3 cells, mRNA expression was detected in these lines (FIG. 13), which likely contributed to targeting by CD28-containing CARs.

Figure 14:
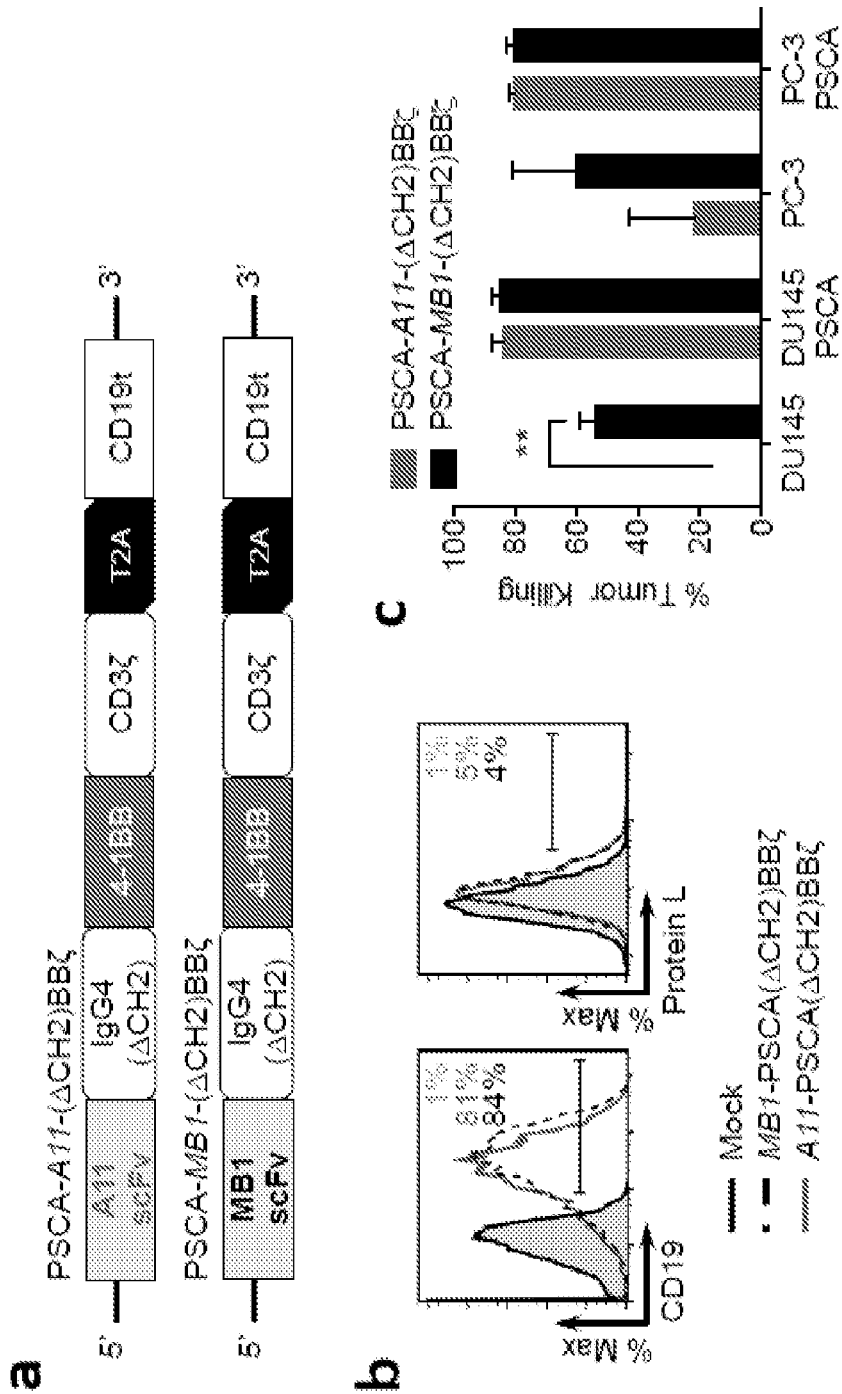
FIG. 14A-C: Comparison of MB1 scFv-containing and A11 scFv-containing PSCA-CARs. (A) Diagram of the lentiviral expression cassette with PSCA-CARs containing the humanized MB1 or A11 scFv targeting PSCA, with a 129 amino acid modified human IgG4 Fc linker (void of the CH2 domain, ΔCH2), a CD4 transmembrane domain, a cytoplasmic 4-1BB costimulatory domain, and a cytolytic CD3ζ domain. A truncated non-signaling CD19 (CD19t) is separated from the CAR with a T2A ribosomal skip sequence for tracking CAR-expressing cells. (B) Mock (untransduced), PSCA-MB1-(ΔCH2) BBζ, or PSCA-A11-(ΔCH2)BBζ CAR T cells expressing CD19 to detect lentiviral transduction of CARs (top) or Protein L to detect the scFv (bottom) as determined by flow cytometry. (C) Tumor killing assay assessed by flow cytometry following a 3-day co-culture with indicated tumor targets.

The impact of an alternative PSCA scFv, MB1 [33], was examined. (FIG. 14A). While both MB1 and A11-based 4-1BB-containing PSCA-CARs were expressed with similar stability (FIG. 14B), CARs containing the MB1 scFv showed significant targeting of wild-type tumor cells compared to CARs containing the A11 scFv (FIG. 14C). These data suggest that antigen-targeting and co-stimulatory domains work in concert to provide tumor selectivity of CARs, and that the non-selectivity of one domain may override the selectivity driven by another domain.

In addition to enhanced selectivity and a lack of killing of wild-type, non-PSCA expressing tumor cells, PSCA(ΔCH2)BBζ CAR T cells exhibited less evidence of exhaustion compared to PSCA(ΔCH2)28ζ CAR T cells, as indicated by reduced expression of programmed death-1 (PD-1) (FIG. 8D). The difference in PD-1 expression between PSCA(ΔCH2)BBζ and PSCA(ΔCH2)28ζ was primarily seen in the CD8+ subset of CAR T cells (FIG. 8E). Additionally, similar trends, albeit less robust, were observed with other exhaustion markers, including LAG3 and TIM3 (data not shown).

A time-course killing assay in which the killing ability of PSCA(ΔCH2)28ζ and PSCA(ΔCH2)BBζ at one, two and three days of co-culture with tumor cells was used to examine the kinetics of PD-1 expression (FIG. 8F). These data quantitatively confirmed that PSCA(ΔCH2)28ζ and PSCA(ΔCH2)BBζ killed DU145-PSCA equivalently over time, but that PSCA(ΔCH2)28ζ had higher PD-1 expression.

In another study, PSCA(ΔCH2)28ζ and PSCA(ΔCH2)BBζ were co-cultured against a low PSCA-expressing tumor line (PC-3-PGK100p) and a high PSCA-expressing tumor line (PC-3-PSCA) at varying effector:target (E:T) ratios. This studied showed that at lower E:T ratios, PSCA(ΔCH2)BBζ were more selective for high PSCA-expressing tumor cells compared to PSCA(ΔCH2)28ζ (FIG. 8G). Similar findings were observed using either PBMC- or $T_{CM}$-derived PSCA-CAR T cells (data not shown). Together, these data suggest that 4-1BB co-stimulation allows for potent and selective killing of high PSCA-expressing tumor cells while minimizing activity against lower PSCA-expressing cells, while CD28-containing CARs lack such targeting selectivity.

Figure 9:
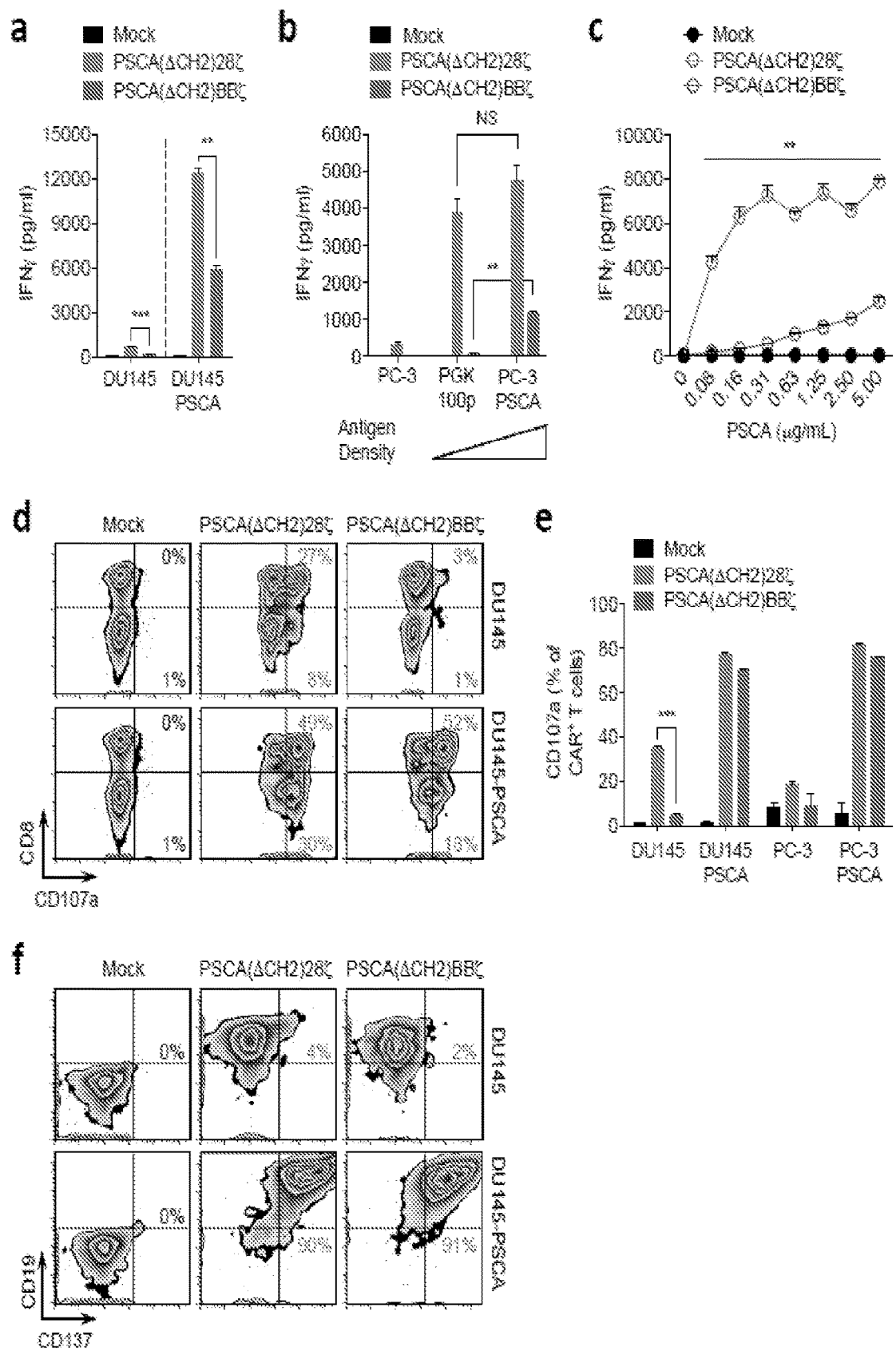
FIG. 9A-F: PSCA-BBζ CARS show antigen-dependent cytokine production in vitro. (A) IFNγ production quantified by ELISA in supernatants from PSCA-CAR T cells cultured overnight with DU145 or DU145-PSCA tumor cells. (B) Same as in (A) from PSCA-CAR T cells cultured overnight with PC-3, PC-3-PGK100p, or PC-3-PSCA tumor cells. (C) IFNγ production quantified by ELISA in supernatants from PSCA-CAR T cells cultured overnight on plate-bound recombinant human PSCA at varying protein concentrations. (D) Representative zebra plots showing CD107a degranulation by PSCA-CAR T cells following a 4-6 hr co-culture with indicated tumor targets. (E) Quantification of CD107a degranulation by PSCA-CAR T cells from (D). (F) Representative zebra plots of CD137 expression in Mock, PSCA(ΔCH2)28ζ, or PSCA(ΔCH2)BBζ CAR T cells following a 3-day co-culture with indicated tumor targets. Data are shown as n=2 per group±SD. All data are representative of at least two independent experiments.
Figure 15:
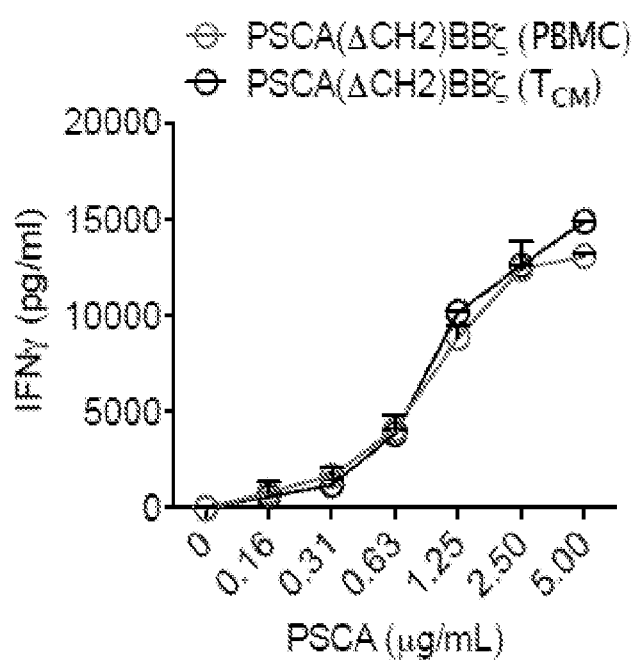
FIG. 15: Cytokine production by PSCA(ΔCH2)BBζ CAR T cells transduced in either PBMC or TCM. IFNγ production quantified by ELISA in supernatants from PSCA-CAR T cells cultured on plate-bound recombinant human PSCA at varying protein concentrations.

Example 8: 4-1BB-Containing PSCA-CARs Demonstrate Dampened Yet Selective Cytokine Production Compared with CD28-Containing PSCA-CARs To further investigate the differences between CD28- and 4-1BB-containing PSCA-CARs, studies were conducted to compare their respective T cell activation and cytokine production. These studies revealed significant dampening of IFNγ production by PSCA(ΔCH2)BBζ cells compared to PSCA(ΔCH2)28ζ CAR T cells following an overnight co-culture with DU145-PSCA tumor cells (FIG. 9A). Similar dampening of cytokine production was observed for 4-1BB-containing CARs against PC-3-PSCA. While CD28-containing PSCA-CAR T cells produced equivalent IFNγ levels against low- and high-PSCA-expressing tumor cells, 4-1BB-containing CAR T cells produced lower IFNγ against low PSCA-expressing tumor cells (FIG. 9B). To rule out potential non-CAR-mediated effects on cytokine production by tumor cells, similar IFNγ measurements by PSCA(ΔCH2)BBζ CAR T cells against plate-bound recombinant human PSCA protein were performed. While CD28-containing CAR T cells showed a saturated response against low or high levels of PSCA, IFNγ production by 4-1BB-containing PSCA-CAR T cells was contingent upon antigen density (FIG. 9C). Similar cytokine responses were observed independent of the T cell subset used to generate PSCA-CAR T cells (FIG. 15).

Figure 16:
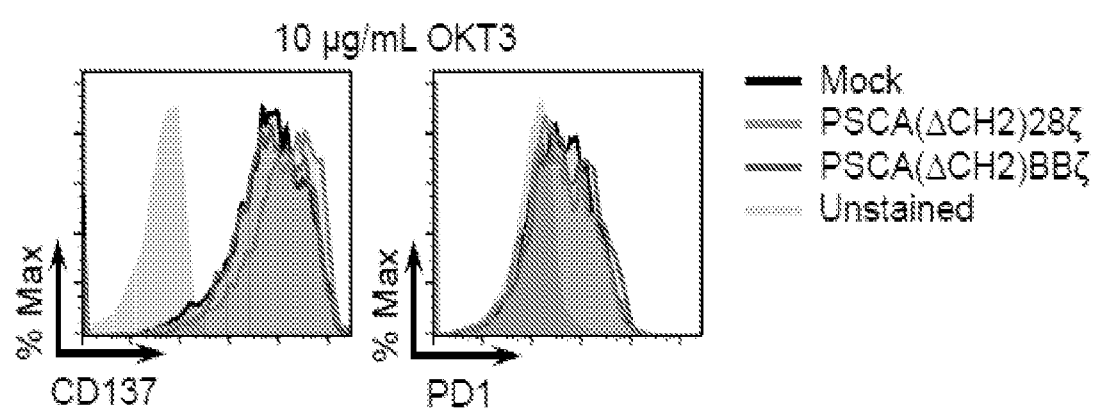
FIG. 16: Activation and exhaustive phenotype of Mock, PSCA(ΔCH2)28ζ, and PSCA(ΔCH2)BBζ CAR T cells against plate-bound OKT3. CD137 and PD1 expression by flow cytometry in T cells following 2-day incubation with plate-bound OKT3 (10 µg/mL).

4-1BB-containing PSCA-CARs showed a slight reduction compared to CD28-containing CARs in CD107a degranulation against PSCA-expressing tumor cells (FIG. 9D and FIG. 9E). Significant targeting of non-PSCA-expressing tumor cells by PSCA(ΔCH2)28ζ, as measured by CD107a expression was observed. The activation status of PSCA(ΔCH2)28ζ and PSCA(ΔCH2)BBζ cells were comparable, as measured by 4-1BB (CD137) expression in a 3-day tumor killing assay (FIG. 9F). To ensure that differences in PSCA-CAR T cells were due to antigen targeting rather than an intrinsic defect in T cell activity, we confirmed similar activation (CD137) and exhaustion (PD-1) in T cells stimulated with plate-bound anti-human CD3 antibody, OKT3 (FIG. 16).

Figure 10:
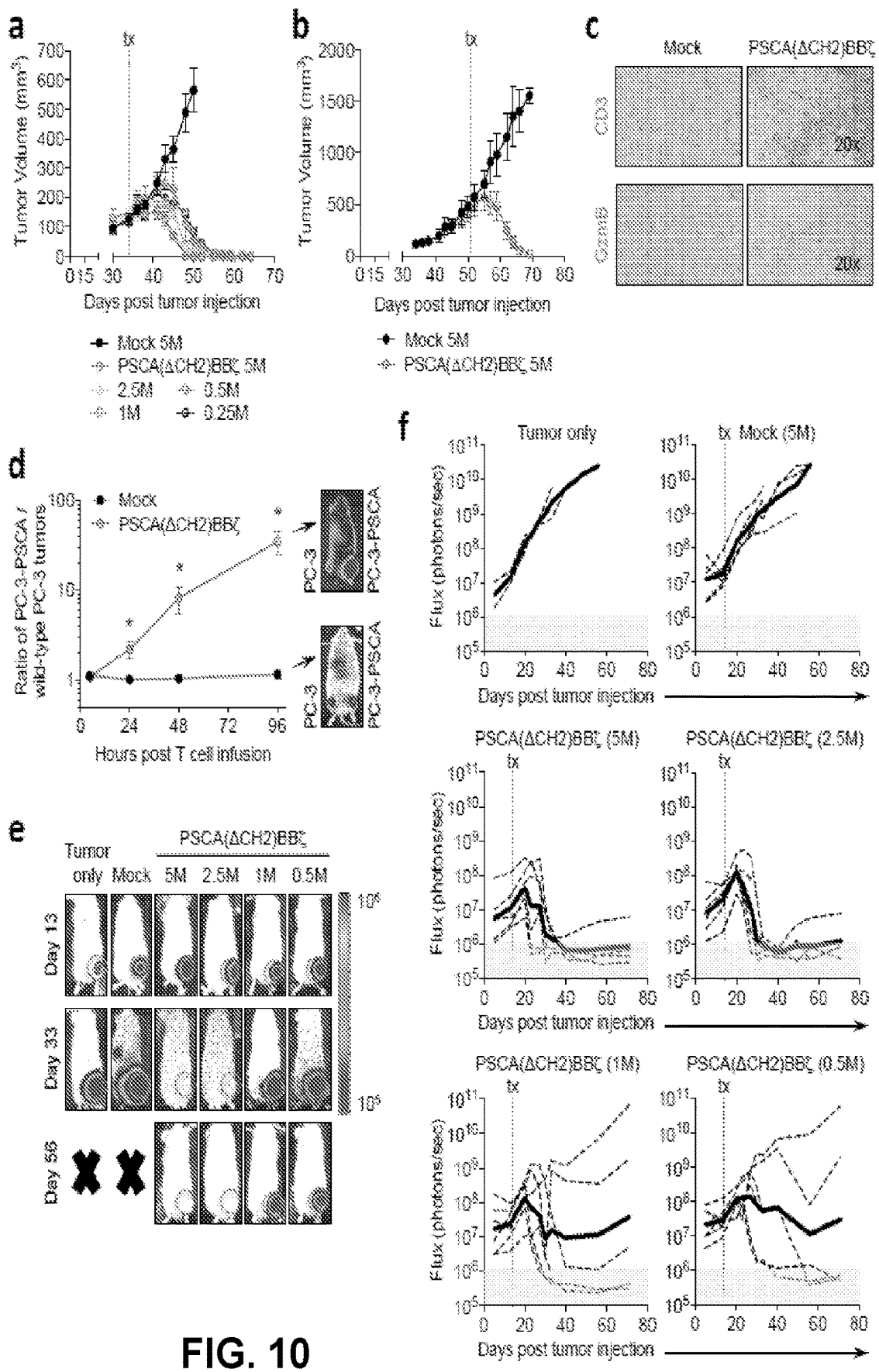
FIG. 10A-F: Robust therapeutic efficacy of PSCA(ΔCH2) BBδ CAR T cells in subcutaneous and orthotopic bone metastatic human xenograft models of prostate cancer. (A) Tumor volume (mm³) in NSG mice bearing subcutaneous PC-3-PSCA (2.5×10⁶) tumors on day 0, treated with Mock or PSCA(ΔCH2)BBζ CAR T cells at the indicated doses by intratumoral (i.t.) injection on day 34. N=4 mice per group. Data are representative of at least two independent experiments. (B) Mice with large tumors (approx. 500 mm3) treated with 5×10⁶ Mock or CAR T cells by i.v. injection on day 51. N=3 mice per group. Data are representative of at least two independent experiments. (C) Immunohistochemistry of PC-3-PSCA tumors harvested 11 days post i.v. T cell treatment stained with human CD3 (upper panels) and Granzyme B (lower panels). (D) Mice bearing intratibial tumors, with PC-3 (wild-type) cells (0.2×106) in the right hind leg, and PC-3-PSCA cells (0.2×10⁶) in the left hind leg. On day 14, mice were treated with 5×10⁶ firefly luciferase-positive (~30%) Mock or PSCA(ΔCH2)BBζ CAR T cells by i.v. injection. T cell trafficking was monitored at 4 hours, 1 day, 2 days, and 4 days by non-invasive optical imaging (Xenogen). Quantification of flux images, showing the ratio of PC-3-PSCA/PC-3 (wild-type). N=4-6 mice per group. (e) NSG mice bearing intratibial (left hind leg) PC-3-PSCA-eGFP-ffluc (0.2×10⁶). Tumor growth kinetics were monitored by non-invasive optical imaging (Xenogen). On day 14, mice were i.v. injected with 5×10⁶ Mock or varying doses of PSCA(ΔCH2)BBζ CAR T cells. Representative flux images of mice on day 13 (pre-treatment) and day 33 are shown. (F) Quantification of flux images (with region of interest (ROI) at site of tumor injection) from tumor only, Mock T cells (5×10⁶), and PSCA(ΔCH2)BBζ CAR T cells (5×10⁶, 2.5×10⁶, 1×10⁶, 0.5×10⁶) groups. N□4 mice per group for CAR groups. Data are representative of at least two independent experiments.

Example 9: PSCA(ΔCH2)BBζ CAR T Cells Demonstrate Robust Therapeutic Efficacy in Subcutaneous Prostate Cancer Models In this study, mice bearing subcutaneous PC-3-PSCA tumors were treated with a single intratumoral injection of $5\times10^6$ PSCA(ΔCH2)BBζ CAR T cells. Complete tumor regression was observed within two weeks following intratumoral T cell injection. Although tumor regression was evident for over 30 days, tumors eventually recurred in the majority of animals with similar kinetics as the primary tumor (FIG. 17A), which we will address below. To establish whether systemic therapy of CAR T cells was achievable in this solid tumor model, varying doses of PSCA(ΔCH2)BBζ CAR T cells were delivered intravenously. While $5\times10^6$ PSCA-CAR T cells showed complete regression of tumors, a similar yet delayed therapeutic efficacy was observed with a CAR dose as little as $0.25\times10^6$ (FIG. 10A). To extend the findings to a large tumor burden, large PC-3-PSCA tumors (~500 mm³) were treated with a single intravenous injection of $5\times10^6$ PSCA(ΔCH2)BBζ CAR T cells. Here rapid tumor regression was observed (FIG. 10B). Significant tumor infiltration of human T cells was observed 11 days following CAR T cell infusion (FIG. 10C, upper panel), which also expressed Granzyme B (FIG. 10D, lower panel), a marker of T cell activity. Tumors from Mock-treated mice showed very few human T cells or Granzyme B expression at the same time point.

Figure 17:
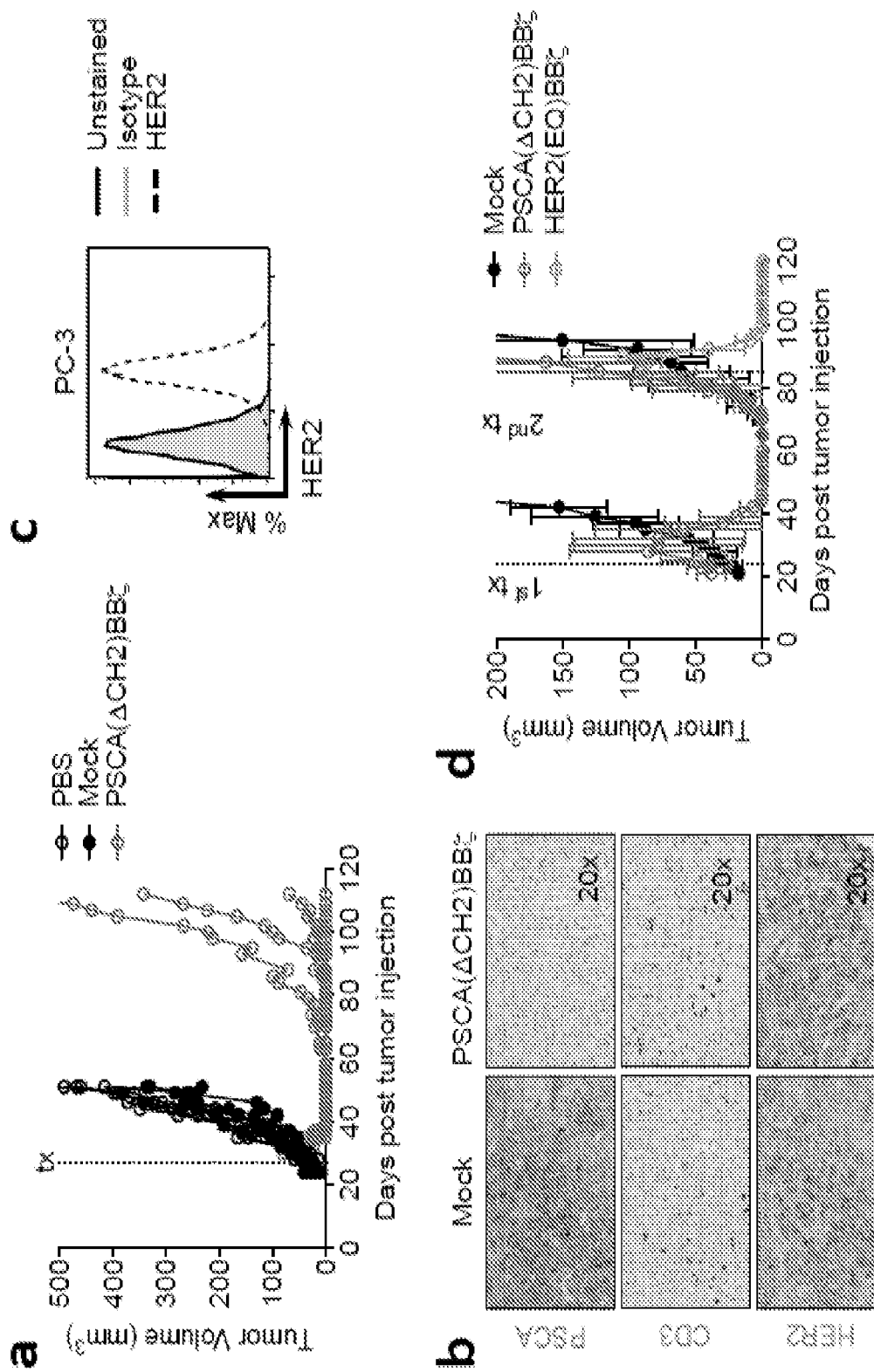
FIG. 17A-D: Treatment of PSCA-negative tumor recurrences with HER2-specific CAR T cells. (A) Kinetics of tumor recurrences in PSCA(ΔCH2)BBζ treated PC-3-PSCA tumor bearing mice. Each line represents an individual mouse per group. N=4 per group. Data are representative of at least two independent studies. (B) Immunohistochemistry of PC-3-PSCA tumors harvested from Mock-treated (at primary endpoint) or recurrent PSCA(ΔCH2)BBζ-treated tumors stained with human PSCA, CD3 and HER2. (C) HER2 expression in PC-3-PSCA tumor cells, assessed by flow cytometry. (D) Tumor volume (mm$^3$) in mice bearing PC-3-PSCA tumors treated i.v. with 5×10$^6$ Mock or PSCA (ΔCH2)BBζ CAR T cells (N=6 per group) on day 24 ("1st tx"). On day 81, when CAR T cell-treated mice showed tumor recurrence (50-100 mm$^3$), mice were assigned to a second treatment ("2nd tx") receiving i.t. injections of either 5×10$^6$ Mock, PSCA(ΔCH2)BBζ, or HER2 CAR T cells (N=2 per group).

Recurrence following single antigen-specific CAR T cell therapy might be an expected phenomenon given the heterogenic antigen profile of solid tumors, but the mechanisms underlying resistance/recurrence are still being explored. To better understand the delayed tumor recurrences that were observed in FIG. 10A, immunohistochemistry was used to assess the continued presence of antigen on tumor cells, and the PSCA-CAR T cell persistence. Interestingly, while Mock-treated tumors were highly positive for PSCA, tumors that recurred following PSCA(ΔCH2)BBζ CAR T cell treatment were PSCA negative (FIG. 17B, upper panel). In the same recurring tumors, however, human T cells were abundant (FIG. 17B, middle panel), even though these tumors were harvested at least 2-months post-CAR T cell infusion. PC-3 cells also express HER2 in vitro (FIG. 17C) and it was confirmed that both Mock- and PSCA(ΔCH2)BBζ-treated recurrent tumors expressed HER2 at equivalent levels in vivo (FIG. 17B, lower panel). To determine whether tumors were PSCA-negative and still susceptible to CAR T cell therapy, recurrent tumors were treated by intratumoral injection with either Mock, PSCA-directed- or HER2-directed- CAR T cells. Although recurrent PSCA-negative tumors were non-responsive to PSCA-CARs, they were susceptible to HER2-CAR T cell treatment (FIG. 17D).

Example 10: PSCA(ΔCH2)BBζ CAR T Cells Traffic to Bone and Exhibit Anti-Tumor Efficacy in Bone Metastatic Prostate Cancer One of the major obstacles for cellular immunotherapy is the immunosuppressive microenvironment that can hamper effective trafficking and survival of T cells in solid tumors. To directly evaluate trafficking and antigen-dependent CAR T cell expansion in bone metastatic prostate tumors, firefly luciferase-labeled PSCA(ΔCH2)BBζ CAR T cells were i.v. injected into mice bearing intratibial wild-type PC-3 (anatomical right tibia) and PC-3-PSCA (anatomical left tibia) tumors. Interestingly, while Mock and PSCA-CAR T cells showed equal early trafficking to both tumors (at 4 hours post T cell infusion), PSCA-CAR T cells were predominantly found in PSCA-expressing tumors at 1 day following T cell injection, which increased over the 4 days of kinetic imaging (FIG. 10D), indicating antigen-dependent trafficking and/or CAR T cell proliferation in PSCA-positive tumors. Next, a study was conducted in which PC-3-PSCA tumor cells were injected into the intratibial space. On day 14 post tumor engraftment, these tumor-bearing mice were intravenously treated with a dose de-escalation of PSCA (ΔCH2)BBζ CAR T cells ($0.5\times10^6$ to $5\times10^6$) (FIG. 10E). The large majority of mice treated with either $5\times10^6$ or $2.5\times10^6$ CAR T cells showed complete tumor regression whereas mice treated with either $1\times10^6$ or $0.5\times10^6$ CAR T cells had a more heterogeneous therapeutic response (FIG. 10F The clinical relevance of this model is evident when effective doses from the orthotopic studies were compared with doses used in the subcutaneous model where complete regression was observed with CAR T cell doses as little as $0.25\times10^6$. It is likely that the discrepancy in overall therapy observed in these models is due to differences in the infiltration and survival of CAR T cells in these tumor micro environments.

Figure 11:
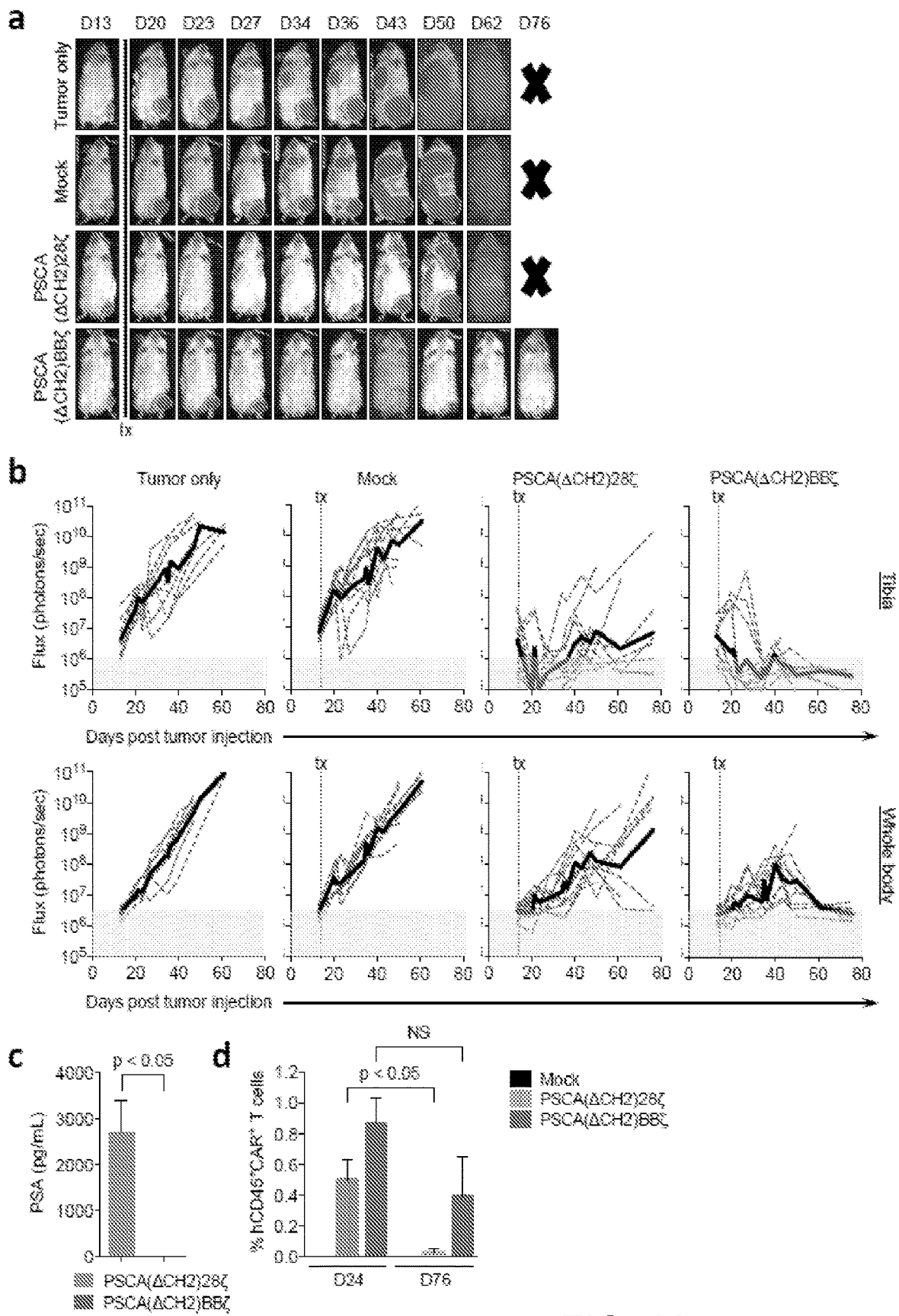
FIG. 11A-D: Durable anti-tumor efficacy of PSCA (ΔCH2)BBζ CAR T cells compared with PSCA(ΔCH2)28ζ CAR T cells in a prostate cancer patient-derived bone metastatic xenograft model. (A) NSG mice bearing intratibial (left hind leg) LAPC-9-eGFP-ffluc (0.15×10⁶). Tumor growth kinetics were monitored by non-invasive optical imaging (Xenogen). On day 14, mice were i.v. injected with 5×106 Mock, PSCA(ΔCH2)28ζ or PSCA(ΔCH2)BBζ CAR T cells. Representative flux images of mice on indicated days are shown. (B) Quantification of flux images, with ROI at the tibia (upper panels) or from whole body (lower panels) from each treatment group. (C) PSA levels determined by ELISA from serum harvested from treated mice (n=2-3 per group) at day 76 post tumor injection. (D) Flow cytometric analysis of peripheral blood of mice 24 and 76 days post tumor injection (n=2-3 per group). Data are compiled from two independent in vivo experiments.

Example 11: 4-1BB Co-Stimulation Provides Superior Persistence and Durable Anti-Tumor Responses of PSCA-CARs in a Clinically Relevant Bone Metastatic Prostate Cancer Model The studies described above were extended using the endogenous PSCA-expressing bone metastatic prostate cancer patient-derived tumor xenograft, LAPC-9. On day 14 post tumor engraftment, mice treated with a single i.v. injection of $5\times10^6$ PSCA(ΔCH2)BBζ CAR T cells showed near complete regression of tumors at the intratibial tumor site (FIG. 11A). Although intratibial tumors were effectively targeted, LAPC-9 tumors disseminated to other sites in the body, which were found to be particularly evident in various lymph nodes (axillary and inguinal) and the thymus as confirmed by immunohistochemistry (data not shown). Although these seemingly grew for several weeks after initial tumor regression in the bone, they were ultimately eradicated by PSCA(ΔCH2)BBζ CAR T cells.

Based on the requirement of persistent T cells for complete anti-tumor activity of PSCA-CARs, a study was conducted to compare PSCA-CARs containing either CD28 or 4-1BB co-stimulatory domains. While both PSCA(ΔCH2) 28ζ and PSCA(ΔCH2)BBζ CAR T cells showed dramatic regression of bone metastases, mice receiving CD28-containing PSCA-CARs showed recurrence at the primary tumor site as well as metastatic disease, while 4-1BB-containing PSCA-CAR-treated mice showed complete anti-tumor responses (FIG. 11A and FIG. 11B). Tumor recurrence in PSCA(ΔCH2)28ζ CAR T cell-treated mice was confirmed by quantifying PSA levels in the blood at Day 76 post CAR T cell treatment (FIG. 10C). CAR T cells were quantified in the blood of treated animals, and while CAR T cells were observed in both groups at Day 24 post tumor injection, PSCA(ΔCH2)BBζ CAR T cells were significantly more abundant at Day 76, indicating greater persistence (FIG. 10D). Overall, these studies demonstrate potent and durable anti-tumor efficacy with PSCA(ΔCH2)BBζ CAR T cells in multiple tumor systems, including orthotopic bone metastatic models of prostate cancer.

Example 12: Construction and Structure of epHIV7 Used for Expression of CAR

The pHIV7 plasmid is the parent plasmid from which the various CAR expression vectors were derived in the T cell Therapeutics Research Laboratory (TCTRL) at City of Hope (COH). The epHIV7 vector used for expression of the CAR was produced from pHIV7 vector. Importantly, this vector uses the human EF1 promoter to drive expression of the CAR. Both the 5' and 3' sequences of the vector were derived from pv653RSN as previously derived from the HXBc2 provirus. The polypurine tract DNA flap sequences (cPPT) were derived from HIV-1 strain pNL4-3 from the NIH AIDS Reagent Repository. The woodchuck post-transcriptional regulatory element (WPRE) sequence was previously described.

Construction of pHIV7 was carried out as follows. Briefly, pv653RSN, containing 653 bp from gag-pol plus 5' and 3' long-terminal repeats (LTRs) with an intervening SL3-neomycin phosphotransferase gene (Neo), was subcloned into pBluescript, as follows: In Step 1, the sequences from 5' LTR to rev-responsive element (RRE) made p5'HIV-1 51, and then the 5' LTR was modified by removing sequences upstream of the TATA box, and ligated first to a CMV enhancer and then to the SV40 origin of replication (p5'HIV-2). In Step 2, after cloning the 3' LTR into pBluescript to make p3'HIV-1, a 400-bp deletion in the 3' LTR enhancer/promoter was made to remove cis-regulatory elements in HIV U3 and form p3'HIV-2. In Step 3, fragments isolated from the p5'HIV-3 and p3'HIV-2 were ligated to make pHIV-3. In Step 4, the p3'HIV-2 was further modified by removing extra upstream HIV sequences to generate p3'HIV-3 and a 600-bp BamHI-SalI fragment containing WPRE was added to p3'HIV-3 to make the p3'HIV-4. In Step 5, the pHIV-3 RRE was reduced in size by PCR and ligated to a 5' fragment from pHIV-3 (not shown) and to the p3'HIV-4, to make pHIV-6. In Step 6, a 190-bp BglII-BamHI fragment containing the cPPT DNA flap sequence from HIV-1 pNL4-3 (55) was amplified from pNL4-3 and placed between the RRE and the WPRE sequences in pHIV6 to make pHIV-7. This parent plasmid pHIV7-GFP (GFP, green fluorescent protein) was used to package the parent vector using a four-plasmid system.

A packaging signal, psi ψ, is required for efficient packaging of viral genome into the vector. The RRE and WPRE enhance the RNA transcript transport and expression of the transgene. The flap sequence, in combination with WPRE, has been demonstrated to enhance the transduction efficiency of lentiviral vector in mammalian cells.

The helper functions, required for production of the viral vector), are divided into three separate plasmids to reduce the probability of generation of replication competent lentivirus via recombination: 1) pCgp encodes the gag/pol protein required for viral vector assembly; 2) pCMV-Rev2 encodes the Rev protein, which acts on the RRE sequence to assist in the transportation of the viral genome for efficient packaging; and 3) pCMV-G encodes the glycoprotein of the vesiculo-stomatitis virus (VSV), which is required for infectivity of the viral vector.

There is minimal DNA sequence homology between the pHIV7 encoded vector genome and the helper plasmids. The regions of homology include a packaging signal region of approximately 600 nucleotides, located in the gag/pol sequence of the pCgp helper plasmid; a CMV promoter sequence in all three helper plasmids; and a RRE sequence in the helper plasmid pCgp. It is highly improbable that replication competent recombinant virus could be generated due to the homology in these regions, as it would require multiple recombination events. Additionally, any resulting recombinants would be missing the functional LTR and tat sequences required for lentiviral replication.

The CMV promoter was replaced by the EF1α-HTLV promoter (EF1p), and the new plasmid was named epHIV7. The EF1p has 563 bp and was introduced into epHIV7 using NruI and NheI, after the CMV promoter was excised.

The lentiviral genome, excluding gag/pol and rev that are necessary for the pathogenicity of the wild-type virus and are required for productive infection of target cells, has been removed from this system. In addition, the CLRX-IgG4Fc (EQ)-CD28-zeta-T2ACD19t_epHIV7 vector construct does not contain an intact 3'LTR promoter, so the resulting expressed and reverse transcribed DNA proviral genome in targeted cells will have inactive LTRs. As a result of this design, no HIV-I derived sequences will be transcribed from the provirus and only the therapeutic sequences will be expressed from their respective promoters. The removal of the LTR promoter activity in the SIN vector is expected to significantly reduce the possibility of unintentional activation of host genes.

Example 13: Production of Vectors for Transduction of T Cells

For each plasmid expressing a CAR, a seed bank was generated, which is used to inoculate the fermenter to produce sufficient quantities of plasmid DNA. The plasmid DNA was tested for identity, sterility and endotoxin prior to its use in producing lentiviral vector.

Briefly, cells were expanded from the 293T working cell (WCB), which has been tested to confirm sterility and the absence of viral contamination. A vial of 293T cells from the 293T WCB was thawed. Cells were grown and expanded until sufficient numbers of cells existed to plate an appropriate number of 10 layer cell factories (CFs) for vector production and cell train maintenance. A single train of cells can be used for production.

The lentiviral vector was produced in sub-batches of up to 10 CFs. Two sub-batches can be produced in the same week leading to the production of approximately 20 L of lentiviral supernatant/week. The material produced from all sub-batches was pooled during the downstream processing phase, in order to produce one lot of product. 293T cells were plated in CFs in 293T medium (DMEM with 10% FBS). Factories were placed in a 37° C. incubator and horizontally leveled in order to get an even distribution of the cells on all the layers of the CF. Two days later, cells were transfected with the four lentiviral plasmids described above using the $CaPO_4$ method, which involves a mixture of Tris:EDTA, 2M $CaCl_2$, 2×HBS, and the four DNA plasmids. Day 3 after transfection, the supernatant containing secreted lentiviral vectors was collected, purified and concentrated. After the supernatant was removed from the CFs, End-of-Production Cells were collected from each CF. Cells were trypsinized from each factory and collected by centrifugation. Cells were resuspended in freezing medium and cryopreserved. These cells were later used for replication-competent lentivirus (RCL) testing.

To purify and formulate vectors crude supernatant was clarified by membrane filtration to remove the cell debris. The host cell DNA and residual plasmid DNA were degraded by endonuclease digestion (Benzonase®). The viral supernatant was clarified of cellular debris using a 0.45 µm filter. The clarified supernatant was collected into a pre-weighed container into which the Benzonase® is added (final concentration 50 U/mL). The endonuclease digestion for residual plasmid DNA and host genomic DNA as performed at 37° C. for 6 h. The initial tangential flow ultrafiltration (TFF) concentration of the endonuclease-treated supernatant was used to remove residual low molecular weight components from the crude supernatant, while concentrating the virus ~20 fold. The clarified endonuclease-treated viral supernatant was circulated through a hollow fiber cartridge with a NMWCO of 500 kD at a flow rate designed to maintain the shear rate at ~4,000 sec-1 or less, while maximizing the flux rate. Diafiltration of the nuclease-treated supernatant was initiated during the concentration process to sustain the cartridge performance. An 80% permeate replacement rate was established, using 4% lactose in PBS as the diafiltration buffer. The viral supernatant was brought to the target volume, representing a 20-fold concentration of the crude supernatant, and the diafiltration was continued for 4 additional exchange volumes, with the permeate replacement rate at 100%.

Further concentration of the viral product was accomplished by using a high speed centrifugation technique. Each sub-batch of the lentivirus was pelleted using a Sorvall RC-26 plus centrifuge at 6000 RPM (6,088 RCF) at 6° C. for 16-20 h. The viral pellet from each sub-batch was then reconstituted in a 50 mL volume with 4% lactose in PBS. The reconstituted pellet in this buffer represents the final formulation for the virus preparation. The entire vector concentration process resulted in a 200-fold volume reduction, approximately. Following the completion of all of the sub-batches, the material was then placed at −80° C., while samples from each sub-batch were tested for sterility. Following confirmation of sample sterility, the sub-batches were rapidly thawed at 37° C. with frequent agitation. The material was then pooled and manually aliquoted in the Class II Type A/B3 biosafety cabinet in the viral vector suite. A fill configuration of 1 mL of the concentrated lentivirus in sterile USP class 6, externally threaded O-ring cryovials was used. Center for Applied Technology Development (CATD)'s Quality Systems (QS) at COH released all materials according to the Policies and Standard Operating Procedures for the CBG and in compliance with current Good Manufacturing Practices (cGMPs).

To ensure the purity of the lentiviral vector preparation, it was tested for residual host DNA contaminants, and the transfer of residual host and plasmid DNA. Among other tests, vector identity was evaluated by RT-PCR to ensure that the correct vector is present. All release criteria were met for the vector intended for use in this study.

Example 14: Preparation of T Cells Suitable for Expression of PSCA Targeted CAR

T lymphocytes are obtained from a patient by leukopheresis, and the appropriate allogenic or autologous T cell subset, for example, Central Memory T cells ($T_{CM}$), are genetically altered to express the CAR, then administered back to the patient by any clinically acceptable means, to achieve anticancer therapy.

Suitable $T_{CM}$ can be generated as follow. Apheresis products obtained from consented research participants are ficolled, washed and incubated overnight. Cells are then depleted of monocyte, regulatory T cell and naïve T cell populations using GMP grade anti-CD14, anti-CD25 and anti-CD45RA reagents (Miltenyi Biotec) and the CliniMACS™ separation device. Following depletion, negative fraction cells are enriched for CD62L+ $T_{CM}$ cells using DREG56-biotin (COH clinical grade) and anti-biotin microbeads (Miltenyi Biotec) on the CliniMACS™ separation device.

Following enrichment, $T_{CM}$ cells are formulated in complete X-Vivo15 plus 50 IU/mL IL-2 and 0.5 ng/mL IL-15 and transferred to a Teflon cell culture bag, where they are stimulated with Dynal ClinEx™ Vivo CD3/CD28 beads. Up to five days after stimulation, cells are transduced with lentiviral vector expressing the desired CAR at a multiplicity of infection (MOI) of 1.0 to 0.3. Cultures are maintained for up to 42 days with addition of complete X-Vivo15 and IL-2 and IL-15 cytokine as required for cell expansion (keeping cell density between $3 \times 10^5$ and $2 \times 10^6$ viable cells/mL, and cytokine supplementation every Monday, Wednesday and Friday of culture). Cells typically expand to approximately $10^9$ cells under these conditions within 21 days. At the end of the culture period cells are harvested, washed twice and formulated in clinical grade cryopreservation medium (Cryostore CS5, BioLife Solutions).

On the day(s) of T cell infusion, the cryopreserved and released product is thawed, washed and formulated for re-infusion. The cryopreserved vials containing the released cell product are removed from liquid nitrogen storage, thawed, cooled and washed with a PBS/2% human serum albumin (HSA) Wash Buffer. After centrifugation, the supernatant is removed and the cells resuspended in a Preservative-Free Normal Saline (PFNS)/2% HSA infusion diluent. Samples are removed for quality control testing.

Techniques Used in Examples 7-11

Cell Lines: (Human metastatic prostate cancer cell lines DU145 (ATCC HTB-81) and PC-3 (ATCC CRL-1435) were cultured in RPMI-1640 (Lonza) containing 10% fetal bovine serum (FBS, Hyclone), and 1× antibiotic-antimycotic (Gibco) containing 100 U/mL penicillin, 100 ug/mL streptomycin, and 0.25 ug/mL fungizone (complete RPMI). The human fibrosarcoma cell line, HT1080 (ATCC CCL-121), and the human embryonic kidney cell line, 293T (ATCC CRL-3216), were cultured in Dulbecco's Modified Eagles Medium (DMEM, Life Technologies) containing 10% FBS, 1× antibiotic-antimycotic, 25 mM HEPES (Irvine Scientific), and 2 mM L-Glutamine (Fisher Scientific) (complete DMEM). The human prostate cancer xenograft LAPC-9 (a kind gift from Dr. Robert Reiter, UCLA) was cultured in Iscove's Modified Dulbecco's Medium (IMDM, Irvine Scientific) containing 20% FBS and 1× antibiotic-antimycotic (complete IMDM). LAPC-9 cells were serially passaged in male NOD.Cg-Prkdc$^{scid}$ IL2rg$^{tm1Wjl}$/(NSG) mice, and single-cell suspensions were prepared as previously described (Craft et al. 1999 *Cancer Res* 59:5030). Briefly, tumor tissue was harvested, minced in a petri dish, and digested with 1% Pronase E (Roche). Following a wash with complete IMDM, single-cell suspensions were filtered through a 40 µm cell strainer (Falcon), washed again, and frozen immediately. An EBV-transformed lymphoblastoid cell line (LCL) and LCL cells containing a membrane-tethered CD3 epsilon specific scFv agonist OKT3 (LCL-OKT3(Wang et al. 2011 *Blood* 117:1888) were cultured in complete RPMI. All cells were cultured at 37° C. with 5% $CO_2$. DU145 and PC-3 cells were authenticated by STR Profiling and verified mycoplasma negative (DDC Medical, OH).

DNA Constructs and Lentivirus Production: DU145 and PC-3 tumor cells were engineered to express PSCA by transduction with epHIV7 lentivirus carrying the human PSCA gene (Accession #: NM_005672.4) under the control of the EF1α promoter. PSCA$^+$ cells were stained with the mouse anti-human PSCA antibody (1G8) as described below (see 'Intracellular/Extracellular Staining and Flow Cytometry' section), and then FACS sorted using the BD FACSAria™ Special Order Research Product (SORP) cell sorter. For generation of tumor cells with low PSCA expression, the PSCA gene was placed under the control of mutated versions of the PGK promoter as previously described (Frigault et al. 2015 *Cancer Immunol Res* 3:356). The A11 scFv (Lepin et al. 2010 *Eur J Nucl Med Mol Imaging* 37:529) sequence was kindly provided by Drs. Anna Wu and Robert Reiter (UCLA). The MB1 scFv sequence was previously published (Feldmann et al. 2012 *J Immunol* 189:3249). CAR constructs with a truncated CD19 gene (CD19t) separated by a T2A ribosomal skip sequence were cloned in an epHIV7 lentiviral backbone. The antigen-targeting domain included either the A11 or the MB1 scFv. The extracellular spacer domain included the 129-amino acid middle-length CH2-deleted version (ΔCH2) of the IgG4 Fc spacer (Jonnalagadda et al. 2015 *Mol Ther* 23:757) intracellular co-stimulatory signaling domain contained that of either CD28 with a CD28 transmembrane domain, or 4-1BB with a CD4 transmembrane domain. The CD3ζ cytolytic domain was previously described (Cooper et al. 2003 *Blood* 101:1637).

Lentivirus was generated by plating 293T cells in T-225 tissue culture flasks 1-day prior to transfection with packaging plasmids and desired CAR lentiviral backbone plasmid. Supernatants were collected after 3 to 4 days, filtered and centrifuged to remove cell debris, and incubated with 2 mM magnesium and 25 U/mL Benzonase® endonuclease (EMD Millipore) to remove contaminating nucleic acids. Supernatants were combined and concentrated via high-speed centrifugation (6080 g) overnight at 4° C. Lentiviral pellets were then resuspended in phosphate-buffered saline (PBS)-lactose solution (4 g lactose per 100 mL PBS), aliquoted and stored at −80° C. for later use. Lentiviral titers, as determined by CD19t expression, were quantified using HT1080 cells.

T Cell Isolation, Lentiviral Transduction, and Ex Vivo Expansion: Leukapheresis products were obtained from consented research participants (healthy donors) under protocols approved by the City of Hope (COH) Internal Review Board (IRB). On the day of leukapheresis, peripheral blood mononuclear cells (PBMC) were isolated by density gradient centrifugation over Ficoll-Paque (GE Healthcare) followed by multiple washes in PBS/EDTA (Miltenyi Biotec). Cells were rested overnight at room temperature (RT) on a rotator, and subsequently washed and resuspended in complete X-VIVO. For studies utilizing total PBMC, cells were immediately frozen in CryoStor® CS5 cryopreservation media (BioLife Solutions). Up to $5\times10^9$ PBMC were incubated with anti-CD14, anti-CD25, and anti-CD45RA microbeads (Miltenyi Biotec) for 30 min at RT and magnetically depleted using the CliniMACS® system (Miltenyi Biotec) according to the manufacturer's protocol. Depleted PBMCs were then enriched for central memory T cells ($T_{CM}$) by incubating with biotinylated anti-CD62L antibody (produced by the Center for Biomedicine and Genetics at City of Hope) for 30 min at RT, and then with anti-Biotin microbeads (Miltenyi Biotec) for an additional 30 min at RT. $T_{CM}$ were then magnetically enriched using the autoMACS® system (Miltenyi Biotec) according to the manufacturer's protocol. For studies utilizing $T_{CM}$, cells were immediately frozen as described above. Purity and phenotype of PBMC and $T_{CM}$ were verified by flow cytometry.

Freshly thawed PBMC or $T_{CM}$ were washed once and cultured in X-VIVO-15 (Lonza) with 10% FBS (complete X-VIVO) containing 100 U/mL recombinant human IL-2 (rhIL-2, Novartis Oncology) and 0.5 ng/mL recombinant human IL-15 (rhIL-15, CellGenix). For CAR lentiviral transduction, T cells were cultured with CD3/CD28 Dynabeads® (Life Technologies), protamine sulfate (APP Pharmaceuticals), cytokine mixture (as stated above) and desired lentivirus at varying MOI either the day of, or the day following, bead stimulation. Spinoculation was performed by centrifugation at 2000 rpm for 30 min at 32° C. with no brake. Cells were then cultured in and replenished with fresh complete X-VIVO containing cytokines every 2-3 days. After 7-9 days, beads were magnetically removed, and cells were further expanded in complete X-VIVO containing cytokines to achieve desired cell yield. CAR T cells were positively selected for CD19t using the EasySep™ CD19 Positive Enrichment Kit I or II (StemCell Technologies) according to the manufacturer's protocol. Following further expansion, cells were frozen prior to in vitro functional assays and in vivo tumor models. Purity and phenotype of CAR T cells were verified by flow cytometry.

Intracellular/Extracellular Staining and Flow Cytometry: For flow cytometric analysis, cells were resuspended in FACS buffer (Hank's balanced salt solution without $Ca^{2+}$, $Mg^{2+}$, or phenol red (HBSS$^{-/-}$, Life Technologies) containing 2% FBS and 1× Antibiotic-Antimycotic). For PSCA staining, the mouse anti-human PSCA antibody (1G8) was kindly provided by Dr. Robert Reiter, UCLA. For detecting CAR scFv, biotinylated Protein-L (GenScript USA) was used as previously described[35]. Cells were incubated with primary antibodies for 30 minutes at 4° C. in the dark before proceeding to secondary staining. For extracellular and secondary staining, cells were washed twice prior to 30 min incubation at 4° C. in the dark with fluorescein isothiocyanate (FITC), phycoerythrin (PE), peridinin chlorophyll protein complex (PerCP), PerCP-Cy5.5, PE-Cy7, allophycocyanin (APC), and APC-Cy7 (or APC-eFluor 780)-conjugated antibodies (CD3, CD4, CD8, CD14, CD19, CD25, mouse- or human-specific CD45, CD45RA, CD45RO, CD62L, CD95, CD107a, CD137, LAG3 (CD223), PD-1 (CD279), TIM3 (CD366), CCR7, IFNγ, Goat Anti-Mouse Ig, and streptavidin) purchased from BioLegend, eBioscience, BD Biosciences or Fisher Scientific. Cell viability was determined using 4′, 6-diamidino-2-phenylindole (DAPI, Sigma). For intracellular staining, cells were fixed, permeabilized, and processed according to the PE Active-Caspase-3 Apoptosis kit (BD Biosciences) manufacturer's protocol. Cells were then incubated with fluorophore-conjugated antibodies for 30 minutes at 4° C. in the dark, and washed twice prior to resuspension in FACS buffer and acquisition on the MACSQuant Analyzer 10 (Miltenyi Biotec). Data were analyzed with FlowJo software (v10, TreeStar).

In Vitro T Cell Functional Assays: For degranulation and intracellular cytokine assays, CAR T cells and tumor targets were co-cultured at varying effector:target ratios in complete X-VIVO without exogenous cytokines in round-bottom 96-well tissue culture-treated plates (Corning). FITC-CD107a was added to cultures and after incubating for 4-6 hrs at 37° C., cells were fixed and permeabilized before analysis by flow cytometry as described above. For tumor killing assays, CAR T cells and tumor targets were co-cultured at varying effector:target ratios in complete X-VIVO without exogenous cytokines in 96-well plates for 1-5 days and analyzed by flow cytometry as described above. Tumor killing by CAR T cells was calculated by comparing CD45-negative cell counts relative to that observed by Mock T cells.

ELISA and Multiplex Cytokine Assays: Varying concentrations of recombinant human PSCA protein (amino acids 23-95; Abnova) was coated overnight in 1×PBS at 4° C. on high-affinity 96-well flat bottom plates (Corning). Wells were washed twice with 1×PBS, blocked with 10% FBS for 1 hr, and washed again. CAR T cells ($5\times10^3$ in 200 µL) were added to coated wells. Where specified, tumor targets ($5\times10^3$) were incubated with T cells in non-coated wells (final volume of 200 µL). Following an overnight incubation at 37° C., supernatants were harvested and processed according to the Human IFNγ ELISA Ready-SET-GO! ® (eBioscience) manufacturer's protocol. Plates were read at 450 nm using the Wallac Victor3 1420 Multilabel Counter (Perkin-Elmer) and Wallac 1420 Workstation software. Alternatively, supernatants were analyzed for multiple cytokines using the Multiplex Bead Immunoassay Kit (Invitrogen) according to the manufacturer's protocol. Human PSA/KLK3 ELISA (Abcam) on mouse serum was run according to manufacturer's protocol.

Quantitative PCR: Tumor cells (plated at ($0.25\times10^6$/mL) were cultured for one day prior to RNA isolation. RNA was extracted using RNeasy® Mini Kit column purification (Qiagen). cDNA was prepared using SuperScript™ IV First-Strand Synthesis System (Invitrogen). RNA primers were generated using TaqMan® Gene Expression Assays specific to either PSCA (Hs04166224_g1, Life Technologies) or GAPDH (Hs02758991_g1, Life Technologies). qPCR was performed on a ViiA™ 7 Real-Time PCR System (Thermo Fisher). Primer sets were validated using a standard curve across a specified dynamic range with a single melting curve peak. Expression of target genes was normalized to GAPDH.

In Vivo Tumor Studies: All animal experiments were performed under protocols approved by the City of Hope Institutional Animal Care and Use Committee. For subcutaneous tumor studies, PC-3 and DU145 cells (2.5×10$^6$) were prepared in HBSS$^{-/-}$ and injected subcutaneously in the left depilated belly of male NSG mice. Tumor growth was monitored 3 times per week via caliper measurement. Once tumor volumes reached 50-500 mm$^3$, CAR T-cells were prepared in PBS and injected either intratumorally (i.t.) or intravenously (i.v.). Once tumors reached 15 mm in diameter, mice were euthanized and tumors were harvested and processed for immunohistochemistry as described below. When subcutaneous tumors recurred, mice were treated by i.t. injection with either PSCA-CARs or HER2-CARs. Peripheral blood was collected from isoflurane-anesthetized mice by retro-orbital (RO) bleed through heparinized capillary tubes (Chase Scientific) and into polystyrene tubes containing a heparin/PBS solution (1000 units/mL, Sagent Pharmaceuticals). Approximately 150 µL of blood was collected per mouse. Blood was lysed with 1× Red Cell Lysis Buffer (Sigma) according to the manufacturer's protocol, and then washed, stained and analyzed by flow cytometry as described above.

For orthotopic intratibial tumor studies, LAPC-9 and PC-3-PSCA were transduced with lentivirus carrying enhanced green fluorescent protein (eGFP)/firefly luciferase (ffluc) to allow for non-invasive optical imaging (Xenogen) once implanted into mice (resulting lines named LAPC-9-eGFP-ffluc and PC-3-PSCA-eGFP-ffluc). Briefly, these lines were incubated with polybrene (4 mg/mL, Sigma) and the eGFP-ffluc lentivirus (see above), followed by cell sorting for GFP$^+$ cells using the BD FACSAria™ SORP cell sorter. Freshly sorted LAPC-9-eGFP-ffluc cells were serially passaged in NSG mice as described above. PC-3-PSCA-eGFP-ffluc cells (2×10$^5$) or LAPC-9-eGFP-ffluc cells (1.5×10$^5$) were prepared as in subcutaneous models. Mice were anesthetized by intraperitoneal (i.p.) injection of ketamine/xylazine and gaseous isoflurane prior to tumor injection. Tumor cells (in 30 µL HBSS$^{-/-}$) were injected in the intratibial space of the mouse hind leg. After 14 days, mice were i.v. injected with CAR T cells. Tumor growth was monitored via biweekly optical imaging (IVIS, Xenogen) and flux signals were analyzed with Living Image software (Xenogen). For imaging, mice were injected i.p. with 150 µL D-luciferin potassium salt (Perkin Elmer) suspended in PBS at 4.29 mg/mouse.

For T cell trafficking studies, mice were implanted in the right intratibial space with wild-type PC-3 cells (2×10$^5$) and in the left intratibial space with PC-3-PSCA cells (2×10$^5$). After 14 days, mice were i.v. injected with 5×10$^6$) Mock or PSCA(ΔCH2)BBζ CAR T cells that had been co-transduced with lentivirus carrying eGFP-ffluc. T cells were CAR enriched, and determined to be approximately 30% eGFP$^+$ by flow cytometry. T cell trafficking was monitored by non-invasive optical imaging (Xenogen) at 4 hr, 1 day, 2 days, and 4 days post T cell infusion. Flux signals were analyzed as described above.

Immunohistochemistry: Tumor tissue was fixed for up to 3 days in 4% paraformaldehyde (Boston BioProducts) and stored in 70% ethanol until further processing. Histology was performed by the Pathology Core at City of Hope. Briefly, paraffin-embedded sections (10-µm) were stained with mouse anti-human CD3 (DAKO), mouse anti-human PSCA (Abcam), rat anti-human HER2 (DAKO), and rat anti-human Granzyme-B (eBioscience). Images were obtained using the Nanozoomer 2.0HT digital slide scanner and the associated NDP.view2 software (Hamamatzu).

Statistical Analysis: Data are presented as mean±SEM, unless otherwise stated. Statistical comparisons between groups were performed using the unpaired two-tailed Student's t test to calculate p value. *$p<0.05$, $p<0.01$, *$p<0.001$; ns, not significant.

SEQUENCE LISTING

This application contains a Sequence Listing that has been submitted electronically as an ASCII text file named 40056_0025US1_ST25.txt. The ASCII text file, created on Nov. 8, 2019, is 74,614 bytes in size. The material in the ASCII text file is hereby incorporated by reference in its entirety.

---

What is claimed is:

1. A nucleic acid molecule encoding a chimeric antigen receptor comprising an amino acid sequence selected from the group consisting of SEQ ID NOs: 26, 28, 30, 32, 34 and 36.

2. A population of human T cells comprising a nucleic acid encoding a chimeric antigen receptor comprising an amino acid sequence selected from the group consisting of SEQ ID NOs: 26, 28, 30, 32, 34 and 36.

3. The population of human T cells of claim 2, wherein the population of T cells comprises central memory T cells.

4. A chimeric antigen receptor comprising an amino acid sequence selected from the group consisting of SEQ ID NOs: 26, 28, 30, 32, 34 and 36.

5. The nucleic acid molecule of claim 1, wherein the chimeric antigen receptor comprises an amino acid sequence selected from the group consisting of SEQ ID NOs: 26 and 32.

6. The nucleic acid molecule of claim 1, wherein the chimeric antigen receptor comprises an amino acid sequence selected from the group consisting of SEQ ID NOs: 28 and 34.

7. The nucleic acid molecule of claim 1, wherein the chimeric antigen receptor comprises an amino acid sequence selected from the group consisting of SEQ ID NOs: 30 and 36.

8. The population of human T cells of claim 2, wherein the chimeric antigen receptor comprises an amino acid sequence selected from the group consisting of SEQ ID NOs: 26 and 32.

9. The population of human T cells of claim 2, wherein the chimeric antigen receptor comprises an amino acid sequence selected from the group consisting of SEQ ID NOs: 28 and 34.

10. The population of human T cells of claim 2, wherein the chimeric antigen receptor comprises an amino acid sequence selected from the group consisting of SEQ ID NOs: 30 and 36.

11. The chimeric antigen receptor of claim 4, wherein the chimeric antigen receptor comprises an amino acid sequence selected from the group consisting of SEQ ID NOs: 26 and 32.

12. The chimeric antigen receptor of claim 4, wherein the chimeric antigen receptor comprises an amino acid sequence selected from the group consisting of SEQ ID NOs: 28 and 34.

13. The chimeric antigen receptor of claim 4, wherein the chimeric antigen receptor comprises an amino acid sequence selected from the group consisting of SEQ ID NOs: 30 and 36.

* * * * *